(12) United States Patent
Johnson et al.

(10) Patent No.: US 11,666,320 B2
(45) Date of Patent: Jun. 6, 2023

(54) FIXATION MEMBERS, ASSEMBLIES, AND RELATED SYSTEMS AND METHODS

(71) Applicant: Medos International Sarl, Le Locle (CH)

(72) Inventors: Samantha T. Johnson, Hudson, MA (US); Joseph Algeri, Burlington, MA (US); David B. Spenciner, North Attleboro, MA (US); Dennis Connelly, Arlington, MA (US); Reagan A. Theis, Lakeway, TX (US); Daniel Gamache, Dedham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 671 days.

(21) Appl. No.: 16/703,115

(22) Filed: Dec. 4, 2019

(65) Prior Publication Data
US 2020/0178951 A1     Jun. 11, 2020

Related U.S. Application Data

(60) Provisional application No. 62/775,937, filed on Dec. 6, 2018, provisional application No. 62/775,902, filed on Dec. 5, 2018.

(51) Int. Cl.
| A61B 17/04 | (2006.01) |
| A61B 17/00 | (2006.01) |
| A61B 17/06 | (2006.01) |

(52) U.S. Cl.
CPC .............. *A61B 17/0401* (2013.01); *A61B 2017/00292* (2013.01); *A61B 2017/00898* (2013.01);
(Continued)

(58) Field of Classification Search
CPC ...... A61B 17/0401; A61B 2017/00292; A61B 2017/00898; A61B 2017/0409;
(Continued)

(56) References Cited

U.S. PATENT DOCUMENTS

| 8,870,915 B2 | 10/2014 | Mayer et al. |
| 2009/0182417 A1 | 7/2009 | Tremulis et al. |

(Continued)

FOREIGN PATENT DOCUMENTS

WO     2013/016552 A1     1/2013

*Primary Examiner* — Timothy J Neal
*Assistant Examiner* — Andrew P. Restaino

(57) ABSTRACT

A suture anchor for fixation within an anatomical structure includes an actuation member in contact with an anchor body at a first location thereof. The anchor body is elongate along a direction of elongation and defines a central axis. In a neutral configuration, the anchor body is flat and defines a thickness along a transverse direction and a width along a lateral direction, the width being greater than the thickness. The anchor body has first and second tails that are braided together along a portion of the actuation member from the first location to a second location of the anchor body. The actuation member is configured to apply a force to the braided anchor body so as to actuate the anchor body in a manner increasing its maximum thickness along a second direction that is angularly offset from the direction of elongation.

6 Claims, 27 Drawing Sheets

(52) U.S. Cl.
CPC ............... *A61B 2017/0409* (2013.01); *A61B 2017/0414* (2013.01); *A61B 2017/0454* (2013.01); *A61B 2017/0496* (2013.01); *A61B 2017/06171* (2013.01)

(58) Field of Classification Search
CPC .... A61B 2017/0414; A61B 2017/0454; A61B 2017/0496; A61B 2017/06171; A61B 2017/00942; A61B 2017/0403; A61B 2017/0406
See application file for complete search history.

(56) References Cited

U.S. PATENT DOCUMENTS

| | | |
|---|---|---|
| 2011/0270278 A1 | 11/2011 | Overes et al. |
| 2013/0123810 A1 | 5/2013 | Brown et al. |
| 2013/0296934 A1* | 11/2013 | Sengun ............. A61B 17/0401 606/232 |
| 2014/0257383 A1 | 9/2014 | Lombardo et al. |
| 2014/0277133 A1 | 9/2014 | Foerster |
| 2018/0193014 A1 | 7/2018 | Chalekson et al. |

* cited by examiner

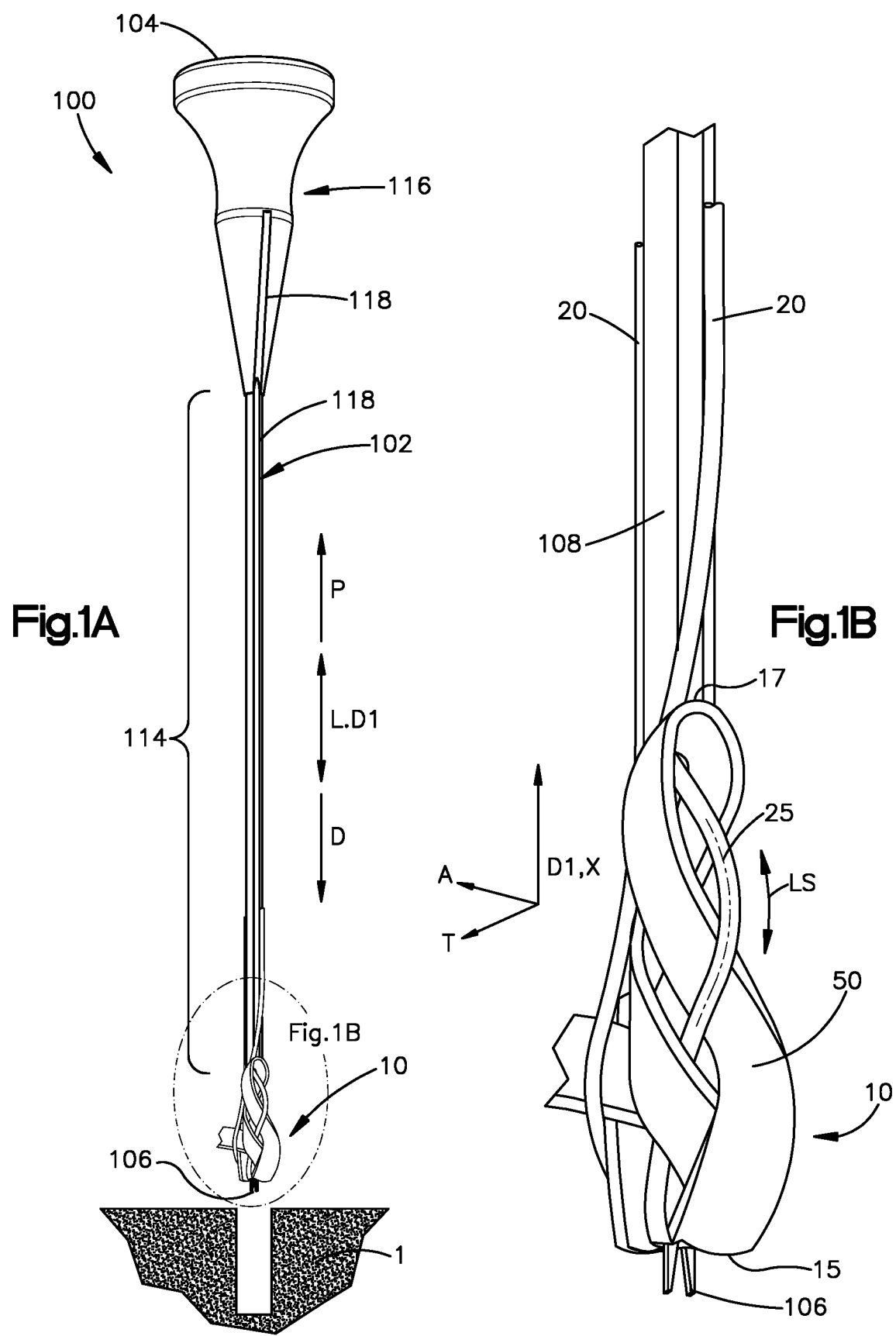

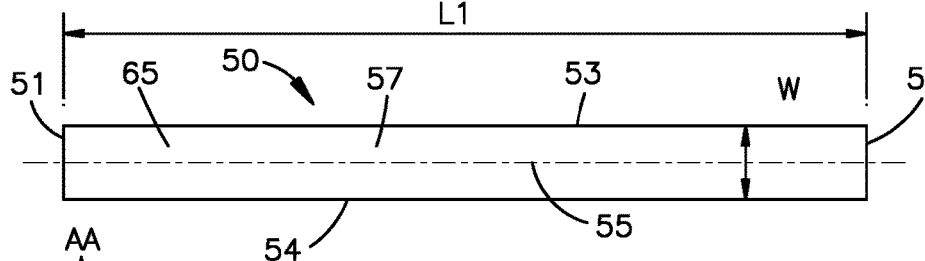
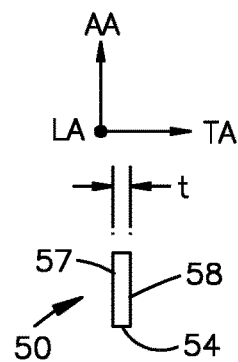
Fig.2A  Fig.2B
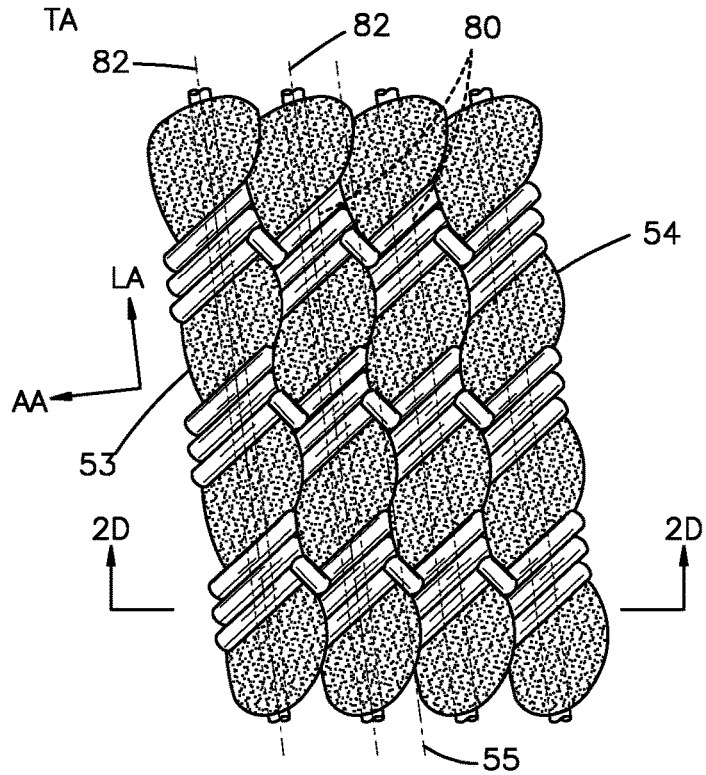
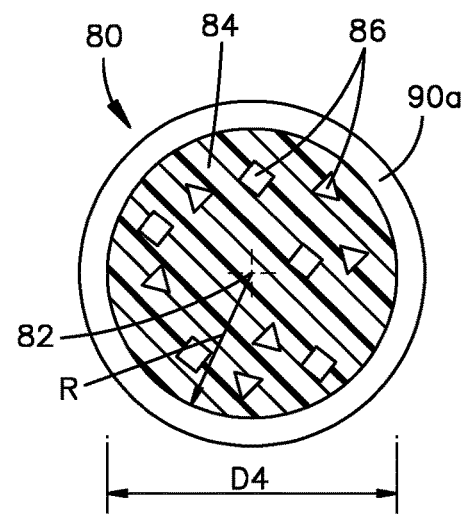
Fig.2C  Fig.2E
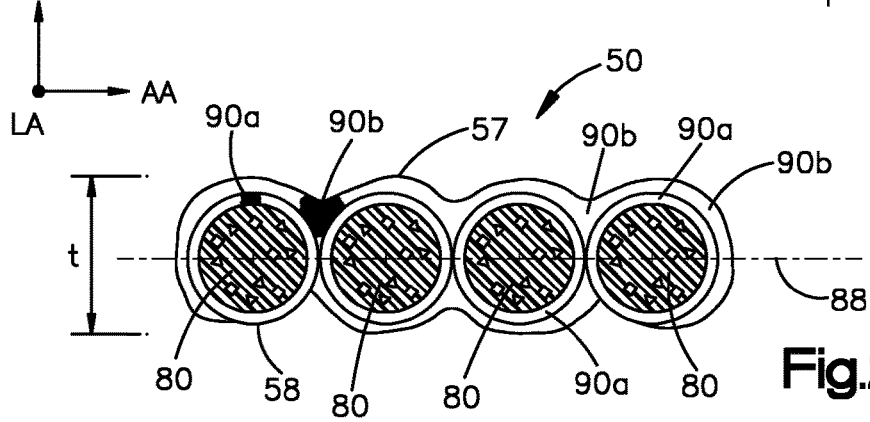
Fig.2D

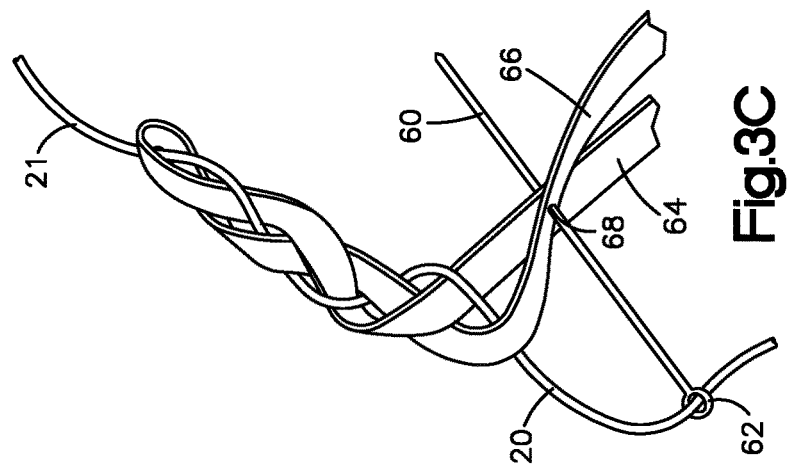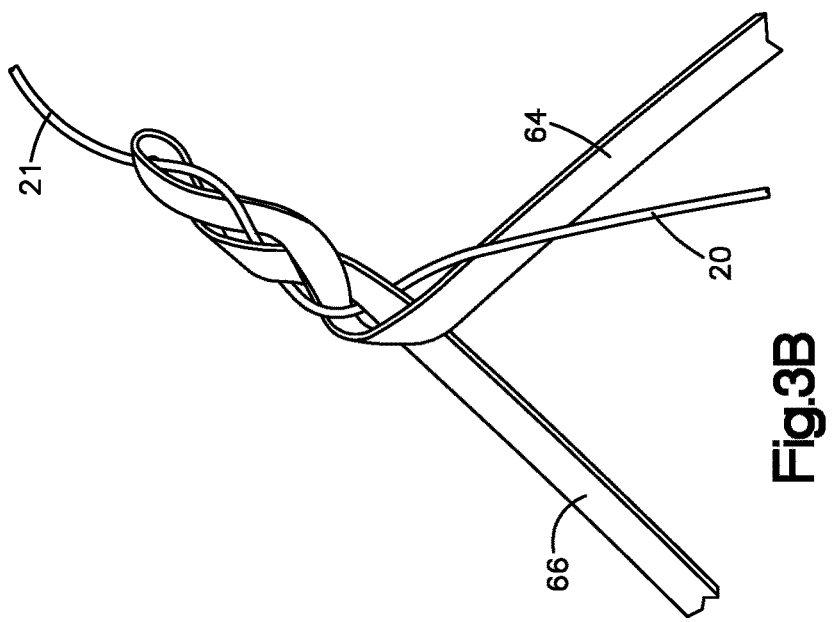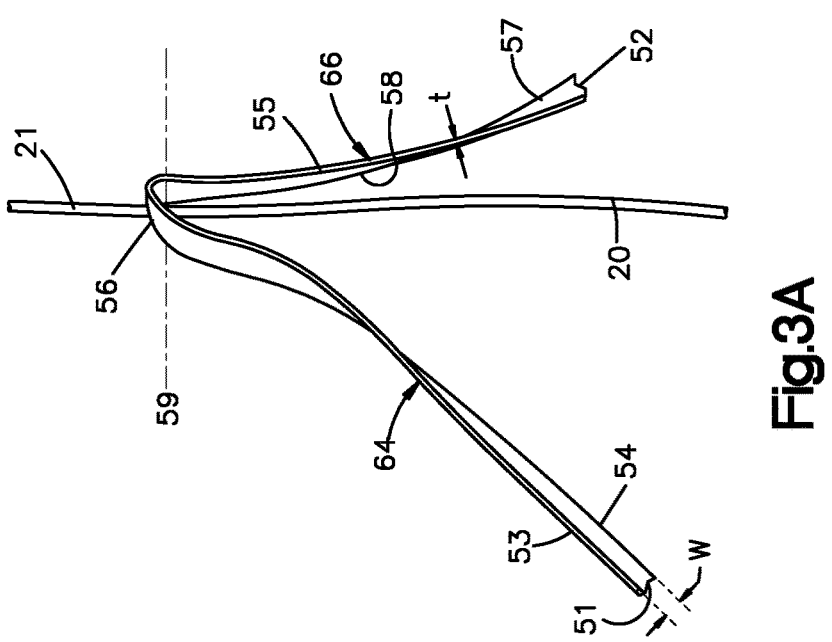

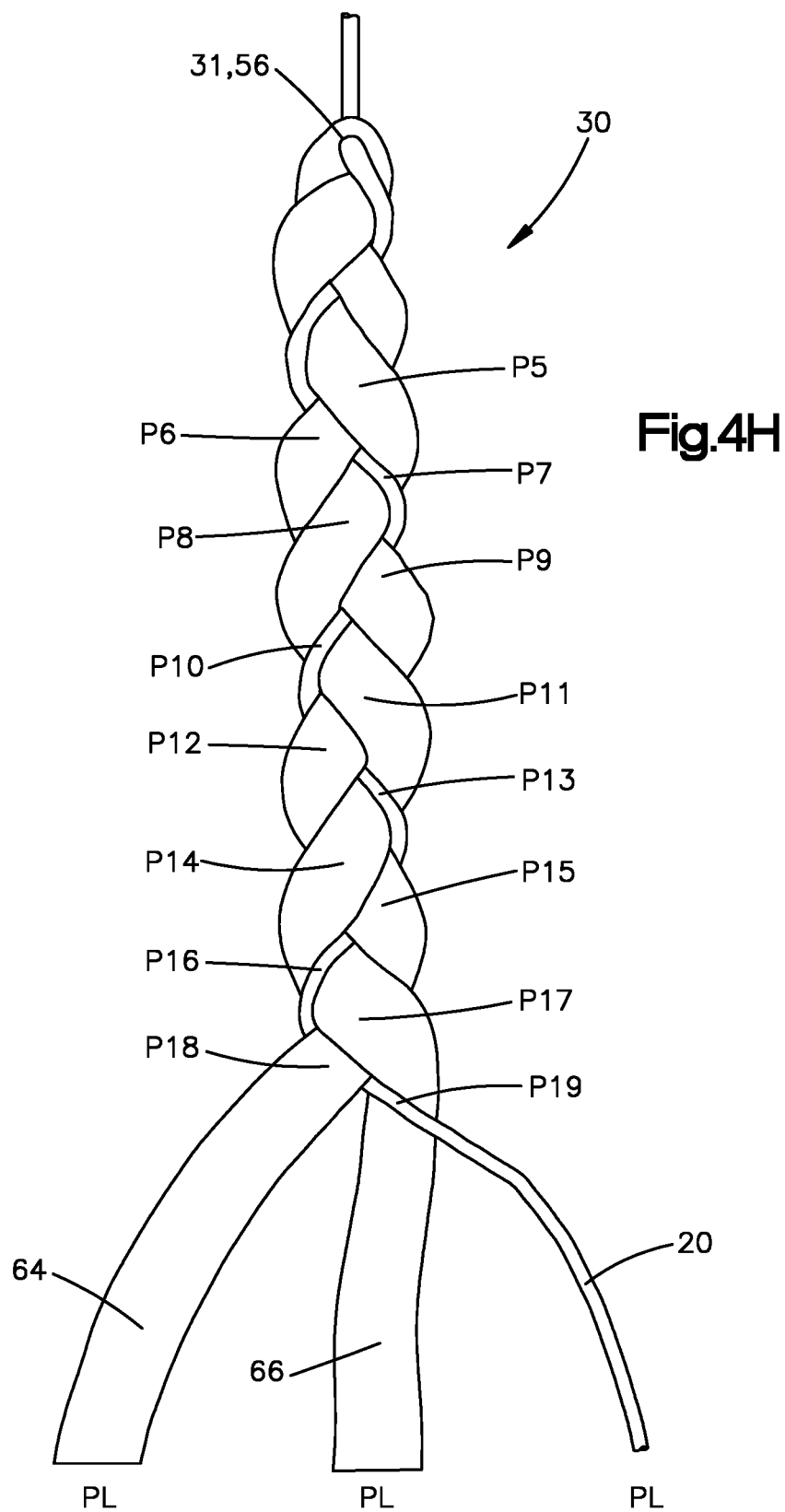

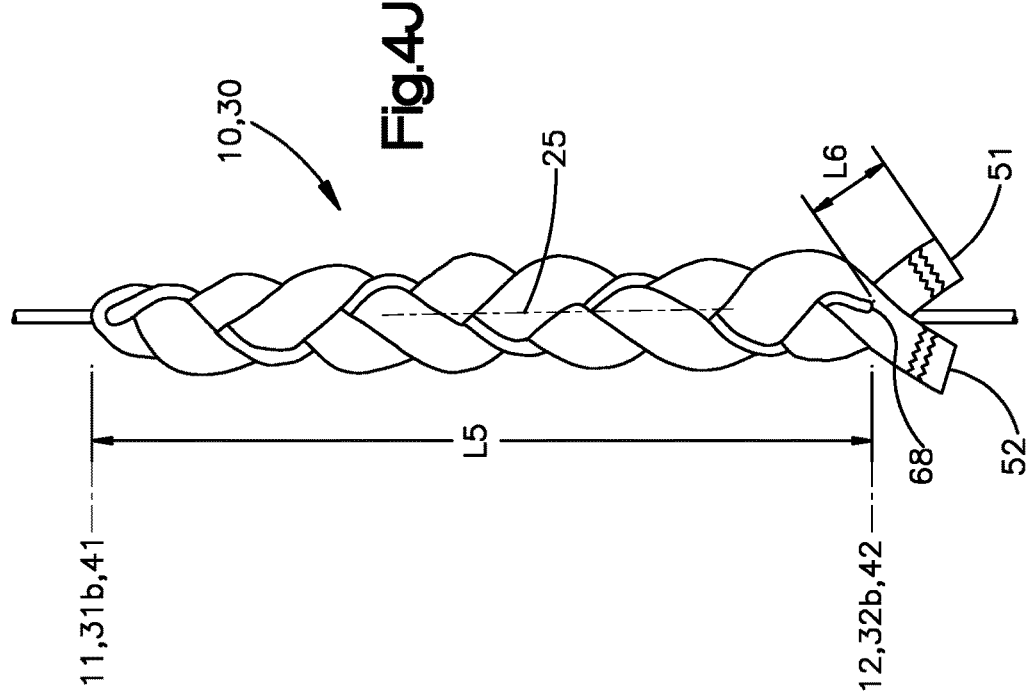
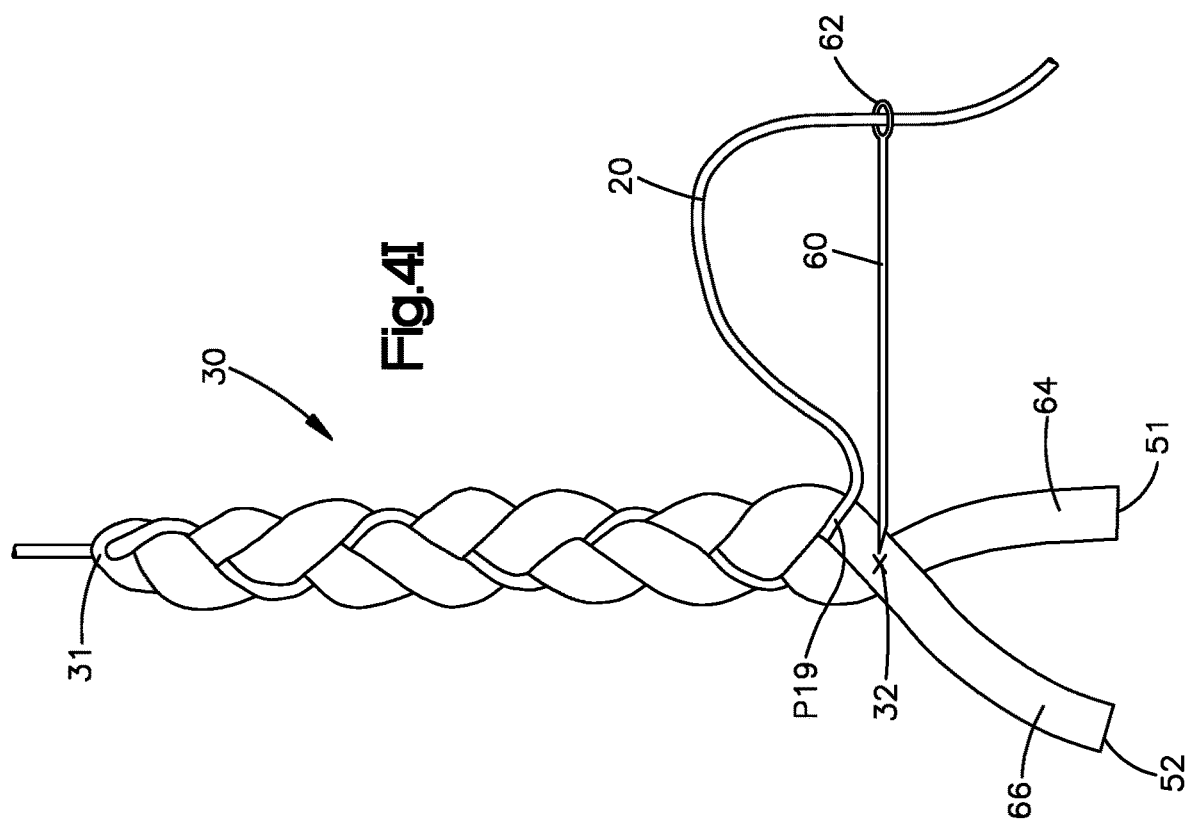

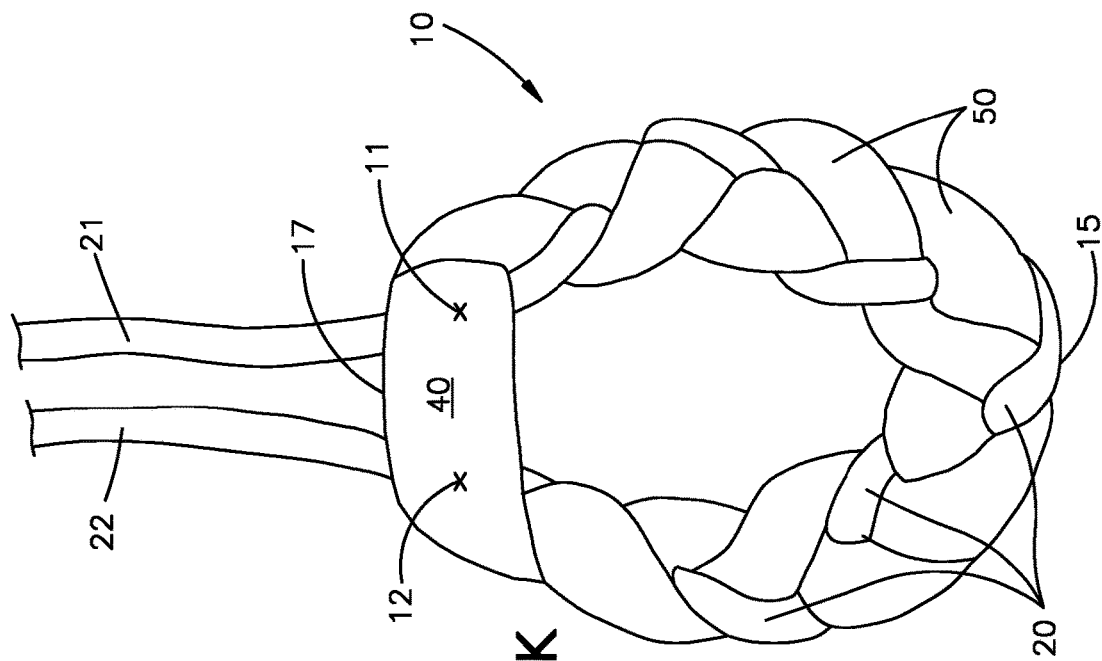
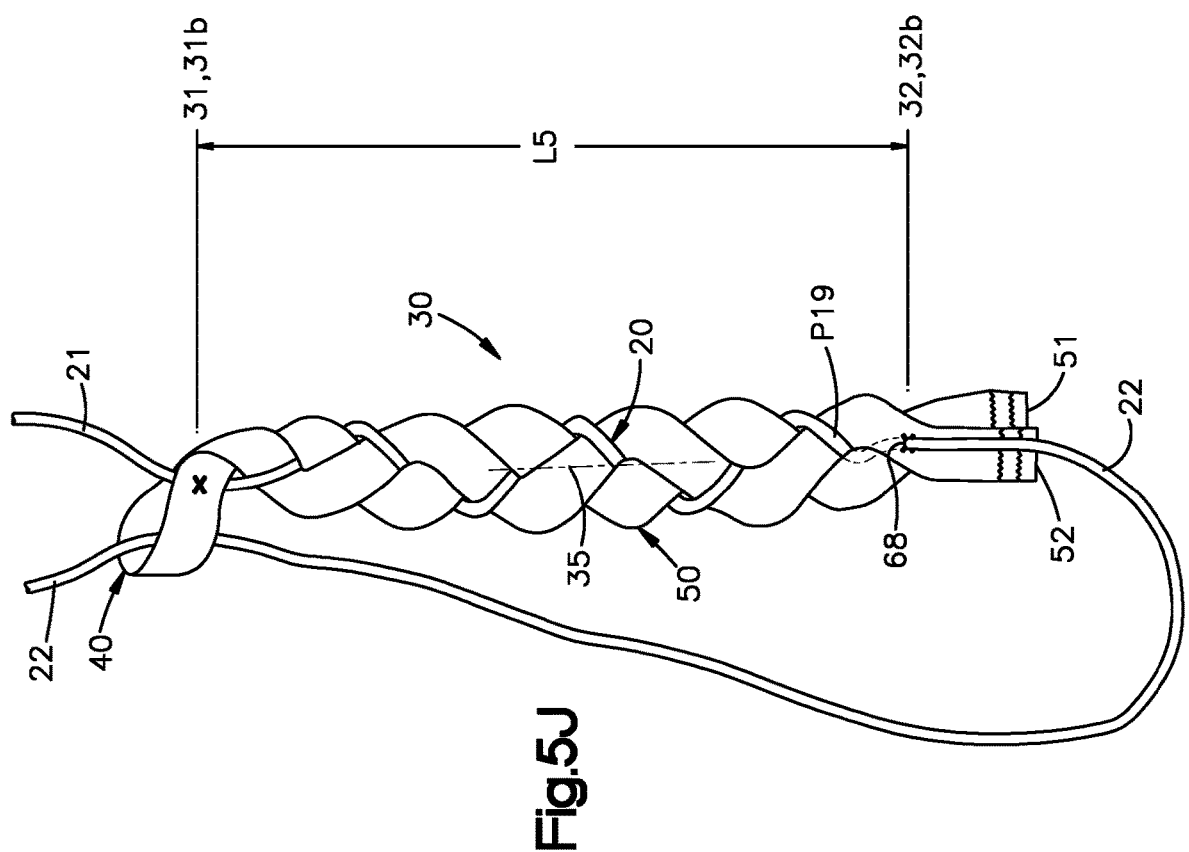

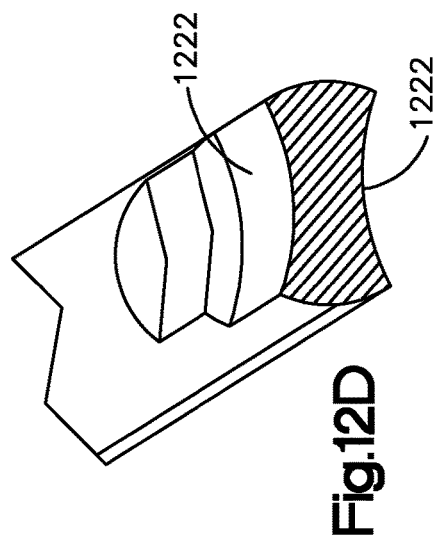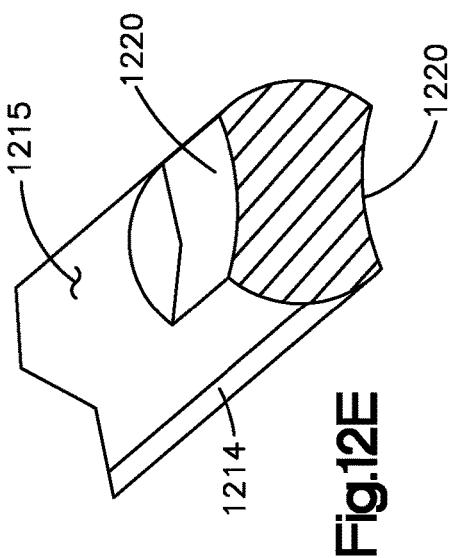
Fig.12D
Fig.12E
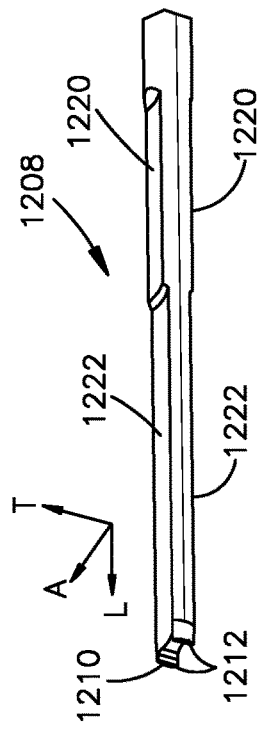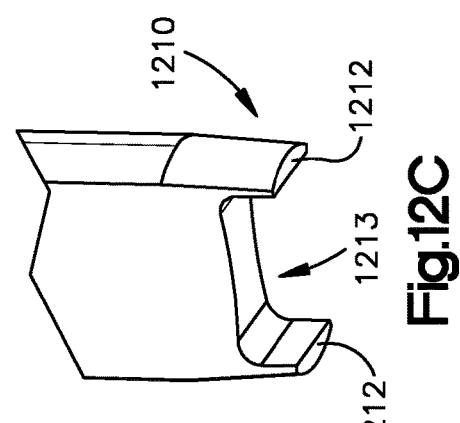
Fig.12B
Fig.12C
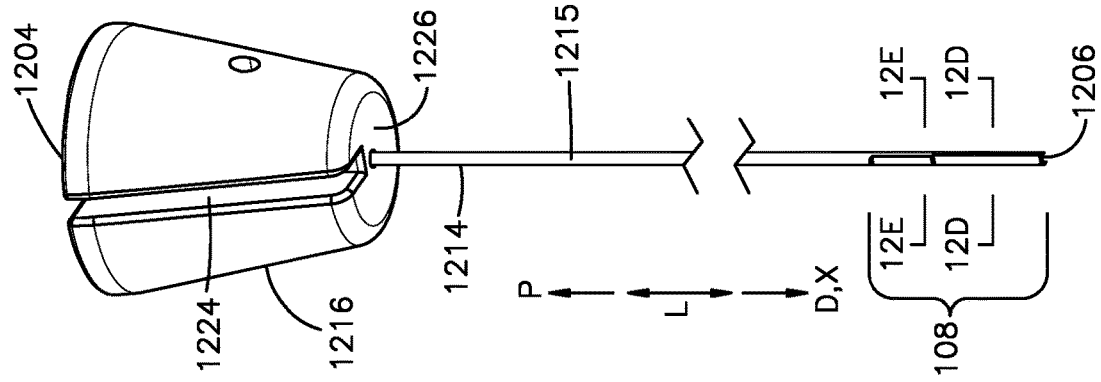
Fig.12A

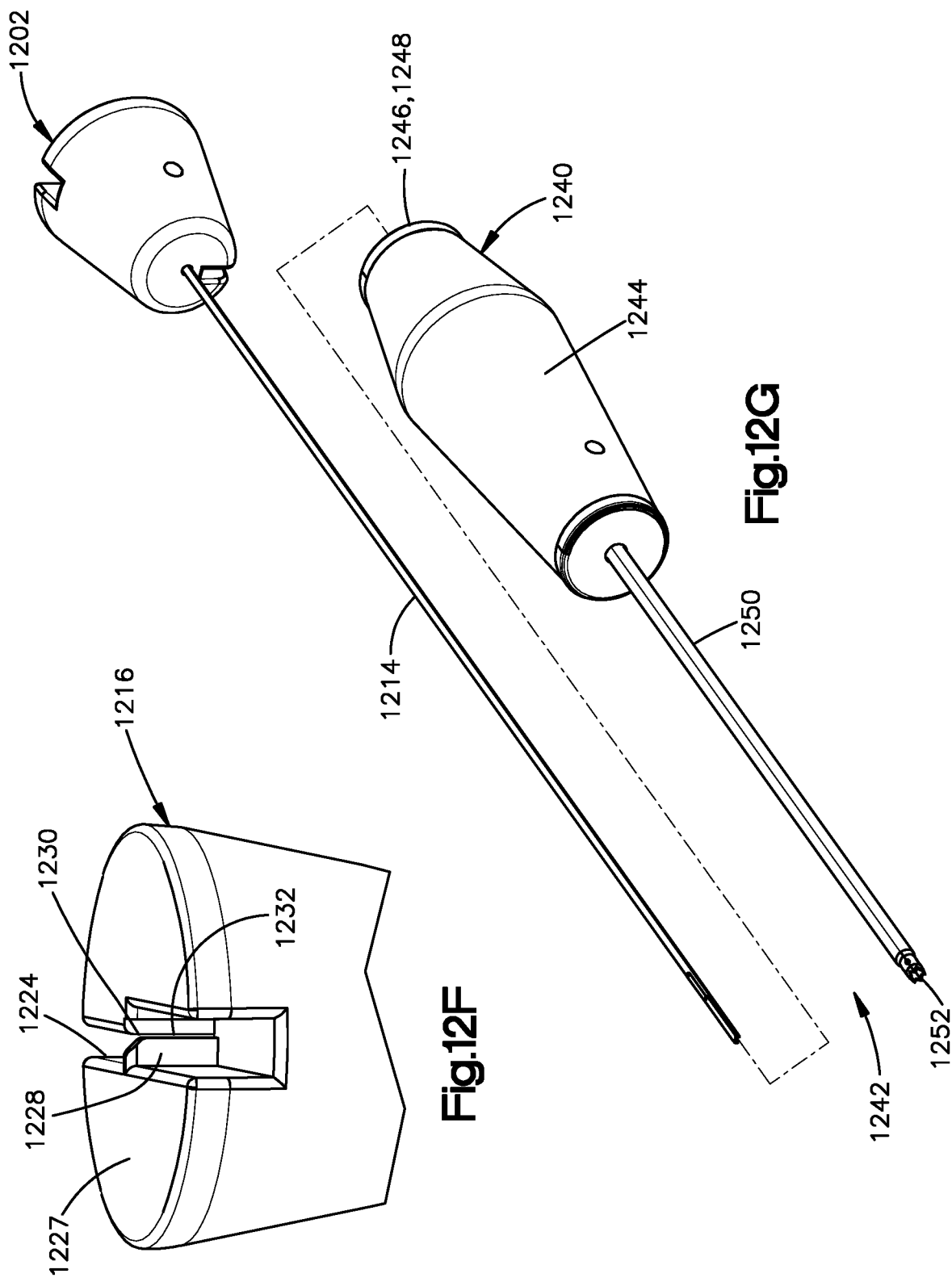

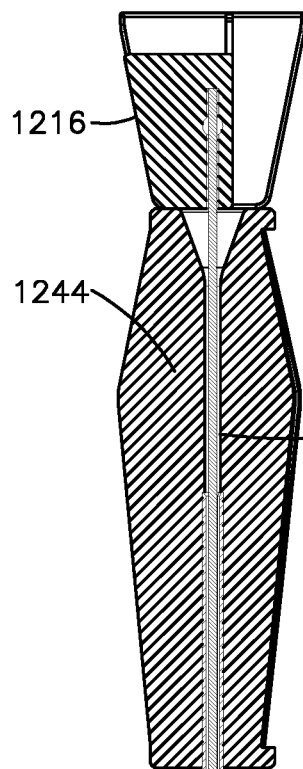
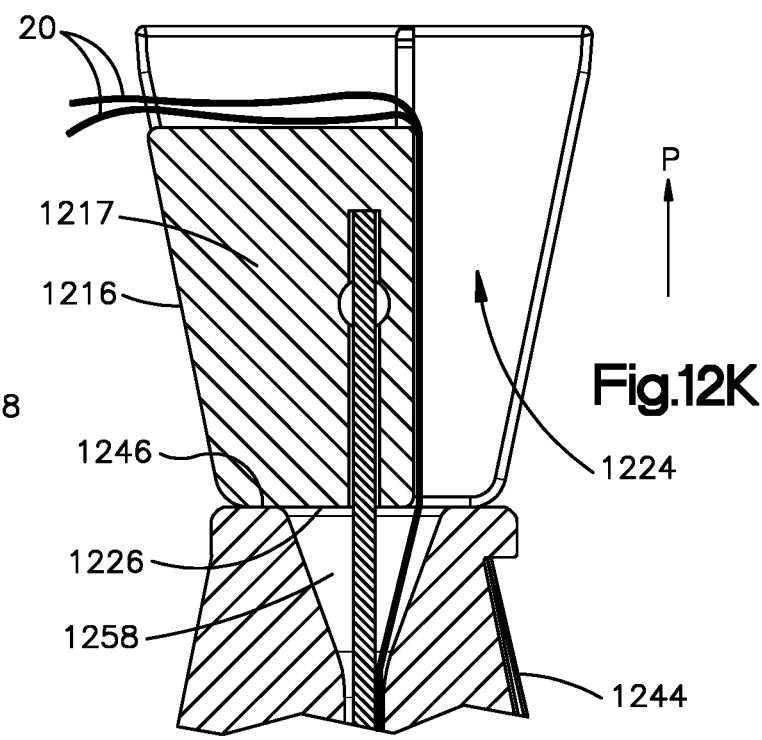
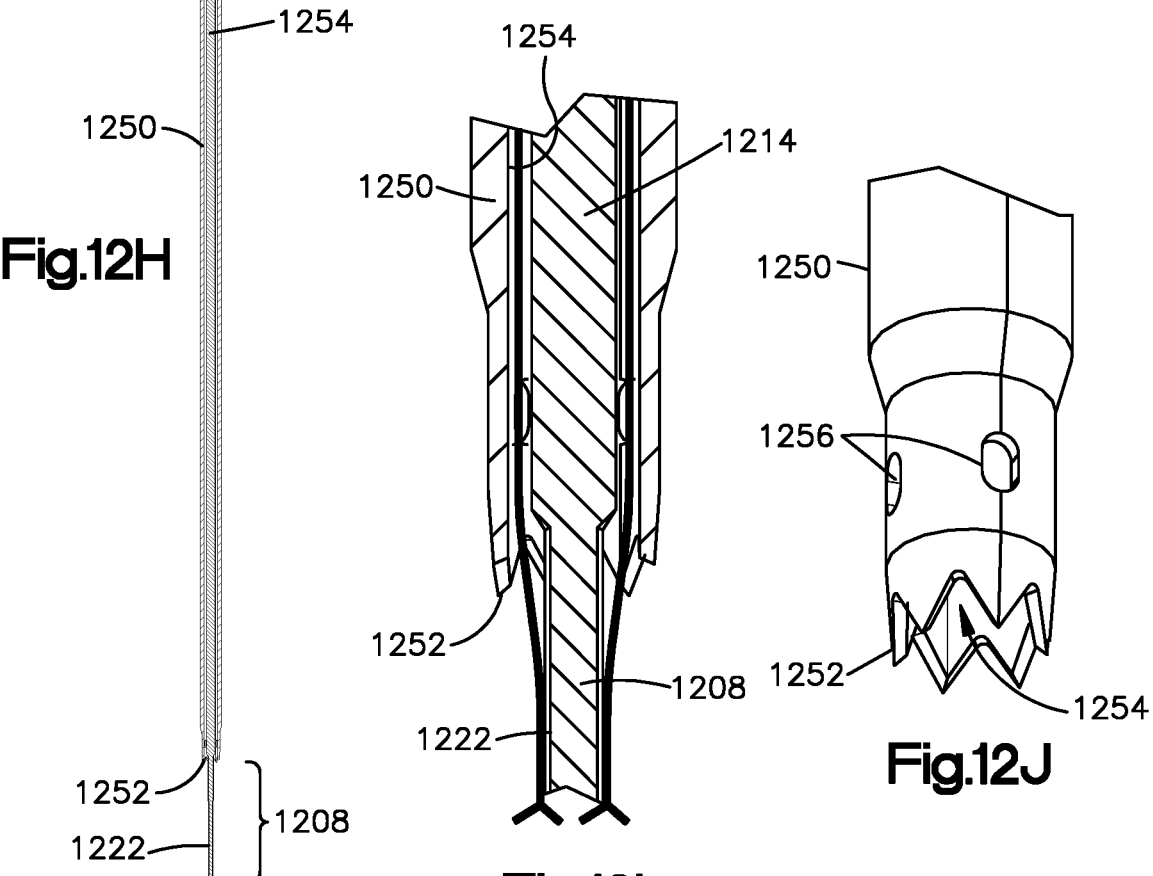

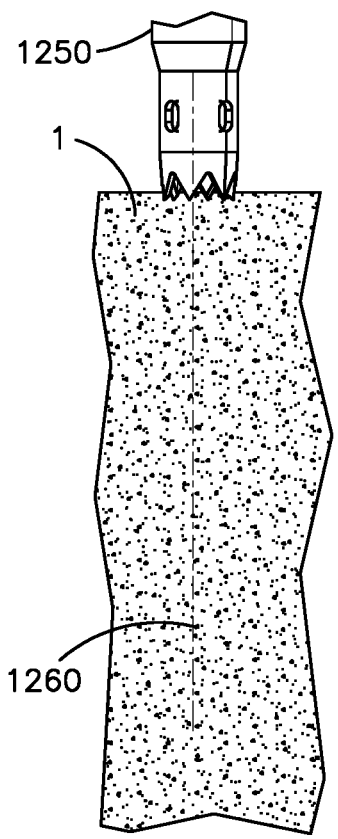 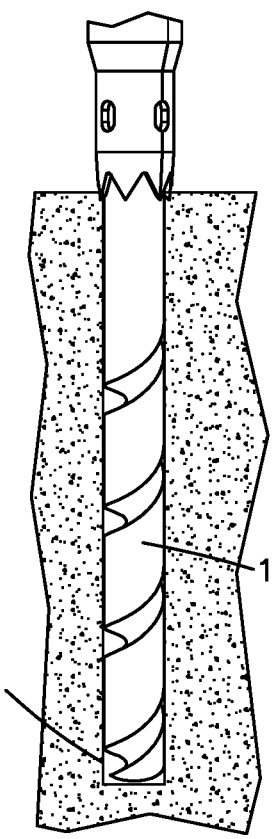 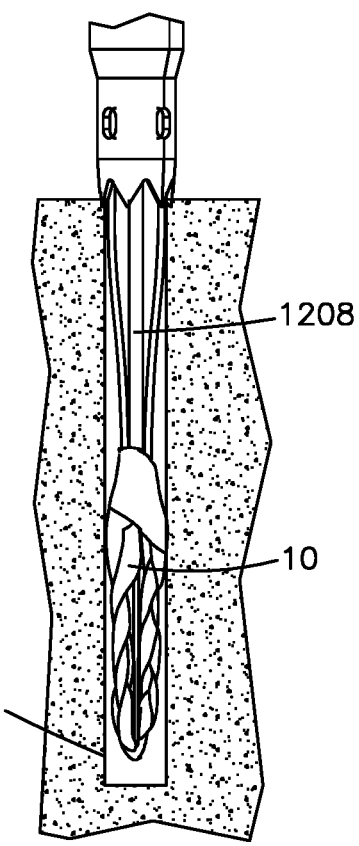
Fig.12L       Fig.12M       Fig.12N
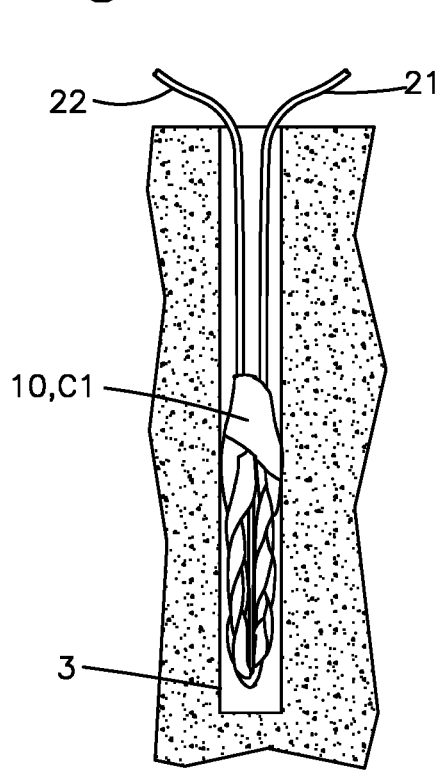 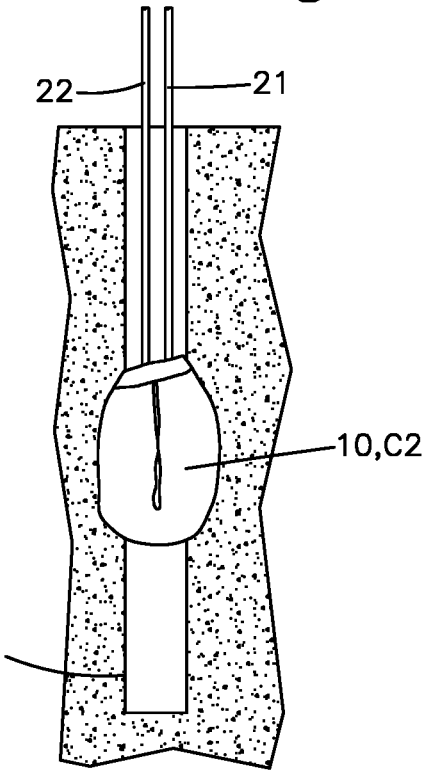
Fig.12O       Fig.12P

FIXATION MEMBERS, ASSEMBLIES, AND RELATED SYSTEMS AND METHODS

CROSS-REFERENCE TO RELATED APPLICATIONS

This application claims the benefit of U.S. Patent Application Ser. No. 62/775,902, filed on Dec. 5, 2018, in the name of Johnson et al. and U.S. Provisional Patent Application No. 62/775,937, filed on Dec. 6, 2018, in the name of Johnson et al., the entire disclosure of each of which is incorporated by reference herein.

TECHNICAL FIELD

The present invention relates in general to devices, systems and methods for repairing and anchoring damaged tissue, and more particularly, to devices, systems and methods for anchoring suture to tissue.

BACKGROUND

Injuries to tissue such as cartilage, skin, muscle, bone, tendon and ligament, frequently require surgical intervention to repair the damage and facilitate healing. Surgical procedures to repair tissue damage are often performed using sutures connected to one or more anchoring device implanted in or adjacent to the damaged tissue. The sutures can also be passed through or around the tissue according to a variety of surgical techniques to secure the repair. The sutures can also interconnect two or more anchors used to perform the repair. Suture anchors have been fabricated with bodies formed from a variety of materials including nonabsorbable materials such as metals and durable polymers, as well as bioabsorbable materials such as absorbable polymers, bioceramics, absorbable composites and processed bone. Anchors that are themselves constructed entirely or at least substantially of suture material are referred to herein as "all-suture anchors" or simply "suture anchors," and such anchors can be particularly advantageous in connection with certain types of tissue repair. For example, suture anchors display advantages in relation to fixation within bone material because the relatively soft and pliable nature of textile suture material allows suture anchors to generally fit within smaller pre-drilled holes in bone relative to other types of bone anchors, thus reducing the amount of bone that must be removed prior to anchor insertion.

Moreover, sutures can be connected through or around suture anchors in a fixed or a sliding manner, for example, using eyelets or other passages in an anchor body, and can be secured using stationary or sliding knots, interference among anchor components, interference between an anchor and surrounding tissue, or other means. Some suture anchors are designed for suture to slide unidirectional through or around the anchor, enabling a surgical repair to be tightened by tensioning a portion of the suture with respect to the anchor. Among their many surgical applications, suture anchors are used with sutures to re-attach damaged tendons or ligaments to bone, to tighten compromised tissue surrounding articulating joints, and to repair tears in cartilage, such as torn meniscal cartilage in a knee. In some applications, two or more anchors joined by an adjustable length of suture enable a tissue tear to be cinched closed, or compromised tissue to be stabilized.

Of great importance in suture anchor design is maximizing retention strength (such as the retention strength of the anchor in bone) to minimize the risk of anchor breakage or pullout (such as from bone) when an attached suture is tensioned with respect to the anchor. Some drawbacks of suture anchors can include, depending on the relevant circumstances: a fixation strength that can be lower than other anchor types due to the difficulty in setting some types of suture anchors; and achieving expansion of suture anchors in hard bone material, such as cortical bone. Other issues observed with suture anchors include laxity (i.e., loosening) and creep over time, as well as long term micro-motion at the anchor interface. These issues can decrease the amount of compression applied to a repair. Additionally, over time a gap can be introduced into the repair which is not optimal for healing.

SUMMARY

In one embodiment of the present disclosure, a suture anchor for fixation within an anatomical structure includes an actuation member in contact with an anchor body at a first location thereof. The anchor body is elongate along a direction of elongation and defines a central axis. In a neutral configuration, the anchor body is flat and defines a thickness along a transverse direction and a width along a lateral direction, the width being greater than the thickness. The anchor body has first and second tails that are braided together along a portion of the actuation member from the first location to a second location of the anchor body. The actuation member is configured to apply a force to the braided anchor body so as to actuate the anchor body in a manner increasing its maximum thickness along a second direction that is angularly offset from the direction of elongation.

In another embodiment of the present disclosure, a system for anatomical fixation includes an insertion instrument having an elongate body portion that is elongate along a direction of elongation. The insertion instrument includes an anchor carrier at a distal portion of the elongate body portion and a suture anchor configured to be carried by the anchor carrier. The suture anchor is configured for fixation within a target location of an anatomical structure. The suture anchor includes an actuation member in contact with an anchor body at a first location thereof. The anchor body is elongate along a direction of elongation and defines a central axis. In a neutral configuration, the anchor body is flat and defines a thickness along a transverse direction and a width along a lateral direction, the width being greater than the thickness. The anchor body has first and second tails that are braided together along a portion of the actuation member from the first location to a second location of the anchor body. The actuation member is configured to apply a force to the braided anchor body so as to actuate the anchor body in a manner increasing its maximum thickness along a second direction that is angularly offset from the direction of elongation.

In another embodiment of the present disclosure, a suture anchor includes an anchor for fixation within an anatomical structure includes an anchor body elongate along a direction of elongation and configured to swell along a direction that is transverse to the direction of elongation responsive to exposure to an aqueous environment. The anchor also includes an actuation member configured to apply a tensile force to the anchor body so as to actuate the anchor body from a first configuration to an expanded configuration. In the first configuration, the anchor body defines a first maximum thickness along a second direction that is angularly offset from the direction of elongation. In the expanded configuration, the anchor body defines a second maximum thickness along the second direction, wherein the second maximum thickness is greater than the first maximum thickness.

In another embodiment of the present disclosure, a suture anchor includes an anchor for fixation within an anatomical structure. The suture anchor includes an expandable anchor body configured to be actuated from a first configuration whereby the anchor body is elongate along a longitudinal direction and defines a first maximum thickness along a second direction that is angularly offset from the longitudinal direction, to an expanded configuration whereby the expandable portion defines a second maximum thickness along the second direction that is greater than the first maximum thickness. The suture anchor also includes an actuation member configured to apply a tensile force to the anchor body so as to actuate the anchor body from the first configuration to the expanded configuration. The actuation member is elongate along a second longitudinal direction and is swellable along a direction transverse to the second longitudinal direction in response to exposure to an aqueous environment.

In yet another embodiment of the present disclosure, an anchor for fixation within an anatomical structure includes an anchor body that is elongate along a longitudinal anchor direction and defines a total thickness along a transverse anchor direction perpendicular to the longitudinal anchor direction. The anchor body is configured to swell along the transverse anchor direction so as to increase the total thickness responsive to exposure to an aqueous environment. The anchor also includes a suture attached to the anchor body. The suture defines a longitudinal suture direction and is configured to contract along the longitudinal suture direction responsive to exposure to the aqueous environment. The suture is further configured to transition the anchor body from a first configuration to a second configuration responsive to tension applied to the suture, such that the transition increases the total thickness along the transverse anchor direction.

In an additional embodiment of the present disclosure, a method of preparing an anchor for fixation within an anatomical structure includes braiding a plurality of fibers and at least one axial core together so as to form a braided construct that is elongate along a longitudinal direction. The at least one axial core is configured to contract along the longitudinal direction and swell along a direction transverse to the longitudinal direction in response to exposure to an aqueous environment.

In a yet additional embodiment of the present disclosure, a fixation element includes a body that is elongate along a central axis and defines a plurality of elongate cores. Each of the elongate cores defines a central core axis that extends parallel with the central axis. Braided fibers extend between each adjacent core. Further, each of the cores is configured to contract along a direction oriented along its central core axis responsive to an aqueous environment. The body connects a first anatomical structure to a second anatomical so as to reduce a distance between the first and second anatomical structures.

In further embodiments of the present disclosure, methods of repairing an anatomical structure include deploying any of the anchors and/or fixation elements described herein.

BRIEF DESCRIPTION OF THE DRAWINGS

The foregoing summary, as well as the following detailed description of illustrative embodiments of the suture anchor constructs of the present application, will be better understood when read in conjunction with the appended drawings. For the purposes of illustrating the suture anchor constructs of the present application, the drawings show illustrative embodiments. It should be understood, however, that the application is not limited to the precise arrangements and instrumentalities shown. In the drawings:

FIG. 1A is a perspective view of a fixation kit including at least one suture anchor and an insertion instrument for positioning the anchor at a target location of an anatomical structure, according to an embodiment of the present disclosure;

FIG. 1B is an enlarged perspective view of the suture anchor at the distal end of the insertion instrument illustrated in FIG. 1A;

FIG. 2A is a top plan view of an anchor body constructed as a two-dimensional textile structure;

FIG. 2B is an end view of the anchor body illustrated in FIG. 2A;

FIG. 2C is an enlarged plan view of a portion of an anchor body, according to an embodiment of the present disclosure;

FIG. 2D is a sectional view of the anchor body taken along section line 2D-2D illustrated in FIG. 2C;

FIG. 2E is an enlarged sectional view of an axial core of the anchor body, taken along section line 2C-2C illustrated in FIG. 2B;

FIG. 3A-E illustrate method steps for creating the anchor illustrated in FIG. 1B;

FIG. 4A-J illustrate method steps for creating a suture anchor according to another embodiment of the present disclosure;

FIG. 5A-K illustrate method steps for creating a suture anchor that defines a proximal loop interconnecting folded ends of the anchor, according to another embodiment of the present disclosure;

FIG. 12A is a perspective view of an insertion instrument for positioning a suture anchor at a target location of an anatomical structure, according to another embodiment of the present disclosure;

FIG. 12B is an enlarged perspective view of a distal tip of the insertion instrument illustrated in FIG. 12A;

FIG. 12C is an enlarged perspective view of a fork structure of the distal tip illustrated in FIG. 12B;

FIGS. 12D-E are sectional end views of the distal tip taken along section lines 12D-12D and 12E-12E, respectively, shown in FIG. 12A;

FIG. 12F is a perspective view of a proximal end of the insertion instrument illustrated in FIG. 12A;

FIG. 12G is a partially exploded perspective view of an instrument assembly including the insertion instrument illustrated in FIG. 12A and a guide member, according to an embodiment of the present disclosure;

FIG. 12H is a sectional side view of the instrument assembly illustrated in FIG. 12G in a fully seated configuration;

FIG. 12I is an enlarged sectional side view of a distal portion of the instrument assembly illustrated in FIG. 12H;

FIG. 12J is an enlarged perspective view of a distal end of the guide member illustrated in FIG. 12G;

FIG. 12K is an enlarged sectional side view of a proximal portion of the instrument assembly illustrated in FIG. 12H;

FIGS. 12L-P illustrated method steps for using the instrument assembly illustrated in FIGS. 12G-K to deploy an anchor within the target location.

DETAILED DESCRIPTION

Figure 1D:
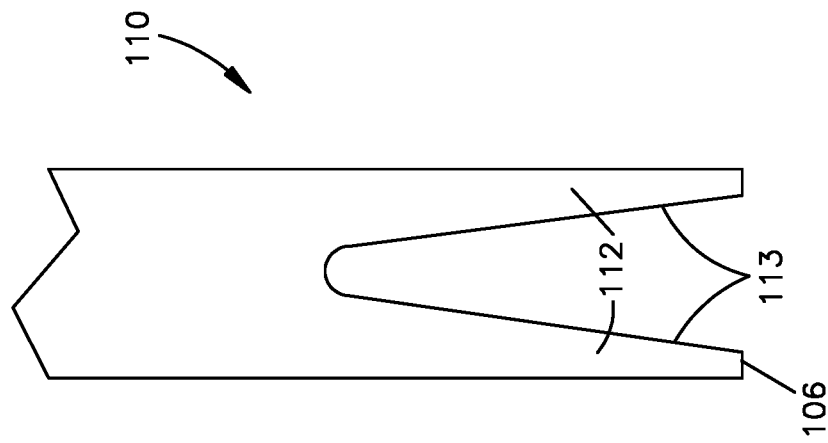
FIG. 1D is front elevation view of the forked distal tip of the insertion instrument illustrated in FIG. 1A.
Figure 1C:
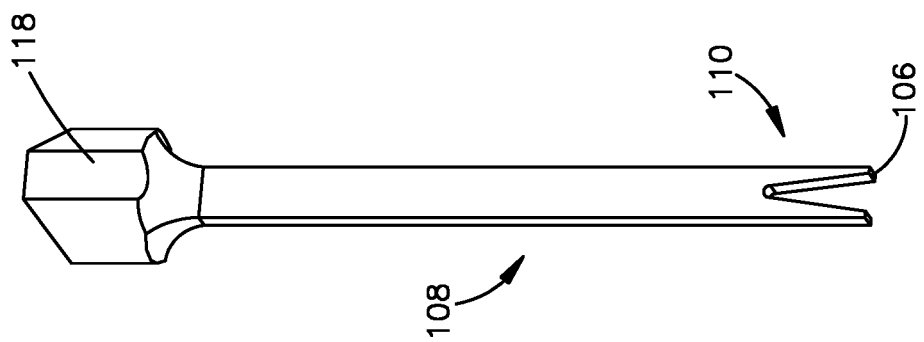
FIG. 1C is a side elevation view of a forked distal tip of the insertion instrument illustrated in FIG. 1A.

The present disclosure relates to suture anchors having constructions that are insertable within an anatomical structure (such as a pre-drilled hole in bone, for example) in a first configuration and are thereafter expandable according to one or more modes of expansion that provide increased anchor fixation strength. Furthermore, the suture anchors set forth below can reduce the laxity in a suture-based anatomical repair and even reduce a gap (if one is present) thus creating a more stable healing environment. Moreover, the suture anchors set forth below are configured to avoid, mitigate, and even actively reduce loss of compression across a repair thereby increasing the chance for healing to occur.

Referring now to FIGS. 1A-G, a fixation kit 100 can include at least one suture anchor 10 that is configured to meet the foregoing objectives and is loaded on an insertion instrument 102 configured to inject the anchor 10 in an anatomical structure 1. The suture anchor 10 can include an anchor body 50 and an actuation member 20. As will be appreciated from the description below, the anchor body 50 can be configured to iterate from a first or initial configuration to an expanded configuration. The actuation member 20 can apply an actuation force to the anchor body 50 that causes the anchor body 50 to expand from the first configuration to the expanded configuration. Accordingly, the actuation member 20 can also be referred to as an "operative suture." Further, one or both of the actuation member 20 and the anchor body 50 can be swellable in response to exposure to an aqueous environment, as described in more detail below.

The insertion instrument 102 can include a proximal end 104 and a distal end 106 spaced from each other along a longitudinal instrument direction L that defines an insertion direction X of the anchor 10. The distal end 106 is spaced from the proximal end 104 in a distal direction D along the longitudinal instrument direction L. In one example, the insertion direction X can be defined by the distal direction D. The proximal end 104 is spaced from the distal end 106 in a proximal direction P along the longitudinal instrument direction L and opposite the distal direction D. It is to be appreciated that the longitudinal instrument direction L is bi-directional, wherein the distal and proximal directions D, P are each a mono-directional component of the longitudinal instrument direction L.

The instrument 102 defines an elongate body portion 114 that is elongate along the longitudinal instrument direction L, and a distal tip 108 that extends from the body portion 114. The distal tip 108 can define the distal end 106 of the insertion instrument 102. The instrument 102 can be configured to carry the anchor 10 during insertion into an anatomical site. For instance, the distal tip 108 can be configured to carry an anchor body 50 of the anchor 10 while the anchor body 50 is in the initial or first configuration. Accordingly, the distal tip 108 can be referred to as an "anchor carrier" and can be characterized as being located at a distal portion of the body portion 114.

In one example, the distal tip 108 can define a fork structure 110 that includes a pair of tines 112 that extend from the body portion 114 along the distal direction D. The tines 112 can define respective inner surfaces 113 that generally face each other flare away from each other as they extend in the distal direction D. The distal tip 108 is configured to receive at least a portion of the anchor 10 between the tines 112, and in particular between the inner surfaces 113. Thus, the tines 112 can be disposed on either side of the anchor 10 when the distal tip 108 supports the anchor 10. Thus, the instrument 102 can be configured to retain a position of the anchor 10 relative to the distal tip 108 during insertion. The tines 112 can define respective outer surfaces that are opposite the inner surfaces and in line with respective outer surfaces of the body portion 114 of the instrument 102. During operation, the anchor body 50 can be supported by the distal tip 108, and the distal tip 108 can be inserted into a target location of the anatomical structure 1 so as to drive the anchor body 50 to the target location. The target location can be defined by a hole that extends into the anatomical structure 1. As will be appreciated below, the actuation member 20 can be attached to the anchor body 50, such that a portion of the actuation member 20 can also be supported by the distal tip 108 and driven into the target location. It is to be appreciated that the instrument 102 has been described in accordance with one example, and that other instrument distal tip structures and geometries are within the scope of the present disclosure.

The insertion instrument 102 can include a handle 116 that extends from the elongate body portion 114 in the proximal direction P. The handle 116 can define the proximal end 104 of the insertion instrument 102. Thus, the elongate body portion 114 can extend between the distal tip 108 and the handle 116. The insertion instrument 102 can further include at least one channel 118 that extends into the handle 116, and extends through the handle 116 along the longitudinal instrument direction L. In one example, the insertion instrument 102 can include a pair of channels 118 that are opposite each other. For instance, the channels 118 can be opposite each other along a transverse instrument direction T, and the tines 112 can be opposite each other along a lateral instrument direction A that is angularly offset with respect to the transverse instrument direction T. In one example, the lateral and transverse instrument directions A, T can be perpendicular to each other. Further, the lateral and transverse instrument directions A, T can each be perpendicular to the longitudinal instrument direction L. The elongate body portion 114 can define planar surfaces that are opposite each other along the transverse instrument direction T. The planar surfaces can extend along respective planes that are defined by the longitudinal instrument direction L and the lateral instrument direction A.

The at least one channel 118 can be configured to receive the actuation member 20 of the anchor 10 as the anchor 10 is driven into the target location of the anatomical structure 1 during an anchor insertion procedure. The handle portion 116 can be configured to receive insertion forces, such as impaction forces (e.g., from a mallet), that drive the distal tip 108, and thus the anchor 10, into the anatomical structure.

As shown in FIG. 1B, the anchor body 50 can be elongate along a direction of elongation D1. When the anchor body 50 is in the first configuration, the direction of elongation D1 can coincide with the insertion direction X. The actuation member 20 can be connected to the anchor body 50 while the anchor body 50 is in the first configuration. In the embodiments of the present disclosure, the anchor body 50 and the actuation member 20 can both be made from a suture material. The suture material of the anchor body 50 can be the same suture material of the actuation member 20. Alternatively, the anchor body and the actuation member 20 can be made from different suture materials. In one example, the suture material can be a textile suture material. The actuation member 20 can also be referred to as a "joining" element in that it is configured to connect or join the anchor body 50 (and thus also an anatomical structure 1 to which the anchor body 50 is anchored) either directly or indirectly to another anchoring device. The anchoring device can be another suture anchor or any suitable alternative structure (which need not be a suture anchor) and/or another anatomical structure 1, such as cartilage, muscle, bone, tendon, and/or ligament, by way of non-limiting example. The actuation member 20 defines a central, longitudinal axis 25 that extends along and a respective longitudinal suture direction LS of the actuation member 20. It is to be appreciated that the longitudinal axis 25 and the longitudinal suture direction LS of the actuation member 20 need not be straight and will both be determined by the present path along which the actuation member 20 extends. The suture material construction of the anchor body 50 can allow the anchor body 50 to be folded or otherwise bent over the distal tip 108 of the insertion instrument 102, such as in a U-shape or V-shape, which aids in the insertion of the anchor body 50 within a small drill hole in the target location of the anatomical structure 1, and also helps preserve the shape of the anchor body 50 during insertion. In such embodiments, the folded or otherwise bent suture anchor 10 defines a distal end 15 at an apex of the bend or fold and a proximal end 17 spaced from the distal end 15 in the proximal direction P. In one example, the drill hole can have a diameter in a range of about 2.0 mm (about 0.079 inch) or less. In additional embodiments, the drill hole can have a diameter in a range from less than 1.0 mm (less than about 0.039 inch) to about 5.0 mm (about 0.236 inch).

As described above, at least a portion of the anchor 10, such as one or both of the actuation member 20 and the anchor body 50 can be configured to swell when exposed to an aqueous environment, such as occurs in vivo. For instance, one or both of the actuation member 20 and the anchor body 50 can include at least one axially-extending elastic core that swells when exposed to the aqueous environment. It is to be appreciated that the actuation member 20 can be DYNACORD™ or DynaTape, available from DePuy Synthes Mitek Sports Medicine of Raynham, Mass. Moreover, the actuation member 20 can be configured according to any of the embodiments described more fully in U.S. Pat. No. 8,8701,915, issued Oct. 28, 2014, in the name of Mayer et al., the entire disclosure of which is incorporated herein by this reference. Thus, the actuation member 20 preferably includes an axial core that swells radially (i.e., in a radial direction perpendicular to its central axis) and contracts axially (i.e., along a direction oriented along its central axis) responsive to exposure to an aqueous environment. The radial swelling and axial contraction of the axial core causes the anchor body itself to swell radially and contract axially in like fashion. Accordingly, the actuation member 20 can be configured to avoid or reduce the laxity in the system and can "pull" in a gap in the anatomy connected by the actuation member 20 if such a gap forms, thus creating a more stable healing environment. Additionally, the swellability of the anchor body 50 (as well as the swellability of the actuation member 20) increases the overall radial expansion of the device. Thus, the swellability of the anchor body 50 can create additional fixation of the anchor body 50 in the target location of the anatomical structure. Furthermore, the inclusion of certain substances, such as tri-calcium phosphate (TCP) within the core(s) of the actuation member 20 and/or the anchor body 50 also promote bonny ingrowth to the anchor body, which will increase the fixation strength and reduce the likelihood of micro-motion to occur. Thus, it can be seen that the suture anchors 10 of the present disclosure are capable of multiple modes of fixation within bone.

In other embodiments, the actuation member 20 can be at least partially absorbable within an aqueous environment, such as within the patient. In such embodiments, the actuation member 20 can be ORTHOCORD™ brand suture having a polydioxanone (PDS) core and/or PERMA-CORD™ brand suture, both available from DePuy Synthes Mitek Sports Medicine.

Figure 1E:
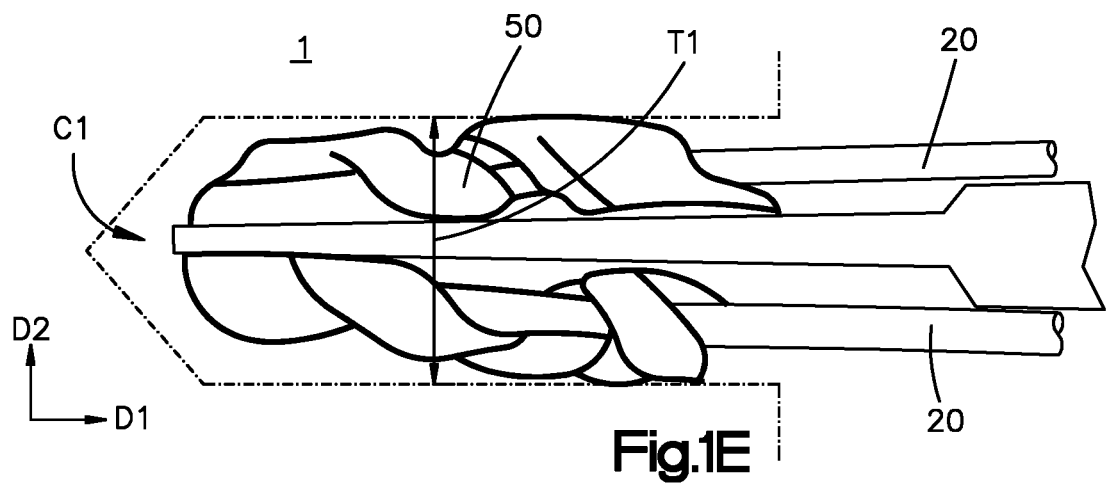
FIG. 1E is a side elevation view of the anchor deployed within the anatomical structure, showing the anchor in a first configuration.
Figure 1F:
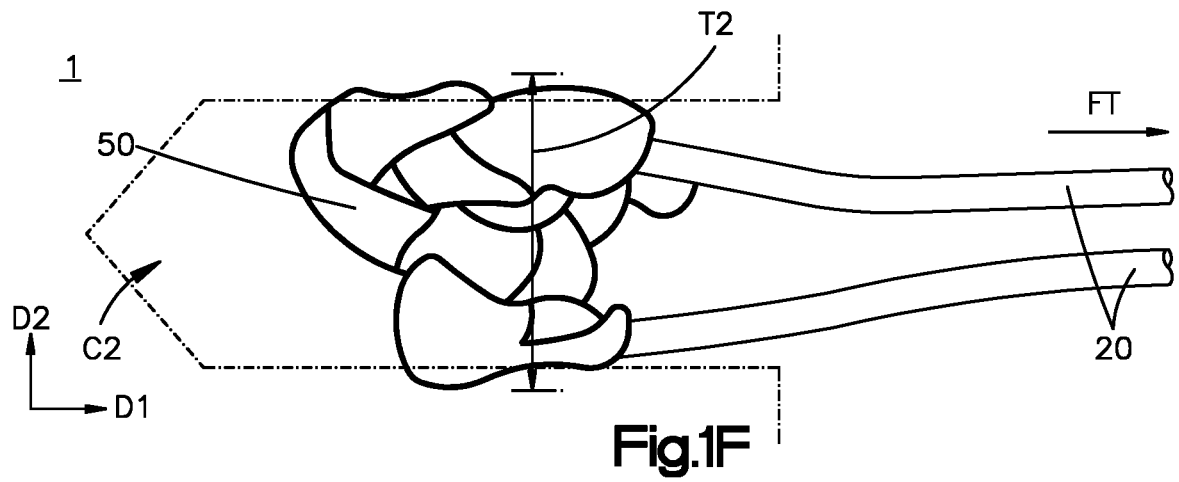
FIG. 1F is a side elevation view of the anchor deployed within the anatomical structure and actuated into an expanded configuration by an actuation member.
Figure 1G:
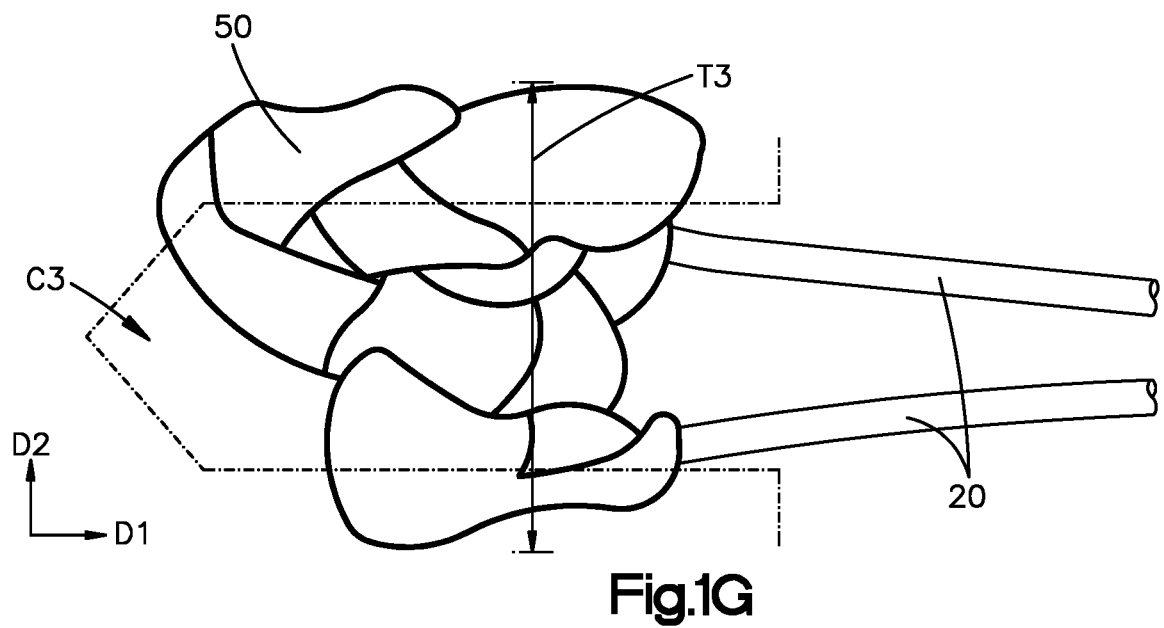
FIG. 1G is a side elevation view of the anchor deployed within the anatomical structure and swollen into a further expanded configuration.

Referring now to FIGS. 1E-G, the anchor 10 can be inserted within a target location of an anatomical structure 1, which can be configured as a pre-formed hole (which has been drilled or awled, by way of non-limiting examples) within the anatomical structure 1, by driving or otherwise advancing the distal tip 108 of the insertion instrument 102 (with the anchor 10 loaded thereon) into the anatomical structure 1. In other embodiments, the anchor 10 can be loaded onto and/or within an insertion instrument capable of puncturing the anatomical structure 1 to the target location while the anchor 10 is loaded. Once the anchor body 50 is inserted into the target location of the anatomical structure 1 at a desired depth, the insertion instrument 102 can be withdrawn. In one example, the insertion instrument 102 can be withdrawn without requiring an additional member, such as a pusher or the like, to push against the anchor body 50 as the instrument withdraws. In particular, the anchor body 50 can be sized to bear against the anatomical structure 1, such that frictional retention forces between the anchor body 50 and the anatomical structure 1 maintain the anchor body 50 in the target location as the instrument 102 is withdrawn. It should be appreciated that in other embodiments the insertion instrument 102 can be configured to extend within a guide member so as to advance the anchor 10 through the guide member to the target location of the anatomical structure 1. Alternatively or additionally, it should be appreciated that a pusher member can brace against the anchor body 50 as the instrument 102 is withdrawn. The anchor body 50 is configured so that once it is deployed into the anatomical structure 1, the anchor body 50 can be expandable in the anatomical structure 1. In particular, the anchor body 50 can be expandable according to multiple modes of expansion, including at least first and second modes of expansion. For instance, the first mode of expansion can be defined by the iteration from the first configuration to the expanded configuration. The second mode of expansion can be defined by swelling of the anchor body 50 in response to exposure to an aqueous environment.

Referring now to FIGS. 1E and 1F, the actuation member 20 is configured to apply the actuation force, particularly a tensile force FT, to the anchor body 50 sufficient to actuate the anchor body 50 in the first mode of expansion from the first configuration C1 (FIG. 1E) to the expanded configuration C2 (FIG. 1F). In particular, in the first configuration C1, the anchor body 50 defines a first maximum thickness T1 along a respective second direction D2 that is angularly offset with respect to the respective direction of elongation D1 of the anchor body 50. When the anchor body 50 is in the expanded configuration C2, the anchor body 50 defines a second maximum thickness T2 along the second direction D2, and the second maximum thickness T2 is greater than the first maximum thickness T1. It is to be appreciated that the first and second maximum thicknesses T1 and T2 each refers to a total thickness of the anchor body 50 with respect to the respective second direction D2, and is not to be limited to thicknesses measured between two opposite points on the anchor body 50 that intersect a single, linear axis orientated along the second direction D2. For instance, the locations of the anchor body 50 that define a maximum thickness can be spaced from each other along the direction of elongation D1 of the anchor body 50. It should be appreciated that the first mode of expansion can occur in response to the application of the tensile force FT, for instance from the actuation member 20.

In the first mode of expansion, various regions of the anchor body 50 can "bunch together" (which action can also be referred to as "bunching") so as to achieve the second maximum thickness T2. The first mode of expansion can also be referred to as the "primary" mode of expansion, as it provides for primary fixation of the anchor body 50 in the target location of the anatomical structure 1. It is to be appreciated that, as used herein, the terms "bunch", "bunching", "bunch up", "bunch together", and their derivatives refers to an action whereby at least a portion of the anchor body 50 is caused to overlap itself along the second direction D2 that is angularly offset from the direction of elongation D1.

Referring now to FIGS. 1F and 1G, one or both of actuation member 20 and the anchor body 50 can be configured to swell in a manner causing the anchor 10 to transition from the expanded configuration C2 (FIG. 1F) to a further expanded configuration C3 (FIG. 1G). The further expanded position can also be referred to as a second expanded configuration C3 along the second direction D2. The anchor 10 can be configured to swell to the second expanded configuration C3 in response to exposition of one or both of the actuation member 20 and the anchor body 50 to an aqueous environment, such as the in vivo environment. In the further expanded configuration C3, the anchor body 50 defines a third maximum thickness T3, which is measured along the second direction D2, wherein the third maximum thickness T3 is greater than the second maximum thickness T2. Moreover, the inventors have observed that the actuation members 20 and/or the anchor bodies 50 of the present disclosure expand outwardly substantially in all directions extending from the geometric center of the anchor body 50 as the anchor 10 swells from the expanded configuration C2 to the further expanded configuration C3. It is to be appreciated that the second mode of expansion occurs more gradually and over a longer period of time than the first mode of expansion, and thus can provide secondary fixation of the anchor 10 in the target location of the anatomical structure 1.

Referring now to FIGS. 2A and 2B, the anchor body 50 comprises suture material, particularly textile suture material. The anchor body 50 can be constructed so as to define a substantially flat, tape-like geometry. In such embodiments, the anchor body 50 can be fabricated from flat braid, such as flat suture braid, that allows the anchor body 50 to be substantially flat when in a neutral configuration, and further allows the anchor body 50 to bunch together, such as into a ball-like structure, when the tensile force FT is applied by the actuation member 20. The anchor body 50 can define a length L1 measured along a longitudinal anchor direction LA that is oriented along a central axis 55 of the anchor body 50. The anchor body 50 can also define a thickness t measured along a transverse anchor direction TA, and a width W measured along a lateral anchor direction AA, wherein the longitudinal, transverse, and lateral anchor directions LA, TA, AA are perpendicular to each other. When the anchor body 50 is in the neutral configuration, the length L1 is preferably greater than the width W, and the width W is preferably greater than the thickness t. For instance, the width W can be several times greater than the thickness tin the neutral configuration. In such embodiments, the anchor body 50 can be characterized as having a flat, substantially planar structure, which can be folded or otherwise manipulated as necessary to form a three-dimensional anchor construct, alone or in combination with the actuation member 20. The anchor body 50 (which can also be referred to as a tape 65) includes a first end 51 and a second end 52 spaced from each other so as to define the length L1, which can be in a range from about 5.0 mm to about 100.0 mm. The anchor body 50 also extends from a first lateral edge 53 and a second lateral edge 54 spaced from each other so as to define the width W. The tape 65 also has a first side 57 and a second side 58 (which in the present embodiment are generally flat when the tape 65 is in the neutral configuration) spaced from each other along the transverse anchor direction TA so as to define the thickness t.

It is to be appreciated that the central axis 55 and the longitudinal anchor direction LA need not be straight and will both be determined by the present path along which the anchor body 50 extends. When the anchor body 50 is folded or otherwise manipulated into a non-neutral configuration (e.g., causing the central axis 55 and longitudinal anchor direction LA to be non-straight), the anchor body 50 can define a total thickness (e.g., T1-T3) that is greater than thickness t. Furthermore, as described above, the anchor body 50 is further configured to transition (such as by actuation via the actuation member 20) from the first configuration C1 to the expanded configuration C2 responsive to tension applied to the actuation member 20, which increases the total thickness of the anchor body 50 along the transverse anchor direction TA. It should be appreciated that the tape's 65 construction provides significant advantages in relation to anchor manufacturability. For example, the flat geometry allows the actuation member 20 to be stitched or spliced through the tape 65 more easily. The tape 65 can be a flexible, flat-braid suture material, including an ultra-high-molecular-weight polyethylene (UHMWPE) flat braid, (such as a 100% UHMWPE flat braid, such as PERMATAPE™ available from DePuy Synthes Mitek Sports Medicine), or another tape-like flexible material.

Figure 2F:
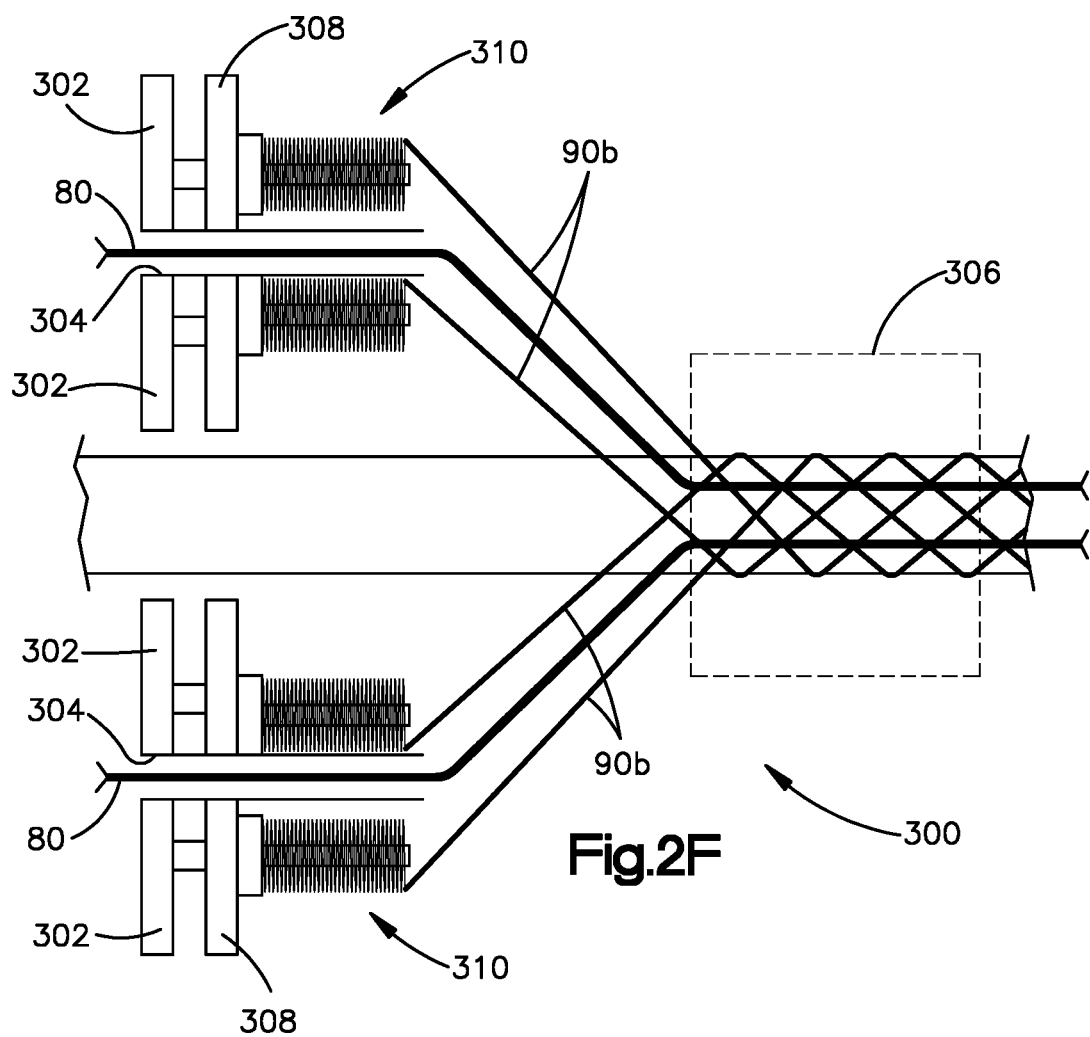
FIG. 2F is a system diagram of an apparatus for constructing anchor bodies constructed according to the embodiments illustrated in FIGS. 1A-B and FIGS. 1E-7.

Referring now to FIGS. 2C-2G, embodiments of the anchor body 50 will be described in which the anchor body 50 is also configured to swell in an aqueous environment. In such embodiments, the anchor body 50 can swell along the transverse anchor direction TA. When the anchor body 50 is configured as a swellable tape 65, the tape 65 can be a woven, knit, or braided structure that surrounds and encloses a material that provides the swelling functionality. For example, as shown in FIGS. 2B-2D, the swellable tape 65 can include at least one core structure 80 that extends parallel with the central axis 55. Each core structure 80 defines a central core axis 82 that can extend substantially parallel with the central axis 55 of the swellable tape 65. Thus, the at least one core structure 80 can be referred to as an "axial core" 80 or simply a "core" 80.

As shown in FIG. 2E, the at least one core 80 can be configured to swell along a radial direction R perpendicular to its core axis 82 in response to exposure of the at least one core 80 to an aqueous environment. The core 80 preferably includes a highly-elastic polymeric thread 84 that is incorporated with one or more osmotically active substances (i.e., substances that take up water), which causes the core 80 to swell. The polymeric thread 84 can be a filamentary polymer material (of a type which is non-degradable, partially degradable, or completely degradable). For instance, the polymeric thread 84 can be configured as a thermoplastic elastomer (polyurethane, polyester), a cross-linked elastomer (silicone, polyurethane, elastin, collagen) or a gel (polyethylene glycol, alginate, chitosan). The osmotically active constituent can include one or both of a salt (NaCl) and tri-calcium phosphate (TCP, which also advantageously facilitates bony ingrown within the core), although other osmotic materials can be employed, such as other biocompatible inorganic salts and aqueous solutions thereof, calcium chloride, calcium carbonate, or organic osmotically active molecules can be used, for example low-molecular-weight polysaccharides, such as dextran. In one example, the core 80 comprises a silicone thread incorporated with fine salt crystals 86 and TCP. The amount of salt and TCP contained within the core 80 can be in a range of about 2 percent to about 40 percent by weight. It is to be appreciated that the polymer thread 84 can be extruded from a melt or from a solution, and the salt (NaCl) particles are preferably co-extruded or admixed to the polymer mass before extrusion. It is to be appreciated that the core 80 can be formed by other methods, such as molding, by way of non-limiting example.

It is to be appreciated that the osmotically active substances can also or alternatively be embedded in a biocompatible gel or hydrogel (for example from the group of alginates, chitosans or copolymers thereof, polyacrylates, polyethylene glycol, etc.). An effect whose action is comparable in principle to the osmotically active substances can also be achieved by sole use of hydrogels. According to Fick's laws, particular importance is attached to the membrane surrounding the swelling system, which membrane critically influences the kinetics of osmosis by virtue of its permeation and diffusion properties for $H_2O$, and also by virtue of its thickness. The membrane can of course be made up of several layers or can also be provided with stable or soluble diffusion-inhibiting layers. If hydrogels are used, such a membrane-like property can also be achieved by means of a crosslinking density that increases considerably toward the outside. The concentration differences effecting osmosis are to be achieved between thread core and surrounding blood or interstitial and/or intrastitial fluid of the patient. It is to be appreciated that in embodiments where hydrogels are employed in the manner described above, such hydrogel-membrane structures can also be referred to as axial cores 80.

It is to be appreciated that the swellable tape 65 can include a single core 80 or, as shown in FIGS. 2C and 2D, more than one core 80, such as two, three, four, five, six, seven, eight, or more than eight axial cores 80. In embodiments in which the swellable tape 65 includes a single core 80, the core 80 preferably extends along the central axis 55 or at least extends along a winding pattern that intersects the central axis 55 at one or more locations. In other single-core embodiments, the core 80 can be offset from the central axis 55 and can extend parallel to the central axis 55. In embodiments in which the swellable tape 65 includes more than one core 80, at least a first core 80 and a second core 80 can extend alongside the lateral edges 53, 54 of the swellable tape 65 so as to be remote from the central axis 55. Alternatively, one of the cores 80 in a multi-core 80 embodiment (or the core 80 of a single-core 80 embodiment) can extend along the central longitudinal axis 55. As shown in FIG. 2D, each core 80 can have a circular cross-sectional shape in a plane orthogonal to the core axis 82, although other cross-sectional shapes are within the scope of the present disclosure, such as non-circular, elliptical, square, rectangular, or irregular shapes, by way of non-limiting examples. In embodiments involving core(s) 80 having circular cross-sectional shapes, each such core 80 preferably has an initial (i.e., neutral or non-swollen) diameter D4 preferably in a range from about 0.004 inch (about 0.102 mm) to about 0.040 inch (about 1.016 mm). Additionally, each core 80 (regardless of shape) has a durometer (i.e., hardness) preferably in a range from about 20 A to about 90 A.

As shown in FIGS. 2C and 2D, the swellable tape 65 is constructed by weaving, knitting or braiding the one or more cores 80 together with a plurality of fibers 90. These fibers 90 can have a material composition that includes polyethylene terephthalate (PET), ultra-high-molecular-weight polyethylene (UHMWPE), polydioxanone (PDS), polypropylene (PP), and nylon, for example, and can be monofilament or multifilament fibers, and can be employed with or without colorants as desired. The swellable tape 65 can be constructed by a braiding mechanism, such as the "flat braider" 300 depicted schematically in FIG. 2F. The swellable tape 65 is preferably constructed such that a first plurality of fibers 90a are braided in a manner so as to surround the core 80 (or each core 80 individually in multi-core embodiments) with the braided fiber 90a, as shown in FIG. 2D. In this manner, the first plurality of fibers 90a can effectively define a jacket or sheath surrounding each of the one or more cores 80, such as shown in FIGS. 2D-2E. The first plurality of fibers 90a are preferably pre-braided around each of the one more cores 80. Subsequently, with reference to FIG. 2F, one or more of the cores 80 having their pre-braided jackets 90a can be advanced as one or more respective "axial" threads through a carrier frame 302 (such as through respective tubes or channels 304 in the frame 302) and toward a convergence zone 306 of the braiding mechanism 300. The carrier frame 302 is configured to support a plurality of carriers 308, such as horn gears, for example, that collectively define bobbin pathways. A second plurality of fibers 90b are carried by a plurality of bobbins 310, which are loaded onto the carriers 308. Thus, the second plurality of fibers 90b can be referred to as carrier fibers 90b. When activated, the carriers 308 move the bobbins 310 along the bobbin pathways that are collectively configured to define the braiding pattern of the mechanism. In this manner, the one or more axial cores 80 can be advanced through the channels to bypass the frame 302 and will thereafter be braided together in interconnecting fashion via the second plurality of fibers 90b being unspooled from the bobbins. As shown in FIG. 2D, upon completion of the braiding process for multi-core embodiments, the cores 80 are preferably interconnected and laterally aligned with one another within the tape structure 50, such that each core 80 can be intersected by a single linear axis 88 that extends perpendicularly to any of the central core axes 82 and/or the central tape axis 55 when the swellable tape 65 is in the neutral configuration. It is to be appreciated that the fiber jackets 90b surrounding each core 80 are optional and need not be included for the swellable tape 65 to perform advantageously.

Figure 2G:
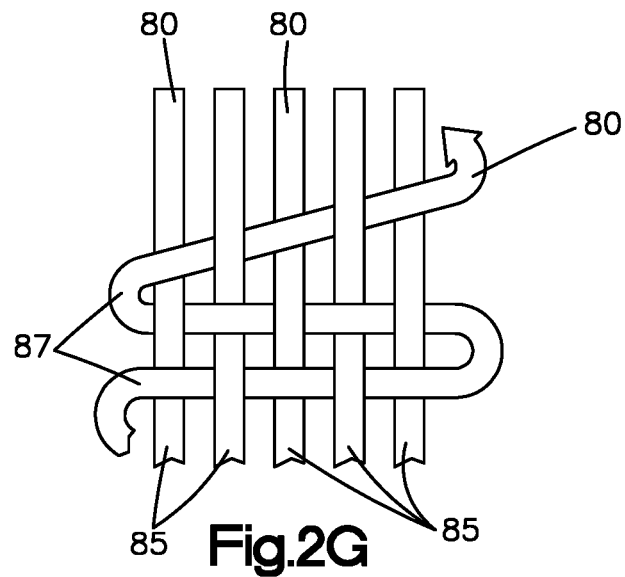
FIG. 2G is a plan view of a weave pattern that can be employed for constructing the anchor body, according to a yet additional embodiment of the present disclosure

It is to be appreciated that the braiding mechanism 300 can be a flat braiding mechanism and can be of a type that is commercially available, and can employ 4 to 50 carriers and 2 to 50 bobbins, the quantity of which can be selected depending on the particular desired braiding pattern. Additionally or alternatively, one or more cores 80 can be run through the braiding mechanism as carrier threads of fibers (i.e., some of the bobbins can be loaded with core 80), such that the one or more swellable cores 80 are included as interconnecting fibers within the swellable tape 65. Referring now to FIG. 2G, in yet other embodiments, the swellable tape 65 can be formed in a knit or woven pattern, such as a type employing warp and weft, as such terms are known in the textile industry. In such embodiments, core(s) 80 can be woven or knit as warp fibers or threads 85, as weft fibers of threads 87, or as warp and weft threads or fibers 85, 87. Optionally, all of the warp and weft threads or fibers 85, 87 can comprise core 80 threads.

The swellable tape 65 constructed as described above provides a number of advantages over prior art suture anchor bodies. The radial swelling capability (i.e., the second mode of expansion described above) enhances the anchor body 50 expansion within an anatomical structure 1, such as below a bone surface within a pre-drilled hole, for example, thereby increasing the anchor fixation strength. Furthermore, in embodiments including TCP within the core(s) 80, the TCP promotes bony ingrowth into the anchor body 50, which further increases the fixation strength and reduces the likelihood of micro-motion between the anchor body 50 and the anatomy in which it is anchored. It is to be appreciated that the tape's 65 construction also provides significant advantages in relation to anchor manufacturability. For example, as described above, the flat geometry allows the actuation member 20 to be stitched or spliced through the tape 65 more easily. Furthermore, in embodiments employing cores 80 extending alongside the lateral edges 53, 54 of the tape 65, the central portion of the tape 65 (i.e., along the central longitudinal axis 55) can have a pronounced geometry that further aids in stitching, piercing, or otherwise penetrating the tape 65 with the actuation member 20. For example, employing cores 80 extending alongside the lateral edges 53, 54 of the tape 65 and no cores 80 along the central axis 55 can advantageously provide the tape 65 with a longitudinally extending "trough" or "valley" along its central axis 55, which can allow the center of the tape 65 to be more quickly and accurately located, such as in a process that requires piercing the tape 65 with a needle carrying the actuation member 20, for example. In such processes, the trough or valley at the center of the tape 65 can prevent needle slippage or other unwanted results. It is to be appreciated that the trough or valley can provide both favorable visual guidance and mechanical positioning with respect to the tape 65. Additionally, employing cores 80 extending alongside the lateral edges 53, 54 of the tape 65 can also prevent the actuation member 20 from cutting, abrading, or otherwise damaging or reducing the structural integrity of the anchor body 50.

It is to be further appreciated that the tapes 65 having at least one swellable core 80 as described above provide a number of additional advantages over prior art anchor bodies, as well as over prior art sutures. For example, such swellable tapes 65 can be employed in a repair procedure as an anchor body that provides fixation, as a connecting suture that provides tension between structures, or as both an anchor body that provides fixation and a connecting suture that provides tension, as desired according to the particular needs of the patient, for example. Thus, in some embodiments, the swellable tape 65 can be employed as a suture interconnecting an anatomical structure with any other type of anchor, such as the HEALIX™ or HEALIX ADVANCE™ anchors available from DePuy Synthes Mitek Sports Medicine, by way of non-limiting example. In such embodiments, the ability of the swellable tape 65 to contract axially over time responsive to exposure to an aqueous environment can advantageously avoid or reduce the laxity observed in prior art sutures, and can also provide enhanced, lasting anatomical reduction in a repair, thus creating a more stable healing environment. The unique design and functionality of the swellable tape 65 renders it useful across a wide variety of surgical applications.

Figure 3D:
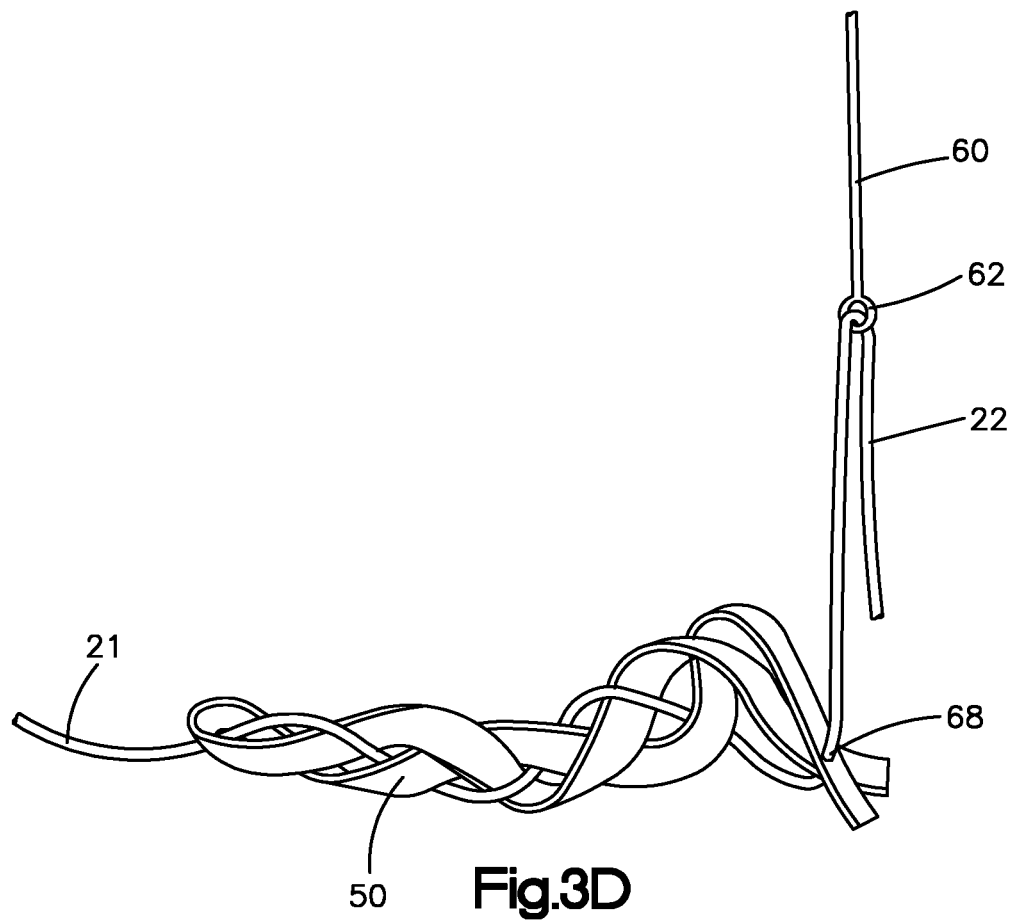

With reference to FIGS. 3A-E, an example method of constructing the anchor 10 with the tape 65 will now be described. It should be appreciated that the tape 65 according to the present embodiment can optionally be swellable when exposed to an aqueous environment, though the tape 65 need not have such swellability. To form the anchor 10 according to one example method, the anchor body 50 can be penetrated, as shown in FIG. 3A, so as to define a first penetration 56 in the tape 65, such as by being pierced with a needle 60 having an eyelet 62 in which the actuation member 20 is threaded. It is to be emphasized that, as used herein, the terms "pierce" and "penetrate" and their respective derivatives refer expressly to an action by which an object (e.g., a needle) performs each of the following: 1) enters the tape 65 itself from one of the ends 51, 52, edges 53, 54, sides 57, 58 (which includes an interface between any of 51, 52, 53, 54, 57, 57); 2) advances through the tape 65 itself; and 3) exits the tape 65 itself from one of the ends 51, 52, edges 53, 54, or sides 57, 58 (which includes an interface between any of 51, 52, 53, 54, 57, 57) thereof. The terms "pierce" and "penetrate" and their respective derivatives does not refer to an action by which an object merely extends through: 1) a loop or eyelet or other such structure defined by a folded or analogously manipulated portion of the anchor body 50, or 2) a pre-existing structure defined by the anchor body 50, such as a bifurcation, aperture, hole, or other such structure.

After or concurrently with the penetrating or piercing step, the actuation member 20 can be advanced through the first penetration 56 so that the actuation member 20 extends through the tape 65 from one of the sides 57, 58 to the other of the sides 57, 58. Preferably, the first penetration 56 is located at a longitudinal midpoint between the ends 51, 52. The first penetration 56 is also preferably located at or substantially near a width-midpoint between edges 53, 54. In embodiments where the tape 65 includes one or more swellable members (e.g., cores 80) extending longitudinally along or near one or both of the edges 53, 54 or otherwise spaced from the central axis 55, locating the first penetration at or near a width-midpoint has the benefit of avoiding piercing a swellable member. The tape 65 can be folded at the first penetration 56, such as along a fold axis 59 substantially perpendicular to the longitudinal axis 25 of the actuating member 20 coincident with the first penetration 56. It is to be appreciated that the free longitudinal portions of the anchor body 50 on either side of the first penetration 56 can be referred to as first and second anchor body "limbs" or "tails" 64, 66.

Figure 3E:
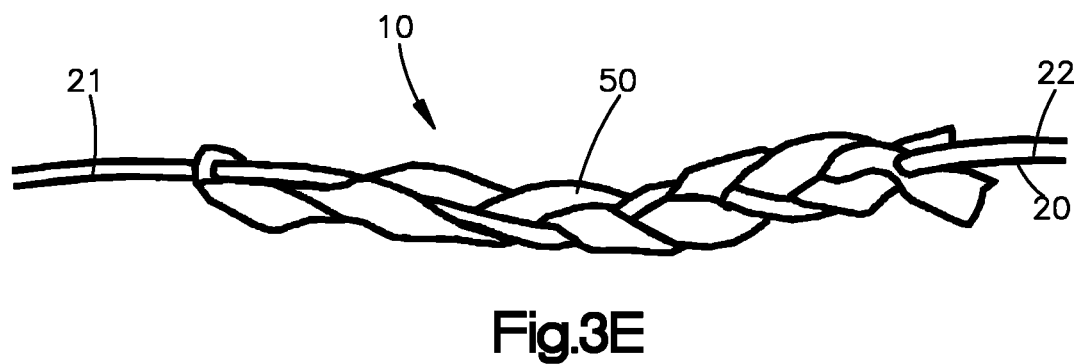

As shown in FIG. 3B, the anchor body 50 can be braided together with the actuation member 20 so as to form a braided suture anchor 10. In particular, the anchor tails 64, 66 can be braided together with the actuation member 20 in a simple, three-member alternating braid (which can also be referred to as a "simple three-strand braid"). As shown in FIG. 3C, the second anchor tail 66 can optionally be folded over the actuation member 20 and brought to bear against the first anchor tail 64 at a bearing point or pinch point, and one or both of the first and second anchor tails 64, 66 can optionally be pierced with the needle 60 at an additional or second penetration 68. For example, in some embodiments, both of the first and second anchor tails 64, 66 can be pierced at the second penetration 68 (which can be characterized as a joint penetration 68) at the pinch point. In such embodiments, as shown in FIGS. 3D-E, the needle 60, having the actuation member 20 threaded through the eyelet 62, can be advanced along with the actuation member 20 through the joint penetration 68 until the actuation member 20 is pulled cleanly through the second penetration 68. The second penetration 68 (including embodiments where the second penetration 68 is a joint penetration 68) is configured to prevent, inhibit, or at least reduce the likelihood of the braided suture anchor 10 from unraveling. It is to be appreciated that the anchor body 50 can be braided together with the actuation member 20 utilizing only the first penetration 56, or optionally without any penetrations of the actuation member 20 through the anchor body 50, so as to form a braided suture anchor 10.

Further, the remaining portions of the anchor tails 64, 66 (i.e., those portions extending from the braided suture anchor 10) can be cut or otherwise trimmed to avoid obstruction with the completed braided suture anchor 10, which is depicted in FIG. 3E. The cut or trimmed ends of the anchor body tails 64, 66 can be further stitched, crimped, fused or melted (such as with a heat-tipper), bonded (such as with a settable adhesive), or otherwise subjected to a finishing process to prevent the ends from fraying or otherwise weakening. The braided structure of the suture anchors 10 of the present embodiment, as well as the actuation member 20 only passing through one, two, or three penetrations 56, 68 of the anchor body 50 (i.e., three if you consider that the second penetration 68 jointly penetrates both tails 64, 66), or optionally no penetrations of the anchor body 50, allows the actuation member 20 to slide substantially freely (i.e., with minimal, negligible, or marginal resistance) through the anchor body 50, even after the anchor body 50 has been actuated into the expanded configuration C2. Thus, it can also be said that the anchor body 50 of the present embodiment is freely slidable along the actuation member 20. Furthermore, the braided structure of the anchor 10 provides that, as the anchor is actuated from the first configuration C1 to the expanded configuration C2, the anchor body 50 will bunch together in a more uniform manner throughout the entire anchor body 50 relative to prior art braided suture anchors. While not being bound to a particular theory, the inventors believe that the aforementioned more uniform bunching results primarily from consistent interlacing (i.e., "braiding" in the current embodiment) of the anchor body 50 and the actuation member 20. Referring again to FIG. 1F, the braided suture anchor 10 of the present embodiment has been observed to exhibit a more cylindrical-like bunched configuration (i.e., expanded configuration C2) after deployment than other suture anchors.

With reference to FIGS. 4A-4K, another example method of constructing a braided suture anchor 10 with the tape 65 and the actuation member 20 will now be described. As in the example described above, the suture anchor 10 of the present embodiments is configured such that the anchor body 50 is substantially freely slidable along the actuation member 20, before and after transitioning to the expanded configuration C2. Thus, it can also be said that the actuation member 20 of the present embodiment is substantially freely slidable through the anchor body, before and after transitioning to the expanded configuration C2. It should be appreciated that the tape 65 according to the present embodiment can optionally be swellable when exposed to an aqueous environment, though the tape 65 need not have such swellable functionality.

Figure 4A:
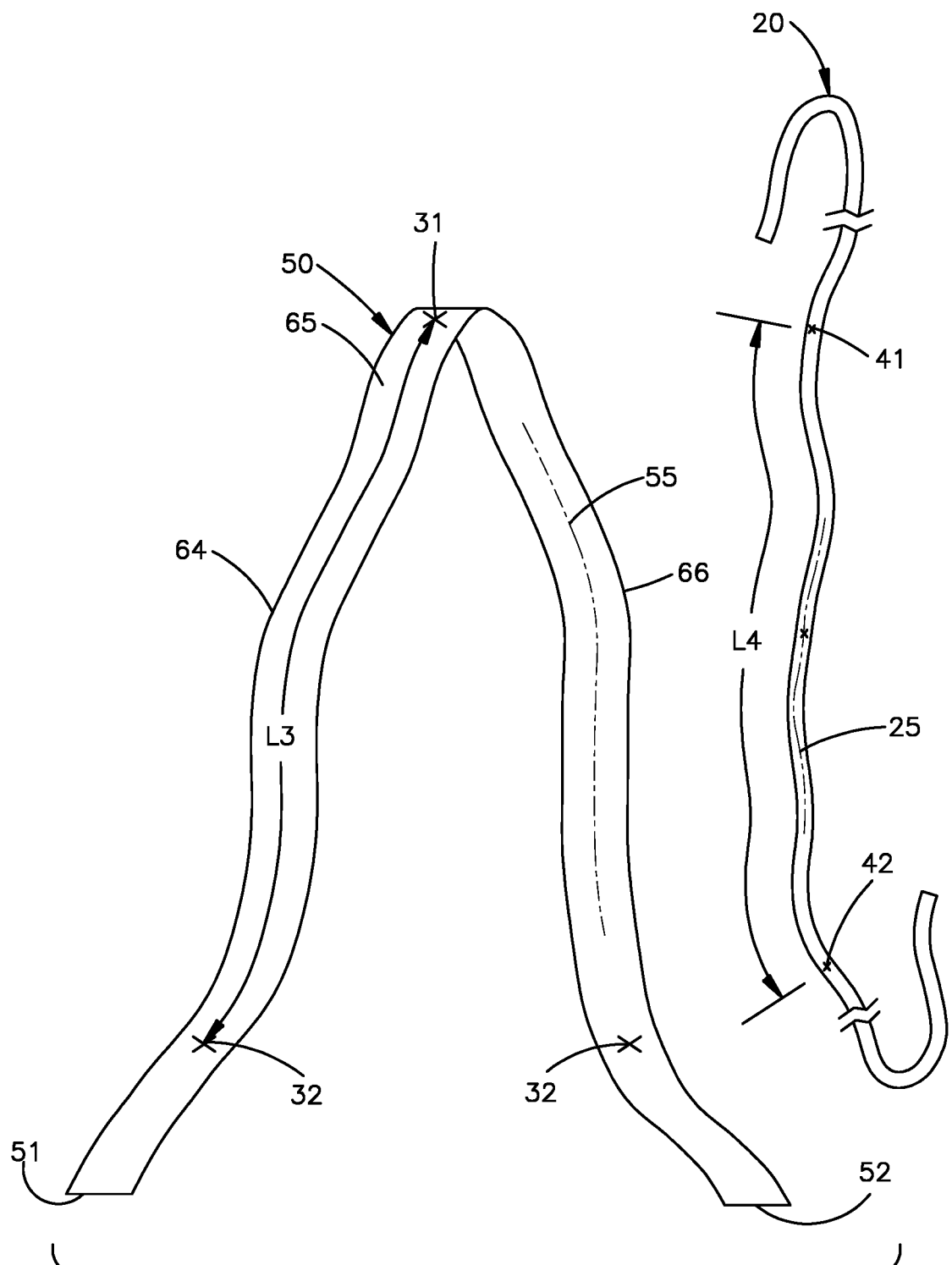

Referring now to FIG. 4A, the anchor body 50 can be a tape 65 having a length L1 (see FIG. 2A), which can be predetermined and which can be in a range of about 20 mm to about 120 mm, more particularly in a range of about 40 mm to about 100 mm, and preferably in a range of about 50 mm to about 70 mm. It should be appreciated that construction of the anchor 10 can optionally commence with a continuous, uncut length of anchor body 50, such as a length unwound from a spool or other storage configuration. The width W of the tape 65 can be in a range of about 0.5 mm to about 5.0 mm, more particularly in a range of about 1.0 mm to about 3.0 mm, and preferably in a range of about 1.3 mm to about 2.7 mm. The actuation member 20 preferably has a swellable core 80, as described above. The actuation member 20 defines an overall length, as measured along its longitudinal axis 25, that can be in a range of about 18 inches to about 48 inches, and preferably about 36 inches.

One or both of the anchor body 50 and the actuation member 20 can be marked to provide one or more reference points for use in constructing the suture anchor 10 according to one or more specified parameters, such as length. For example, an operator can mark the anchor body 50 at a first location 31 preferably at a longitudinal midpoint 31*a* of the anchor body 50 along the central axis 55. The first location 31 can also be at a width-midpoint between the edges 53, 54 of the anchor body 50.

The operator can also mark the anchor body 50 at a pair of second locations 32 which, in the illustrated example, are equidistantly spaced from the first location 31 by a distance L3 as measured along the central axis 55. Distance L3 represents the target design length of the anchor 10 being constructed according to the present example. The operator can further mark the actuation member at a first location 41 and a second location 42 that are spaced from each other by distance L4, as measured along the longitudinal axis 25 of the actuation member 20. In the present example, distance L4 is substantially equivalent to distance L3 and thus also represents the target design length of the anchor 10. Distances L3 and L4 will effectively determine the length L5 of the finished suture anchor 10 formed according to the present example (see FIG. 4J). Distances L3 and L4 can be in a range of about 10 mm to about 68 mm, more particularly in a range of about 20 mm to about 45 mm, and preferably in a range of about 26 mm to about 30 mm.

Figure 4B:
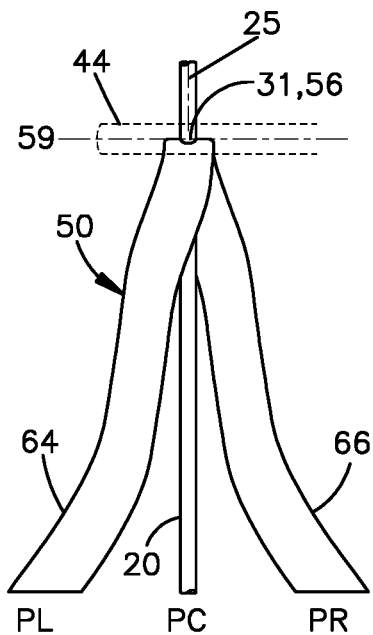

Referring now to FIG. 4B, the operator can penetrate the actuation member 20 through the anchor body 50 at the first location 31, thereby forming the first penetration 56 at the first location 31. Preferably, the operator advances the actuation member 20 through the first penetration 56 until the first location 42 of the actuation member 20 is aligned with the first location 31 of the anchor body 50. The operator can fold the anchor body 50 at the first penetration 56, such as along a fold axis 59 substantially perpendicular to the longitudinal axis 25 of the actuating member 20 coincident with the penetration 56 (i.e., at the first location 31). The operator can clamp the anchor body 50 and actuation member 20 together at the first location 31, such as with a clamp 44, thereby maintaining the relative positions of the anchor body 50 and the actuation member 20 at the first location 31. The clamp 44 is preferably configured to clamp the anchor body 50 and the actuation member 20 together precisely at the first penetration 56 and preferably defines a clamp width that is about 2.0 mm or less as measured along the longitudinal axis 25 of the actuation member 20 (and/or along the central axis 55 of the anchor body 50) so as to not disrupt braiding adjacent the clamp 44. It should be appreciated that the first location 31 defines a first end 31*b* of a braided suture anchor construct 30 formed according to the subsequent steps of the present example. As used herein, the term "suture anchor construct" refers to an anchor 10 that includes the anchor body 50 and the actuation member 20 in a pre-finalized or otherwise intermediate phase of construction, formation, fabrication, or manufacture. The first end 31*b* of the braided suture anchor construct 30 can also define a first end 11 of the completed anchor 10.

It should further be appreciated that the braiding steps discussed below refer to "crosses" or "picks", each cross or pick meaning an instance in which one of the braid elements of the suture anchor construct 30 (i.e., the actuation member 20 or the anchor body 50) crosses another one of the braid elements. More specifically, in the present example, each cross or pick refers to an instance in which one of the first anchor body tail 64, second anchor body tail 66, and actuation member 20 crosses another one of the first anchor body tail 64, second anchor body tail 66, and actuation member 20. The clamped portion of the anchor body 50 and actuation member 20 effectively defines a "start" of the braided suture anchor construct 30, from which crosses or picks can be formed. As shown, the braid elements of the suture anchor construct 30 (i.e., the anchor body tails 64, 66 and the actuation member 20) can be characterized as extending away from the first location 31 toward one of a left position PL, a center position PC, and a right position PR with respect to each other. In the illustrated example of the start, the first anchor body tail 64 extends to the left position PL, the actuation member 20 extends to the center position PC, and the second anchor body tail 66 extends to the right position PR. The subsequent crosses or picks can be characterized with respect to the left, center, and right positions PL, PC, PR. In particular, the picks in the present example are each described as starting from the center position PC and crossing over to either the left or right position PL, PR, which can be characterized as a "center-to-outside" pick description. It should be appreciated that in other embodiments, the picks can each be described as starting from either the left or right position PL, PR and crossing over to the center position PC, which can be characterized as an "outside-to-center" pick description. In the present example, the picks are enacted on the anchor body tails 64, 66 and the actuation member 20 according to a simple three-strand braid pattern. Moreover, the present example shown in FIGS. 4A-5K is a nineteen-pick (P1-P19) design, although the braided suture anchor construct 30 can have more or fewer than nineteen picks P19. It should also be appreciated that one or more of the marking steps described above can be performed after applying the clamp 44 to the first location 31. For example, the operator can mark the second locations 32, 42 of the anchor body tails 64, 66 and the actuation member 20, respectively after clamping the first location 31.

Figure 4C:
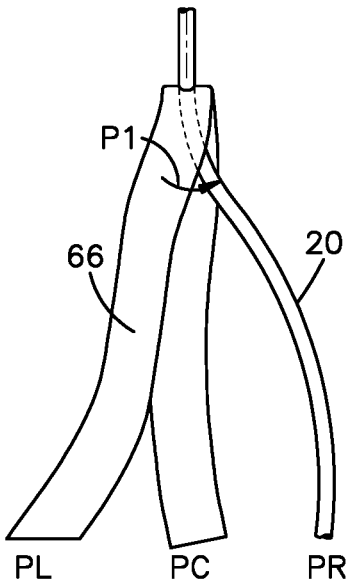
Figure 4D:
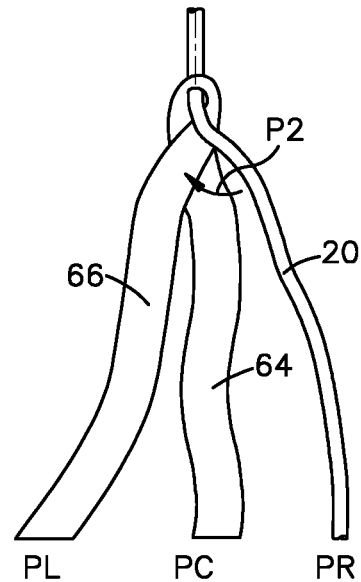
Figure 4E:
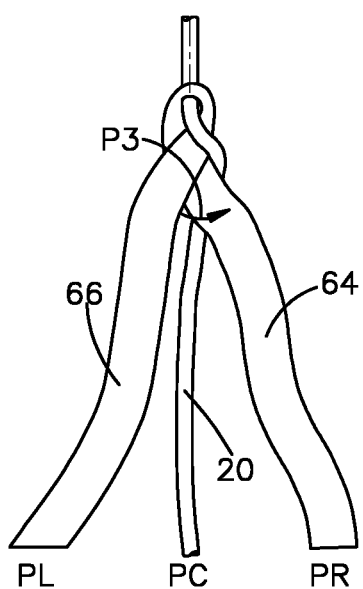
Figure 4F:
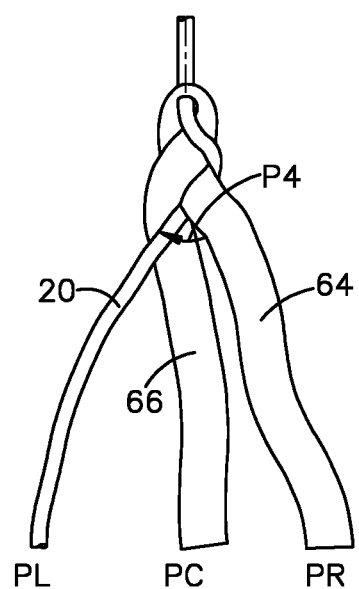
Figure 4G:
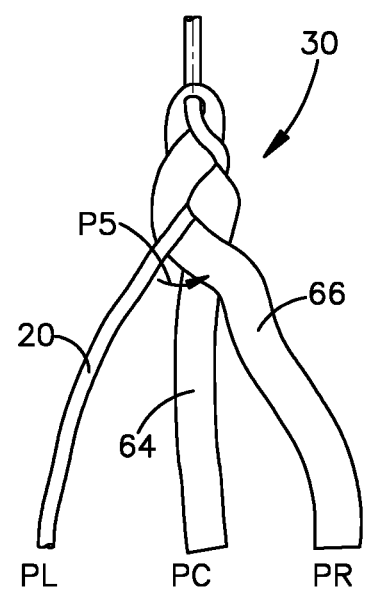

As shown in FIG. 4C, to begin the braiding process, the operator can cross the actuation member 20 over the second anchor body tail 66, from the center position PC to the right position PR, thereby defining the first pick P1. As shown in FIG. 4D, the operator can cross the second anchor body tail 66 over the first anchor body tail 64, from the center position PC to the right position PR, thereby defining the second pick P2. As shown in FIG. 4E, the operator can cross the first anchor body tail 64 over the actuation member 20, from the center position PC to the right position PR, thereby defining the third pick P3. As shown in FIG. 4F, the operator can cross the actuation member 20 over the second anchor body tail 66, from the center position PC to the left position PL, thereby defining the fourth pick P4. As shown in FIG. 4G, the operator can cross the second anchor body tail 66 over the first anchor body tail 64, from the center position PC to the right position PR, thereby defining the fifth pick P5.

Referring now to FIG. 4H, the operator can continue constructing the braided suture anchor construct 30 in similar fashion by sequentially performing the following crosses (each beginning from the center position PC): crossing the first anchor body tail 64 over the actuation member 20 (to the left position PL) to define the sixth pick P6, crossing the actuation member 20 over the second anchor body tail 66 (to the right position PR) to define the seventh pick P7, crossing the second anchor body tail 66 over the first anchor body tail 64 (to the left position PL) to define the eight pick P8, crossing the first anchor body tail 64 over the actuation member 20 (to the right position PR) to define the ninth pick P9, crossing the actuation member 20 over the second anchor body tail 66 (to the left position PL) to define the tenth pick P10, crossing the second anchor body tail 66 over the first anchor body tail 64 (to the right position PR) to define the eleventh pick P11, crossing the first anchor body tail 64 over the actuation member 20 (to the left position PL) to define the twelfth pick P12, crossing the actuation member 20 over the second anchor body tail 66 (to the right position PR) to define the thirteenth pick P13, crossing the second anchor body tail 66 over the first anchor body tail 64 (to the left position PL) to define the fourteenth pick P14, crossing the first anchor body tail 64 over the actuation member 20 (to the right position PR) to define the fifteenth pick P15, crossing the actuation member 20 over the second anchor body tail 66 (to the left position PL) to define the sixteenth pick P16, crossing the second anchor body tail 66 over the first anchor body tail 64 (to the right position PR) to define the seventeenth pick P17, crossing the first anchor body tail 64 over the actuation member 20 (to the left position PL) to define the eighteenth pick P18, and crossing the actuation member 20 over the second anchor body tail 66 (to the right position PR) to define the nineteenth pick P19.

Referring now to FIG. 4I, with the nineteenth pick P19 formed, the operator can prepare to attach the actuation member 20 to the first and second anchor body tails 64, 66 at the second locations 32 thereof so as to form a second end 32b of the braided anchor body construct 30, which can also define a second end 12 of the completed anchor 10. In the present example, the operator also prepares to cause the second location 42 of the actuation member 20 to substantially coincide with the second locations 32 of the anchor body tails 64, 66. To prepare for such attachment, the operator can position the second anchor body tail 66 over the first anchor body tail 64 so as to align the second locations 32 of the anchor body tails 64, 66 with each other. The operator can also thread the actuation member 20 through the eyelet 62 of a needle 60 and penetrate the needle 60 through the first and second anchor body tails 64, 66 at the second location 32, thereby creating a second penetration 68 at the second location 32. The operator advances the needle 60 through the second penetration 68 until the actuation member 20 is pulled cleanly through the joint penetration 68. As described above, because the second penetration 68 of the present embodiment extends through both of the first and second anchor body tails 64, 66, the second penetration 68 can be characterized as a joint penetration. The first suture tail 21 can be said to extend away from the braided suture anchor construct 30 from the first end 31b thereof, and the second suture tail 22 can be said to extend away from the braided suture anchor construct 30 from the second end 32b thereof (i.e., from the second penetration 68).

Referring now to FIG. 4J, at the second penetration 68 (i.e., at the second location 32), the actuation member 20 preferably penetrates the first and second anchor body tails 64, 66 from the sides 57, 58 thereof over which the actuation member 20 crosses at the nineteenth pick P19 to and through the opposite sides 57, 58 thereof. The second location 32 defines the second end 32b of the braided suture anchor construct 30. The braided suture anchor construct 30 has a length L5 measured between the first and second ends 31b, 32b thereof along a central axis 35 of the braided suture anchor construct 30. The length L5 can be in a range of about 10 mm to about 60 mm, more particularly in a range of about 20 mm to about 30 mm, and preferably in a range of about 23 mm to about 27 mm. It should be appreciated that the first and second ends 31b, 32b of the braided suture anchor construct 30 correspond to first and second ends 11, 12 of the completed suture anchor 10. Similarly, the central axis 35 of the braided suture anchor construct 30 also defines a central axis of the completed suture anchor 10. Accordingly, the central axis 35 can also be referred to as the central axis of the anchor 10.

As described above with reference to the embodiment shown in FIG. 3E, the remaining portions of the anchor tails 64, 66 extending from the second location 32 to their respective ends 51, 52 can be cut or otherwise trimmed to avoid obstruction with the completed braided suture anchor construct 30. The trimmed anchor body tails 64, 66 can have a trimmed length L6 measured from the penetration 68 to the respective ends 51, 52. The trimmed length L6 is preferably in a range of about 0.5 mm to about 4 mm, although other trimmed lengths L6, including lengths shorter than 0.5 mm and longer than 4 mm, are within the scope of the embodiments described herein, including lengths between 0 mm and 0.5 mm. The cut or trimmed ends of the anchor body tails 64, 66 can be further stitched, crimped, fused or melted (such as with a heat-tipper), bonded (such as with a settable adhesive), or otherwise subjected to a finishing process to prevent the ends from fraying or otherwise weakening. Furthermore, any of the foregoing finishing processes can be employed to attach the trimmed ends 51, 52 together, to enhance structural integrity at the second end 32b of the braided suture anchor construct 30 and to further prevent obstruction with the construct 30 during use.

It should be appreciated that, instead of penetrating the actuation member 20 through the anchor body 50 at the first location 31, the anchor body 50 can be folded or wrapped around the actuation member at the first location 31, and the anchor body tails 64, 66 can otherwise be braided together with the actuation member 20 from the first location 31 to the second location 32.

Figure 4M:
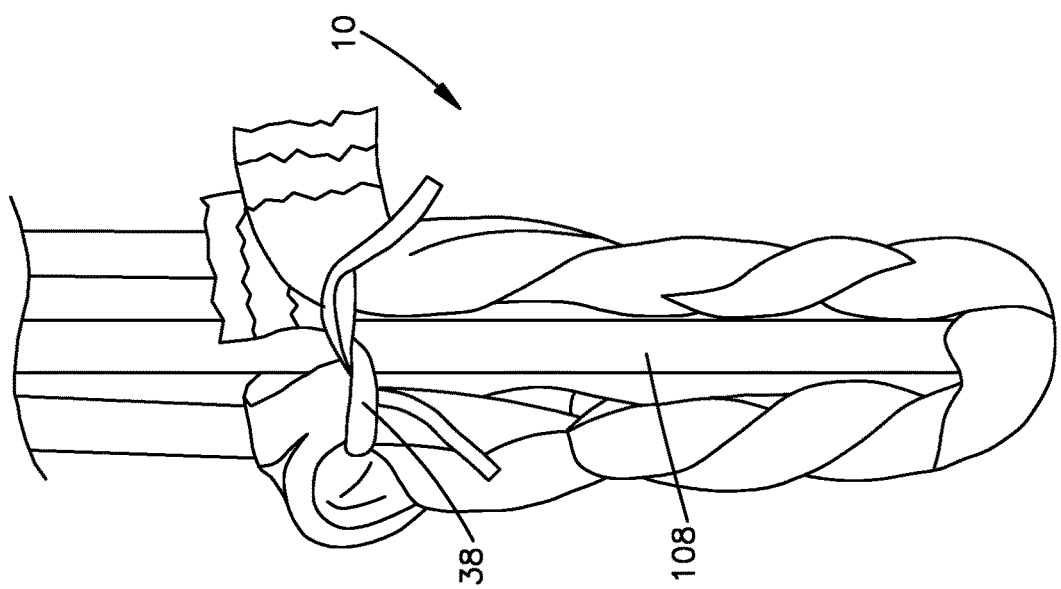
FIGS. 4L-M are opposite side elevation views of the anchor illustrated in FIG. 4K having a band interconnecting folded ends of the anchor, according to an embodiment of the present disclosure.
Figure 4L:
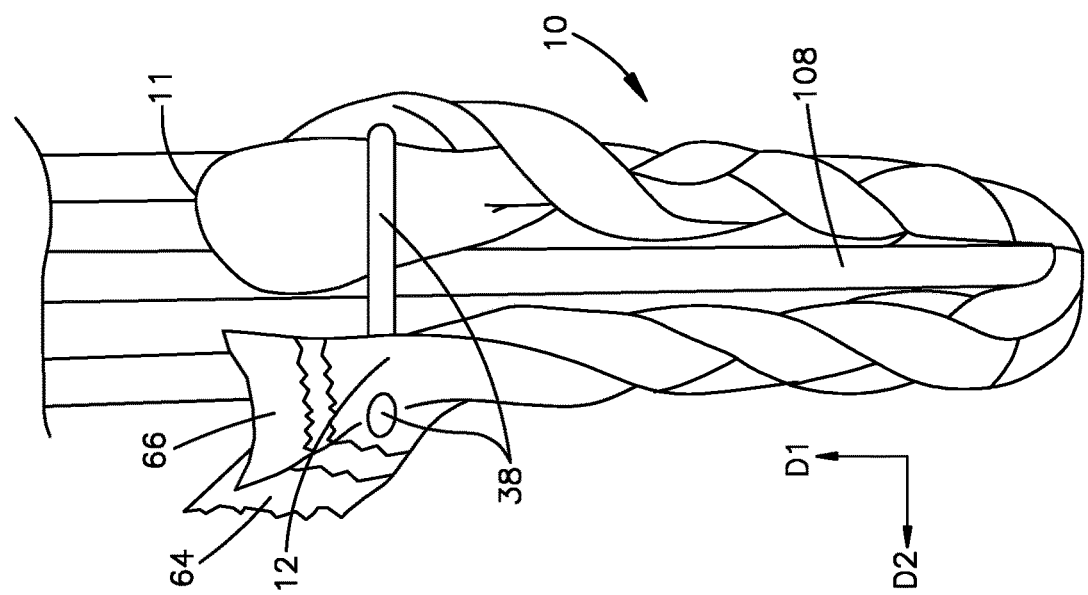
Figure 4K:
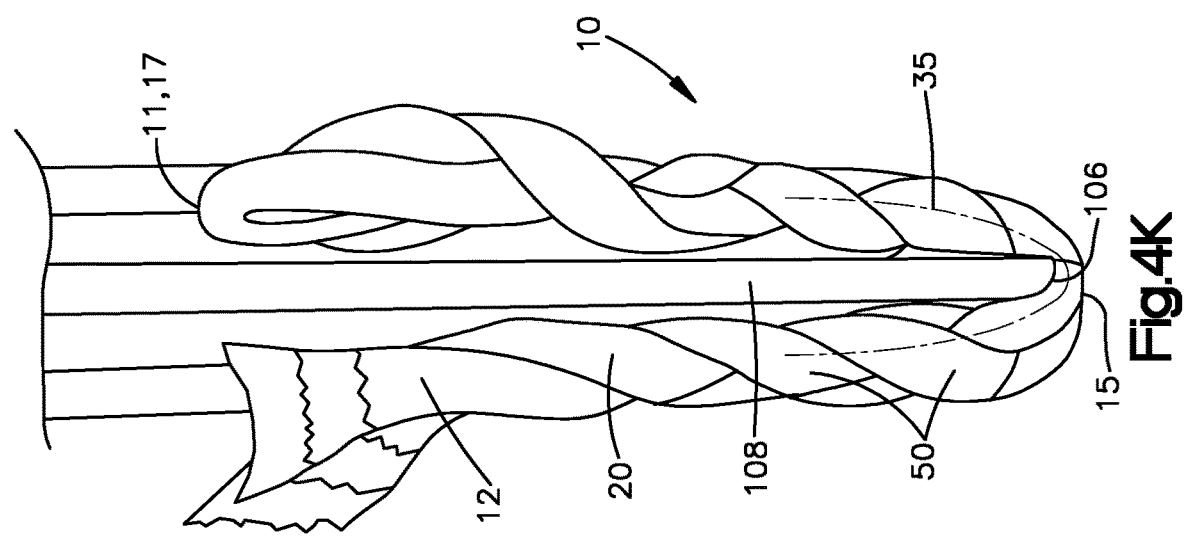
FIG. 4K is a side elevation view the anchor constructed according to the steps illustrated in FIGS. 4A-J loaded onto an insertion instrument.

Referring now to FIG. 4K, the anchor 10 can be folded or bent, such as into a U-shape or a V-shape, which can facilitate loading the anchor 10 onto and/or within an insertion instrument, such as onto the distal tip 108 of the insertion instrument 102 described above. As shown, the anchor 10 can be bent such that the distal end 106 of the instrument 102 engages the anchor 10 at an apex of the bend, which is located substantially at an axial midpoint of the anchor 10 (i.e., substantially halfway between the first and second ends 11, 12 of the anchor 10 along its central axis 35).

Referring now to FIGS. 4L and 4M, a connecting member 38 can be attached to the anchor 10 at or near the first and second ends 11, 12 thereof, thereby interconnecting or otherwise coupling the first and second ends 11, 12 of the anchor 10 together with respect to a second direction D2 that is angularly offset with respect to the direction of elongation D1. As shown, the second direction D2 can be substantially perpendicular to the direction of elongation D1. The connecting member 38 can be a band, which can penetrate through the anchor body 50, such as through one or both of the first and second anchor body tails 64, 66, at or near each of the first and second ends 11, 12 of the anchor 10. The connecting band 38 can extend substantially entirely around the anchor 10, such as by wrapping around the anchor 10 substantially along the second direction D2. The connecting band 38 can be tied together or otherwise interconnected with itself. The connecting band 38 can be constructed of any kind of implantable suture material, such as a flexible biocompatible material, which can also be nonabsorbable. Such band materials include, by way of non-limiting examples, ultra-high-molecular-weight polyethylene (UHMWPE), nylon, polypropylene, polydioxanone (PDS) (such as ORTHOCORD™), polyester suture materials, such as polyethylene terephthalate (PET), particularly 4-0 suture size ETHIBOND® brand polyethylene terephthalate, produced by Ethicon US, LLC, headquartered in Bridgewater, N.J. The inventors have observed that the presence of the connecting band 38 at the proximal end 17 of the anchor 10 favorably enhances retention of the anchor 10 on the insertion instrument 102 prior to deployment within the target location of the anatomical structure 1. It should be appreciated that characteristics of the connecting band 38 can be tailored as necessary to enhance retention on the instrument 102 and/or fixation within the target location.

Figure 4O:
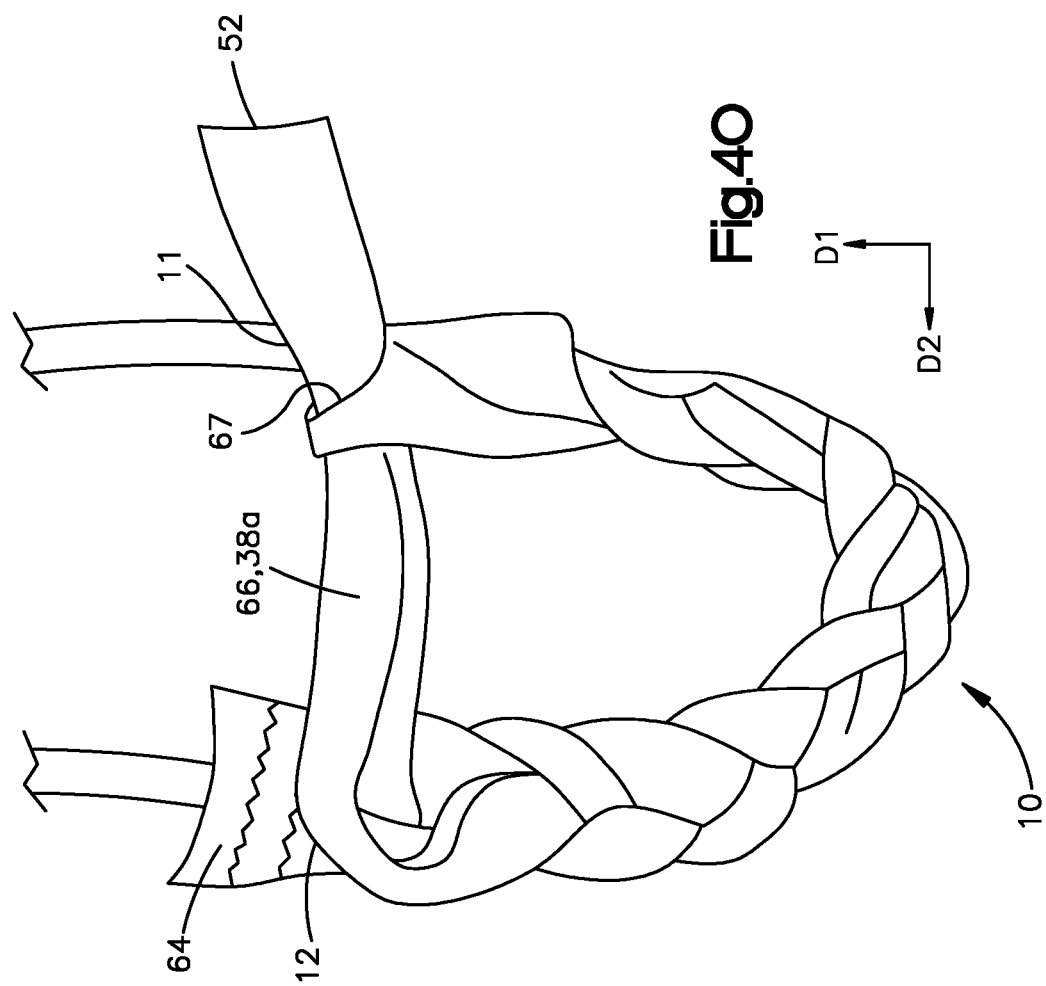
FIG. 4O is a side elevation view of the anchor illustrated in FIG. 4M loaded onto an insertion instrument.
Figure 4N:
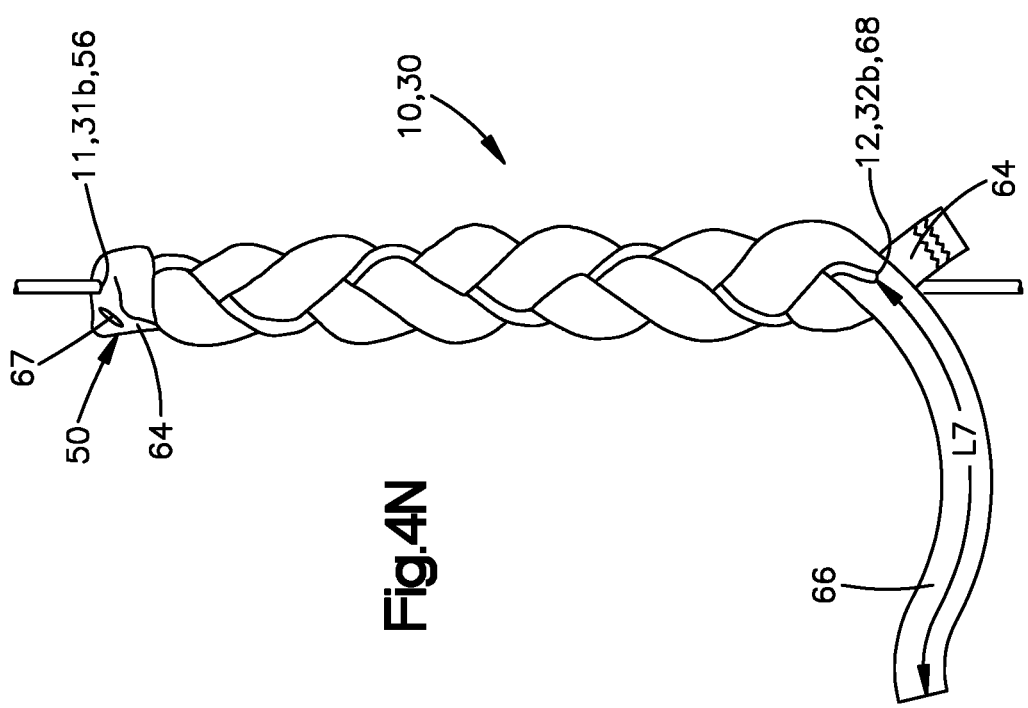
FIG. 4N is a front elevation view of an intermediate step of constructing an anchor having a connecting member for interconnecting ends of the anchor, according to another embodiment of the present disclosure.

Referring now to FIGS. 4N and 4O, an alternative connecting member 38*a* for connecting the first and second ends 11, 12 of the anchor 10 will now be described. As shown in FIG. 4N, the suture anchor 10 can be constructed according to the steps described above with reference to FIGS. 4A-4J, except that one of the anchor body tails 64, 66 can define the connecting member 38*a*, which extends a distance L7 beyond the second location 32 (and thus also beyond the second penetration 68) that is greater than the trimmed length L6 of the other anchor body tail 66, 64. It should be appreciated that although the illustrated example shows the second anchor body tail 66 as defining the connecting member 38*a*, the first anchor body tail 64 can define the connecting member 38*a* in other embodiments. The anchor body 50 can be penetrated at a third penetration 67 located adjacent the first location 31.

As shown in FIG. 4O, the braided suture anchor construct 30 can be folded or bent for loading onto the distal tip 108 of the insertion instrument, such that the second end 12 of the anchor 10 extends toward the first end 11 of the anchor 10. The connecting member 38*a* can extend from the second end 12 and through the third penetration 67, thereby connecting the first and second ends 11, 12 of the anchor 10. As above, the connecting member 38*a* interconnects or otherwise couples the first and second ends 11, 12 of the anchor 10 together with respect to a second direction D2 that is angularly offset with respect to (such as substantially perpendicular to) the direction of elongation D1 of an instrument upon which the anchor 10 is to be loaded. In the present embodiment, the connecting member 38*a* will extend across a single side of the distal tip 108 of the instrument 102. Before or after loading the anchor 10 of the present embodiment onto and/or within the insertion instrument, the connecting member 38*a* can be cinched to decrease the distance between the first and second ends 11, 12 of the anchor 10 along the second direction D2 as needed. Additionally, before or after loading the anchor 10 onto and/or within the insertion instrument, the free end 52 of the connecting member 38*a* can be cut or otherwise trimmed. Similarly to the connecting band 38 described above, the inventors have observed that the presence of the anchor body tail 66 forming the connecting member 38*a* of the present embodiment favorably enhances retention of the anchor 10 on the insertion instrument 102 prior to deployment within the target location of the anatomical structure 1. It should be appreciated that characteristics of the connecting member 38*a* can be tailored as necessary to enhance retention on the instrument 102 and/or fixation within the target location.

With reference to FIGS. 5A-5K, an example method of constructing a braided suture anchor 10 from the actuation member 20 and the anchor body 50 so that the anchor body 50 defines a connecting member that connects the first and second ends 11, 12 of the anchor 10 will now be described. As in the example embodiments described above, the suture anchor 10 of the present embodiments is configured such that the anchor body 50 is substantially freely slidable along the actuation member 20, before and after transitioning to the expanded configuration C2. Thus, it can also be said that the actuation member 20 of the present embodiment is substantially freely slidable through the anchor body, before and after transitioning to the expanded configuration C2. It should be appreciated that the tape 65 according to the present embodiment can optionally be swellable when exposed to an aqueous environment, though the tape 65 need not have such swellable functionality.

Figure 5A:
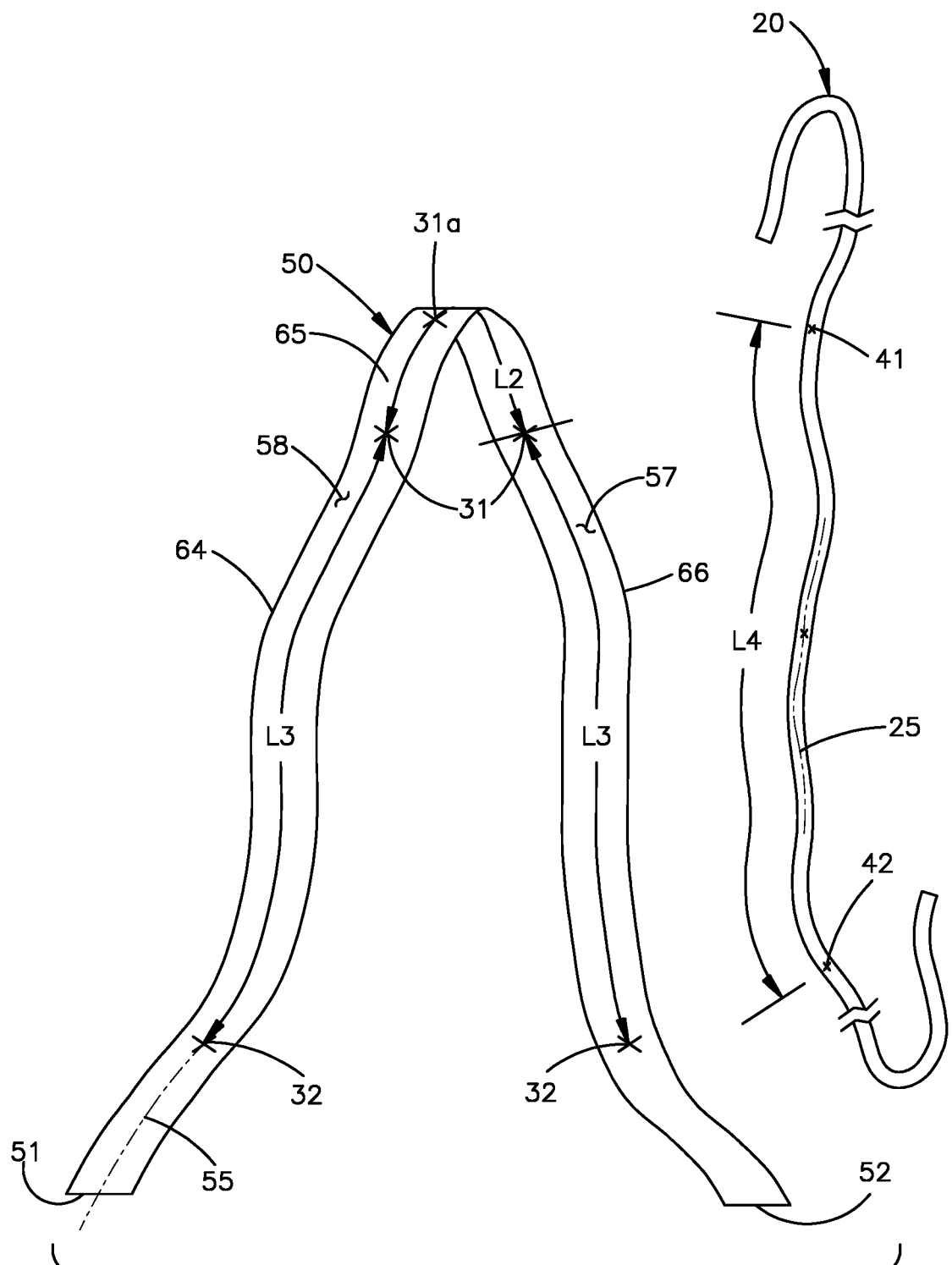

Referring now to FIG. 5A, the anchor body 50 can be a tape 65 having a length L1, which can be predetermined and which can be in a range of about 20 mm to about 130 mm, more particularly in a range of about 40 mm to about 105 mm, and preferably in a range of about 50 mm to about 70 mm. As described above, construction of the anchor 10 can optionally commence with a continuous, uncut length of anchor body 50. The width W of the tape 65 can be in a range of about 0.5 mm to 5.0 mm, more particularly in a range of about 1.0 mm to about 3.0 mm, and preferably in a range of about 1.3 mm to about 2.7 mm. The actuation member 20 preferably has a swellable core 80 and has an overall length, as measured along its longitudinal axis 25, in a range of about 18 inches to about 48 inches, and preferably about 36 inches.

One or both of the anchor body 50 and the actuation member 20 can be marked to provide one or more reference points for use in constructing the suture anchor 10 according to one or more specified parameters, such as length. For example, an operator can mark the anchor body 50 at a pair of longitudinally spaced locations 31, which can individually or collectively be referred to as a first location 31. In the illustrated example, the pair of first locations 31 are spaced from each other at a distance L2 as measured along the central axis 55 of the anchor body 50. It should be appreciated that the pair of first locations 31 can optionally be spaced equidistantly from a longitudinal midpoint 31*a* of the anchor body 50 along the central axis 55. Thus, in such embodiments, one of the first locations 31 is located on the first anchor body tail 64 and the other of the first locations 31 is located on the second anchor body tail 66. Moreover, in such embodiments, the pair of first locations 31 will be equidistantly spaced from the first and second ends 51, 52 of the first and second anchor body tails 64, 66. The longitudinal midpoint 31*a* of the anchor body 50 can also be marked for reference in constructing the suture anchor 10, regardless of whether the pair of first locations 31 are equidistant from the longitudinal midpoint 31*a*.

The operator can also mark the anchor body 50 at a pair of second locations 32 which, in the illustrated example, are equidistantly spaced from the respective first locations 31 by a distance L3 as measured along the central axis 55. Accordingly, the first and second locations 31, 32 on the first anchor body tail 64 are spaced from each other by distance L3, and the first and second locations 31, 32 on the second anchor body tail 64 are also spaced from each other by distance L3, which represents the target design length of the anchor 10 being constructed according to the present example. The operator can further mark the actuation member at a first location 41 and a second location 42 that are spaced from each other by distance L4, as measured along the longitudinal axis 25 of the actuation member 20. In the present example, distance L4 is substantially equivalent to distance L3 and thus also represents the target design length of the anchor 10. Distances L3 and L4 will effectively determine the length L5 of the finished suture anchor 10 formed according to the present example (see FIG. 5J). As in the example described above, distances L3 and L4 can be in a range of about 10 mm to about 68 mm, more particularly in a range of about 20 mm to about 45 mm, and preferably in a range of about 26 mm to about 30 mm.

Figure 5B:
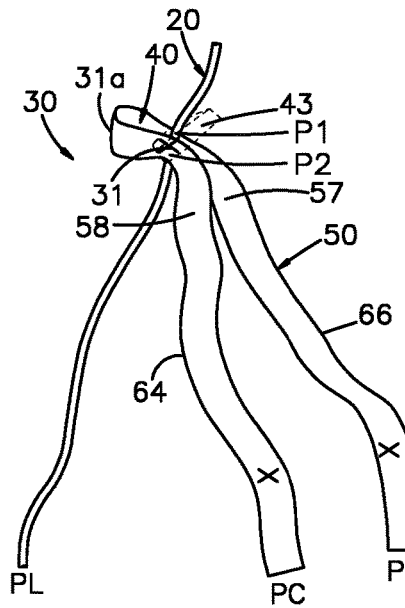

Referring now to FIG. 5B, a portion of the anchor body 50 can be folded, preferably by doubling the anchor body 50 over itself such that a select one of the first and second sides 57, 58 (the first side 57 shown in FIG. 5A) is brought into contact with itself at the pair of first locations 31, thereby forming a pinch point at which the pair of first locations 31 collectively effectively define a singular first location 31 of the anchor body 50 from which a loop 40 extends. Thus, once formed, the loop 40 can define an apex at the longitudinal midpoint 31a of the anchor body 50 along the central axis 55. The loop 40 has a length along the central axis 55 that is defined by distance L2. The operator can position the actuation member 20 between the pinched portion of the anchor body 50, particularly such that the actuation member 20 is positioned between the select side 57, 58 of the anchor body 50 at the pinch point 31. Preferably, the actuation member 20 is positioned such that the first location 41 of the actuation member substantially coincides with the first location 31 of the anchor body 50. The operator can clamp the pinched anchor body 50 and actuation member 20 together at the first location 31, such as with a clamp 44, thereby maintaining the structure of the loop 40 and the relative positions of the anchor body 50 and the actuation member 20 at the first location 31. It should be appreciated that the first location 31 defines a first end 31b of a braided suture anchor construct 30 formed according to the present example. The first end 31b of the braided suture anchor construct 30 can also define a first end 11 of the completed anchor 10.

In the present example, the picks will be described as starting from either the left or right position PL, PR and crossing over to the center position PC, which, as mentioned above, can be characterized as an "outside-to-center" pick description. At the first location 31, the actuation member 20 crossing over the second anchor body tail 66 can be characterized as the first pick P1, and the anchor body 50 being folded such that the first anchor body tail 64 crosses over the actuation member 20 at the first location 31 can be characterized as the second pick P2 of the braided suture anchor construct 30 formed according to the present example. The first and second picks P1, P2 cause the first and second anchor body tails 64 and the actuation member 20 to extend away from the first location 31 such that the actuation member 20 extends to the left position PL, the first anchor body tail extends to the center position PC, and the second anchor body tail 66 extends to the right position PR. From these relative positions, the subsequent picks can be enacted on the anchor body tails 64, 66 and the actuation member 20 according to a simple three-strand braid pattern. The present example shown in FIGS. 5A-5K is a nineteen-pick design (P1-P19), although the braided suture anchor construct can have more or fewer than nineteen picks P19.

It should also be appreciated that the one or more of the marking steps described above can be performed after the loop 40 is formed, and also after the actuation member 20 is positioned at the pinch point. For example, the anchor body 50 can be folded to define the loop 40 having the desired length, the first and second anchor body tails 64, 66 can be pinched together, and the actuation member 20 can be positioned between the anchor body tails 64, 66 at the pinch point, as described above. From this configuration, the operator can mark the first location 31 on the construct, such as on the second side 58 (i.e., the outward facing side) of the anchor body 50. With the first location 31 marked, the operator can measured the desired lengths L3, L4 on the anchor body tails 64, 66 and the actuation member 20 and mark the second locations 32, 42 accordingly. Other options for marking the construct for assistance in forming the braided suture anchor construct 30 are within the scope of the embodiments described herein.

Figure 5C:
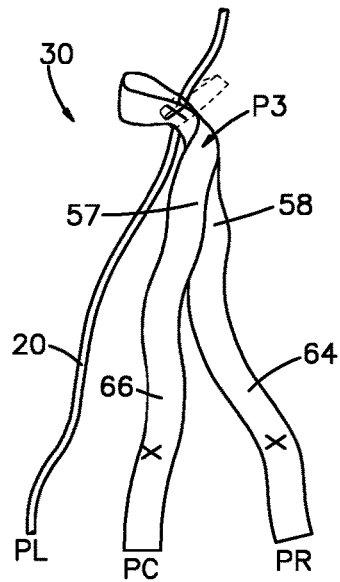
Figure 5D:
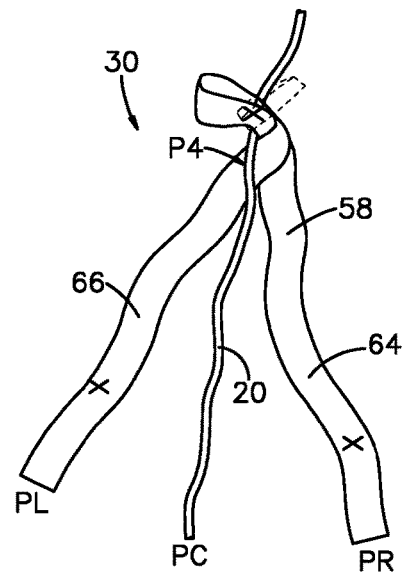
Figure 5E:
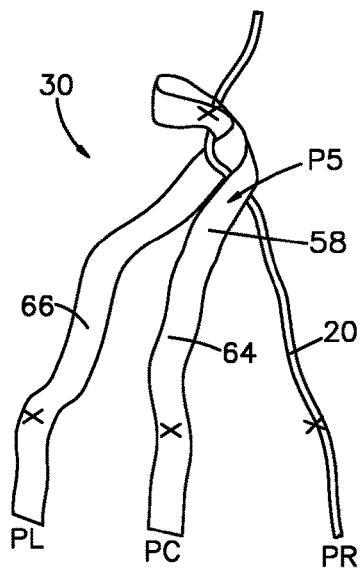
Figure 5F:
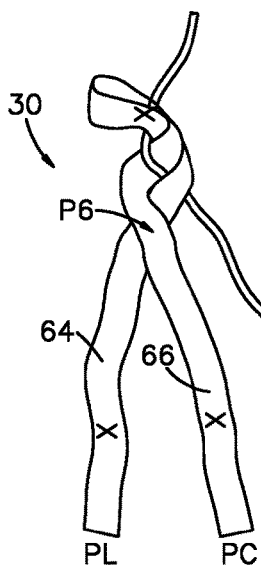
Figure 5G:
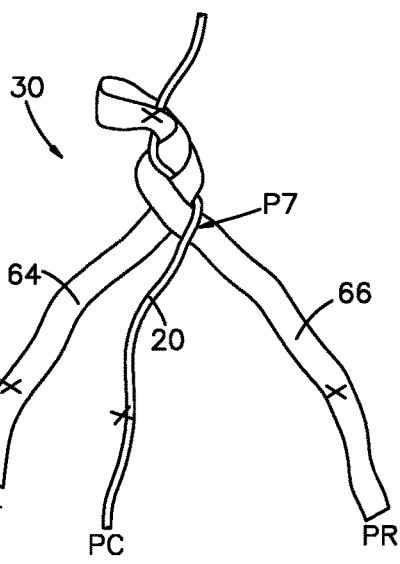

As shown in FIG. 5C, the second anchor body tail 66 can be folded over the first anchor body tail 64 from the right position PR to the center position PC, thereby defining the third pick P3. In this instance, "folding" the second anchor body tail 66 over the first anchor body tail 64 means that the first side 57 of the second anchor body tail 66 contacts the second side 58 of the first anchor body tail 64 at the third pick P3. Thus, as shown, the second sides 58 of both of the first and second anchor body tails 64, 66 are visible downstream of the third pick P3. As shown in FIG. 5D, the actuation member 20 can be crossed over the second anchor body tail 66 (from the left position PL to the center position PC), thereby defining the fourth pick P4. As shown in FIG. 5E, the first anchor body tail 64 can be crossed over the actuation member 20 (from the right position PR to the center position PC), thereby defining the fifth pick P5. In this example, the first anchor body tail 64 can cross over the actuation member 20 without folding, that is to say, the first anchor body tail 64 crosses over the actuation member 20 such that the same side (the second side 58) of the first anchor body tail 64 is visible in FIG. 5E immediately upstream and downstream of the fifth pick P5. The example shown in FIGS. 5A-5J can involve one of the anchor body tails 64, 66 being folded only at the third pick P3, with the subsequent anchor body tail picks P5-6, P8-9, P11-12, P14-15, and P17-18 involving crosses without folds. However, it should be appreciated that one or more and up to all of these subsequent anchor body tail picks can involve folding the respective anchor body tail 64, 66. As shown in FIG. 5F, the second anchor body tail 66 can be crossed over the first anchor body tail 64 (from the left position PL to the center position PC), thereby defining the sixth pick P6. As shown in FIG. 5G, the actuation member 20 can be crossed over the second anchor body tail 66 (from the right position PR to the center position PC), thereby defining the seventh pick P7.

Figure 5I:
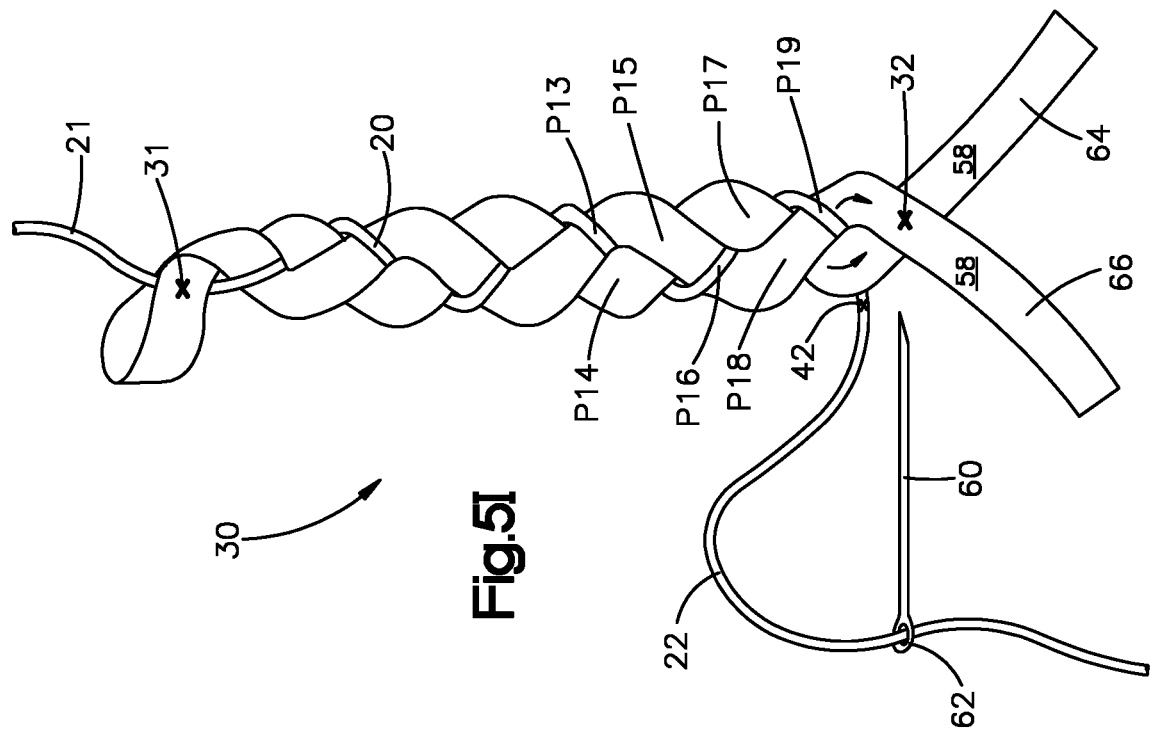
Figure 5H:
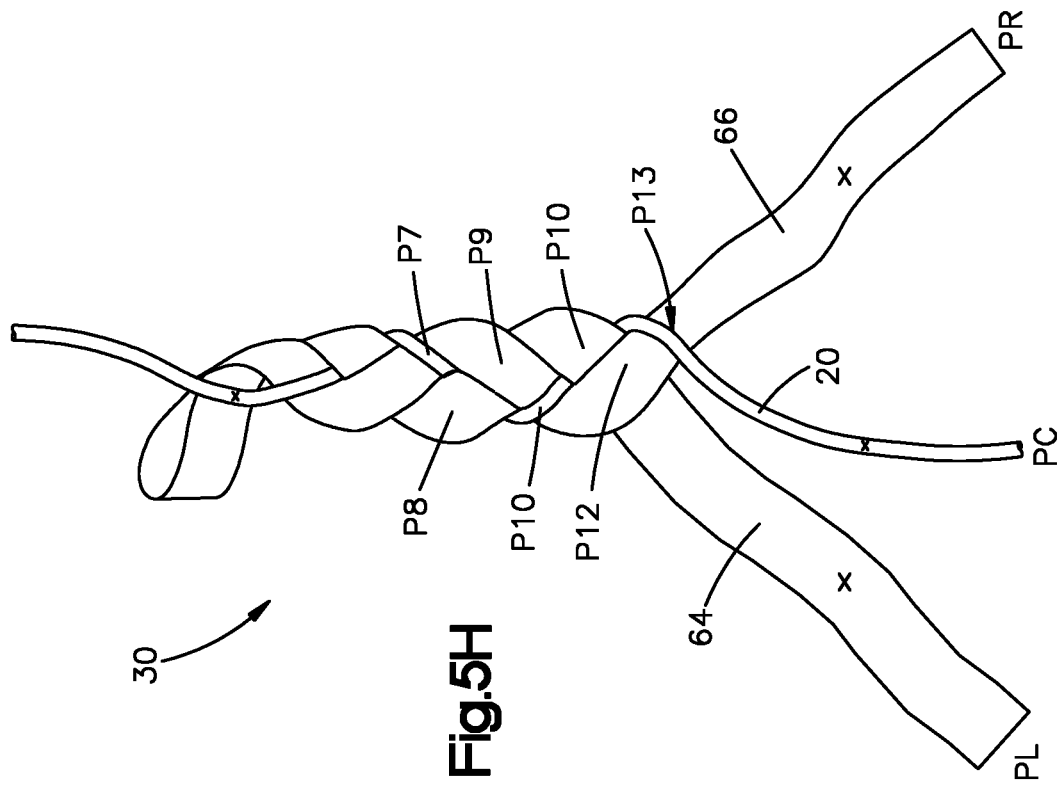

Referring now to FIG. 5H, the operator can continue constructing the braided suture anchor construct 30 in similar fashion by sequentially: crossing the first anchor body tail 64 over the actuation member 20 to define the eight pick P8, crossing the second anchor body tail 66 over the first anchor body tail 64 to define the ninth pick P9, crossing the actuation member 20 over the second anchor body tail 66 to define the tenth pick P10, crossing the first anchor body tail 64 over the actuation member 20 to define the eleventh pick P11, crossing the second anchor body tail 66 over the first anchor body tail 64 to define the twelfth pick P12, and crossing the actuation member 20 over the second anchor body tail 66 to define the thirteenth pick P13. As shown in FIG. 5I, the operator can further continue constructing the braided suture anchor construct 30 in similar fashion by sequentially: crossing the first anchor body tail 64 over the actuation member 20 to define the fourteenth pick P14, crossing the second anchor body tail 66 over the first anchor body tail 64 to define the fifteenth pick P15, crossing the actuation member 20 over the second anchor body tail 66 to define the sixteenth pick P16, crossing the first anchor body tail 64 over the actuation member 20 to define the seventeenth pick P17, crossing the second anchor body tail 66 over the first anchor body tail 64 to define the eighteenth pick P18, and crossing the actuation member 20 over the second anchor body tail 66 to define the nineteenth pick P19.

With continued reference to FIG. 5I, with the nineteenth pick P19 formed, the operator can prepare to attach the actuation member 20 to the first and second anchor body tails 64, 66 at the second locations 32 thereof so as to form a second end 32b of the braided anchor body construct 30, which can also define a second end 12 of the completed anchor 10. In the present example, operator also prepares to cause the second location 42 of the actuation member 20 to substantially coincide with the second locations 32 of the anchor body tails 64, 66. To prepare for such attachment, the operator can position the second anchor body tail 66 over the first anchor body tail 64 and can further align the second locations 32 of the anchor body tails 64, 66 with each other. The operator can also thread the actuation member 20 through the eyelet 62 of a needle 60 and penetrate the needle 60 through the first and second anchor body tails 64, 66 at the second location 32, thereby creating a second penetration 68 at the second location 32. The operator advances the needle 60 through the second penetration 68 until the actuation member 20 is pulled cleanly through the second penetration 68, which can be characterized as a joint penetration. The first suture tail 21 can be said to extend away from the braided suture anchor construct 30 from the first end 31b thereof, and the second suture tail 22 can be said to extend away from the braided suture anchor construct 30 from the second end 32b thereof (i.e., from the second penetration 68).

Referring now to FIG. 5J, at the second penetration 68, the actuation member 20 preferably penetrates the first anchor body tail 64 prior to penetrating the second anchor body tail 66. Stated differently with reference to FIG. 5J, the actuation member 20 penetrates the anchor body tails 64, 66 from the sides 57, 58 thereof not visible in FIG. 5J (i.e., sides 57) to and through the opposite sides 58, 57 thereof that are visible in FIG. 5J (i.e., sides 58). The braided suture anchor construct 30 has a length L5 measured between the first and second ends 31b, 32b thereof along the central axis 35 of the braided suture anchor construct 30. The length L5 can be within the ranges described above with reference to FIG. 4J of the above example. As above, the first and second ends 31b, 32b of the braided suture anchor construct 30 correspond to first and second ends 11, 12 of the completed suture anchor 10. Similarly, the central axis 35 of the braided suture anchor construct 30 also defines a central axis of the completed suture anchor 10.

As described above, the remaining portions of the anchor tails 64, 66 extending from the second location 32 to their respective ends 51, 52 can be cut or otherwise trimmed to avoid obstruction with the completed braided suture anchor construct 30. The trimmed anchor body tails 64, 66 can have a trimmed length L6 measured from the penetration 68 to the respective ends 51, 52. The trimmed length L6 is preferably in a range of about 0.5 mm to about 4 mm, although other trimmed lengths L6, including lengths shorter than 0.5 mm and longer than 4 mm, are within the scope of the embodiments described herein. The cut or trimmed ends of the anchor body tails 64, 66 can be further stitched, crimped, fused or melted (such as with a heat-tipper), bonded (such as with a settable adhesive), or otherwise subjected to a finishing process to prevent the ends from fraying or otherwise weakening. Furthermore, any of the foregoing finishing processes can be employed to attach the trimmed ends 51, 52 together, to enhance structural integrity at the second end 32b of the braided suture anchor construct 30 and to further prevent obstruction with the construct 30 during use. The first suture tail 21 can be said to extend away from the braided suture anchor construct 30 from the first end 31b thereof, and the second suture tail 22 can be said to extend away from the braided suture anchor construct 30 from the second end 32b thereof. The second suture tail 22 can be directed through the loop 40, such that both of the first and second suture tails 21, 22 extend through the loop 40.

Figure 5L:
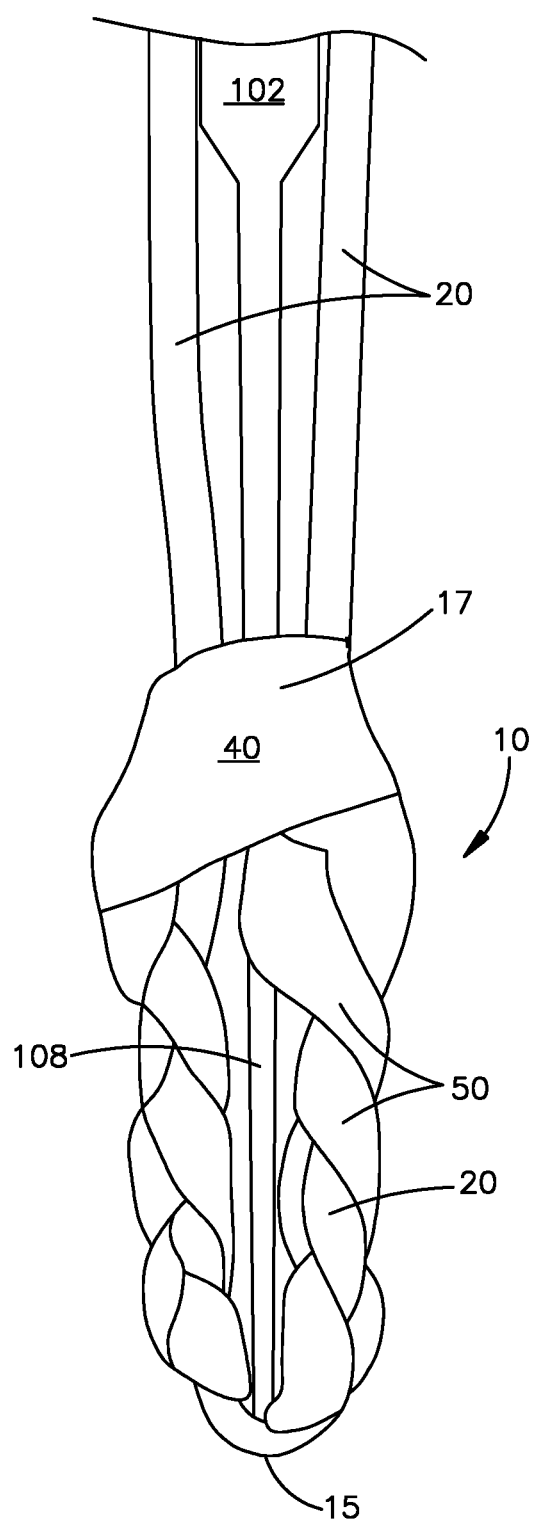
FIGS. 5L-M are opposite side elevation views of the anchor illustrated in FIG. 5K loaded onto an insertion instrument.
Figure 5M:
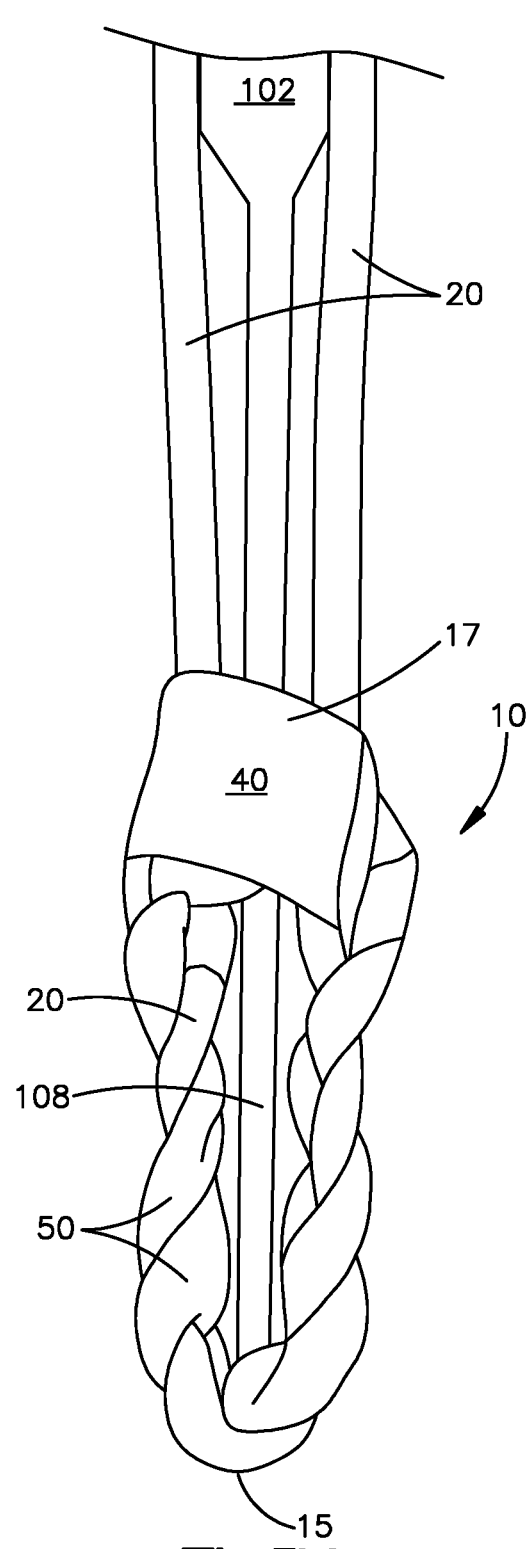

Referring now to FIG. 5K, to complete the suture anchor 10, the second suture tail 22 can be pulled through the loop 40 (and/or the loop 40 can be advanced along the second suture tail 22) until the second end 12 of the anchor 10 is positioned within the loop 40 or at least in close proximity to the loop 40. Thus, the loop 40 preferably surrounds the first and second ends 11, 12 of the anchor 10 thereby interconnecting or otherwise coupling the first and second ends 11, 12 of the anchor 10 together with respect to the second direction D2 that is angularly offset with respect to the direction of elongation D1. As shown, the second direction D2 can be substantially perpendicular to the direction of elongation D. The loop 40 can be characterized as a "closed" loop, and can also define the proximal end 17 of the anchor 10 constructed according to the present example. It should be appreciated that the act of bringing the second end 12 of the anchor 10 to the loop 40 also involves bending or folding the anchor 10, such as into a U-shape or a V-shape, which can facilitate loading the anchor 10 onto an insertion instrument 102. As shown in FIGS. 5L and 5M, the anchor 10 of the present embodiment can be loaded onto the instrument 102 by causing the distal tip 108 of the instrument 110 to advance through the loop 40 and into engagement with the braided anchor body 50. As shown, the loop 40 can extend entirely around the distal tip 108. The inventors have observed that the presence of the closed loop 40 at the proximal end 17 of the anchor 10 favorably enhances retention of the anchor 10 on the insertion instrument 102 prior to deployment within the target location of the anatomical structure 1. It should be appreciated that characteristics of the loop 40 can be tailored as necessary to enhance retention on the instrument 102 and/or fixation within the target location.

Figure 6B:
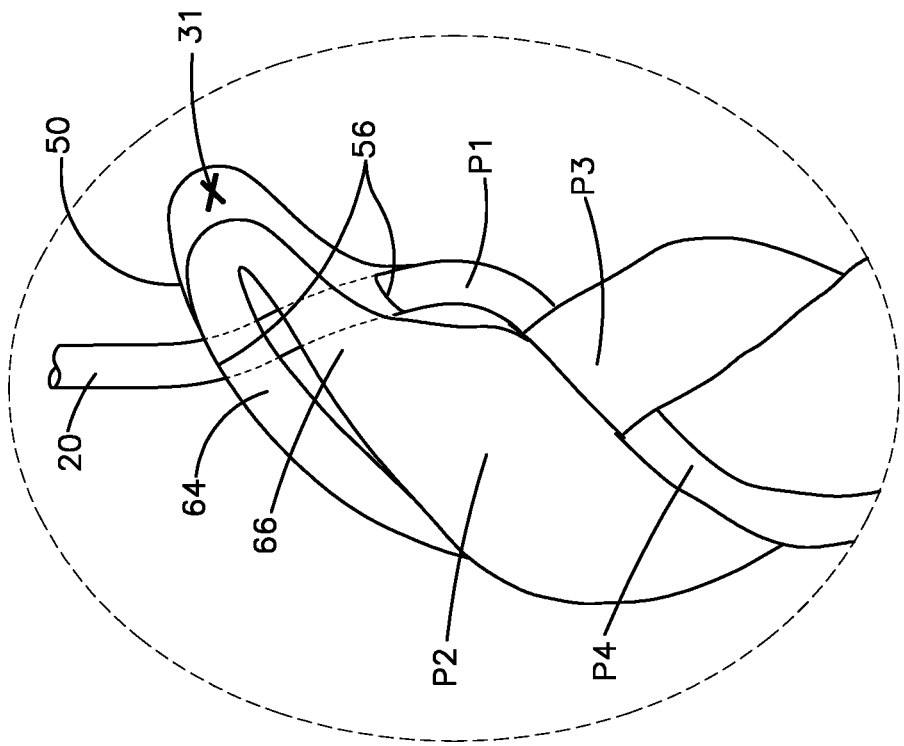
FIG. 6B is an enlarged plan view of the first end of the suture anchor illustrated in FIG. 6A.
Figure 6A:
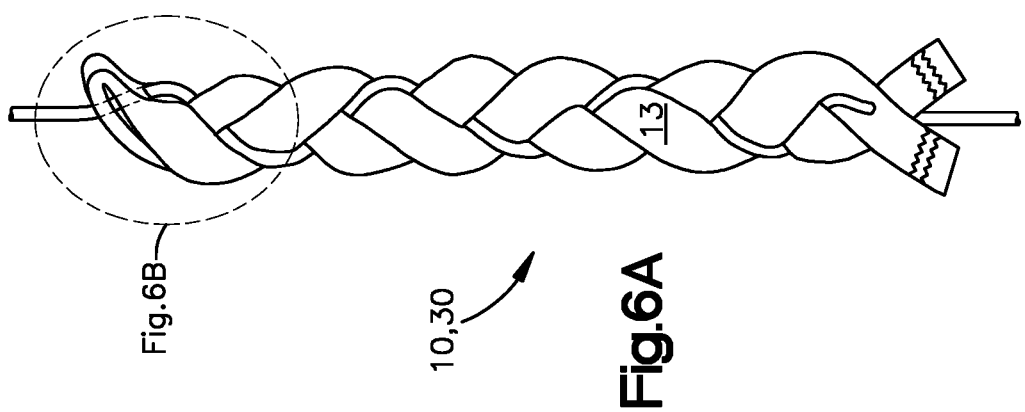
FIG. 6A is a plan view of a suture anchor similar to the suture anchor illustrated in FIG. 4K but having an alternative first end construction, according to another embodiment of the present disclosure.

With reference to FIGS. 6A and 6B, another example method of constructing a braided suture anchor 10 with the tape 65 and the actuation member 20 will now be described. The present example is similar to the example described above with reference to FIGS. 4A-4K, with the primary difference being that instead of the first penetration 56 being coincident with the first location 31, the anchor body 50 can be pinched together at the first location 31 and the actuation member 20 can penetrate both of the pinched first and second anchor body tails 64, 66 adjacent but downstream of the first location 31. Thus, in the present example, the first penetration 56 can be characterized as a joint penetration. From the first penetration 56, the actuation member 20 can cross the pinched portion of the second anchor body tail 66 to define the first pick P1. The second anchor body tail 66 can then extend from the first penetration 56 and cross the pinched portion of the first anchor body tail 64 to define the second pick P2. The first anchor body tail 64 can then cross the actuation member 20 to define the third pick P3, from which the remainder of the suture anchor body construct 30 can be braided in similar fashion as described above with reference to FIGS. 4F-4J. As in the examples described above, the suture anchor 10 of the present embodiments is configured such that the anchor body 50 and the actuation member 20 are substantially freely slidable relative to each other, both before and after transitioning to the expanded configuration C2. As above, the tape 65 according to the present embodiment can optionally be swellable when exposed to an aqueous environment, though the tape 65 need not have such swellable functionality.

With reference to FIGS. 7A-7F, an example method of constructing a suture anchor 10 with the tape 65 and the actuation member 20, particularly by wrapping the tape 65 around the actuation member 20, will now be described. As in the examples described above, the suture anchor 10 of the present embodiments is configured such that the actuation member 20 and the anchor body 50 are substantially freely slidable relative to each other, before and after transitioning to the expanded configuration C2. It should be appreciated that the tape 65 according to the present embodiment can optionally be swellable when exposed to an aqueous environment, though the tape 65 need not have such swellable functionality.

Figure 7A:
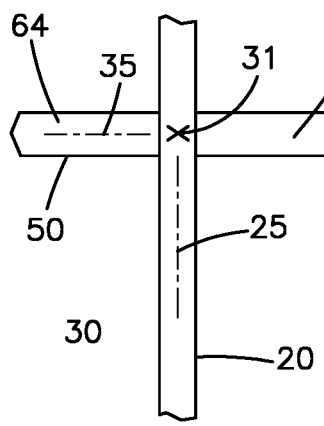
FIG. 7A-E illustrate method steps for creating a suture anchor having an anchor body wrapping helically around an actuation member, according to another embodiment of the present disclosure.
Figure 7B:
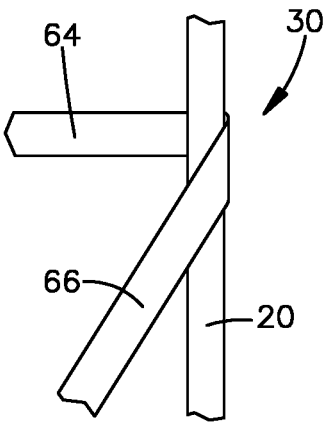
Figure 7C:
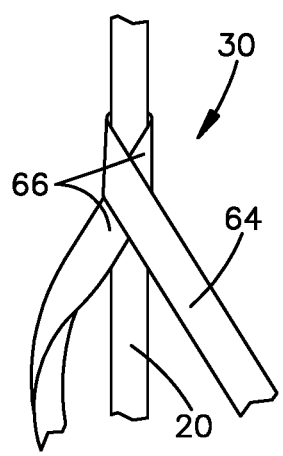
Figure 7D:
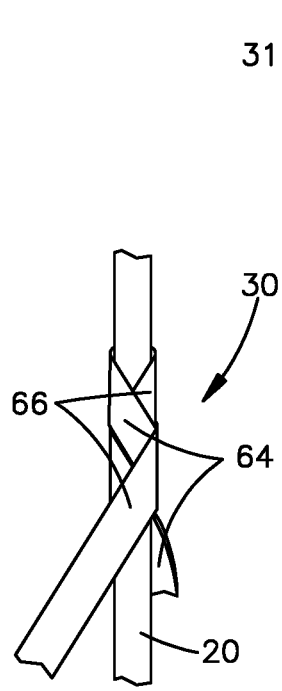
Figure 7E:
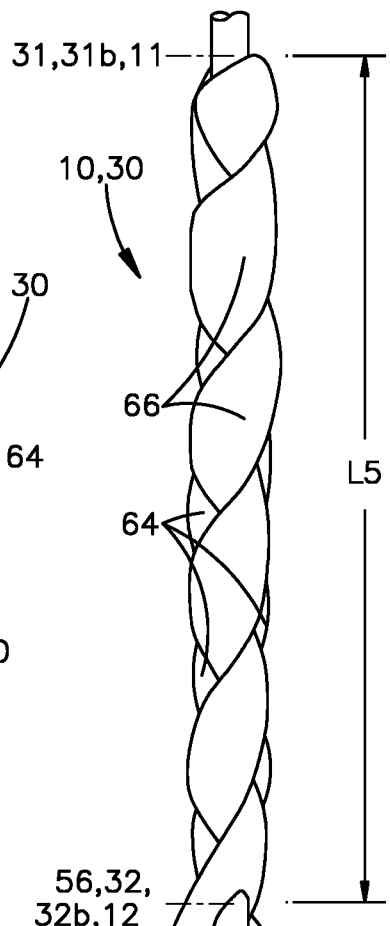

Referring now to FIG. 7A, the actuation member 20 can be placed into contact with the anchor body 50 at a first location 31, which defines a start of a braided suture anchor construct 30 formed according to the present embodiment. As in the examples above, the first location 31 can also define a first end 31b of the braided suture anchor construct 30. At the first location 31, the actuation member 20 and the anchor body 50 can be oriented relative to each other such that the longitudinal axis 25 of the actuation member 20 is angularly offset from (e.g., substantially perpendicular to) the central axis 55 of the anchor body 50, at least at the beginning of the process of forming the braided suture anchor construct 30. As shown, the first and second anchor body tails 64, 66 extend from away from each other at the first location 31.

Referring now to FIGS. 7B-7E, beginning with one of the first and second anchor body tails 64, 66 (the second anchor body tail illustrated in FIG. 7B), the anchor body tails 64, 66 can each be wrapped helically about the actuation member 20 in opposite helical directions about the longitudinal axis 25. At each complete helical revolution about the longitudinal axis 25, the anchor body tails 64, 66 will cross each other twice. At each successive cross, the anchor body tails 64, 66 can be interlaced in alternating fashion, thereby defining a helical braided pattern from the first end 31b to the second end 32b of the braided suture anchor construct 30. In the illustrated example, each of the anchor body tails 64, 66 extends about 5.5 helical revolutions about the longitudinal axis 25, at which point the anchor body tails 64, 66 are penetrated by the actuation member 20, thereby defining a first penetration 56 (which is a joint penetration) at a second location 32, which can define the second end 32b of the braided suture anchor construct 30. It should be appreciated that one or both of the anchor body tails 64, 66 can extend fewer than or more than 5.5 helical revolutions about the longitudinal axis 25, such as in a range of about 2.5 helical revolutions to about 30 helical revolutions. The braided suture anchor construct 30 defines a length L5 measured from the first end 31b to the second end 32b along the longitudinal axis 25 of the actuation member 20. The length L5 can be within the ranges described above with reference to the example shown in FIG. 4J. As above, it should be appreciated that the first and second ends 31b, 32b and the length L5 of the braided suture anchor construct 30 also define the respective first and second ends 11, 12 and length L5 of the suture anchor 10. Additionally, the remaining portions of the anchor tails 64, 66 extending from the second location 32 to their respective ends 51, 52 can be cut or otherwise trimmed to avoid obstruction with the completed suture anchor 10.

Figure 7F:
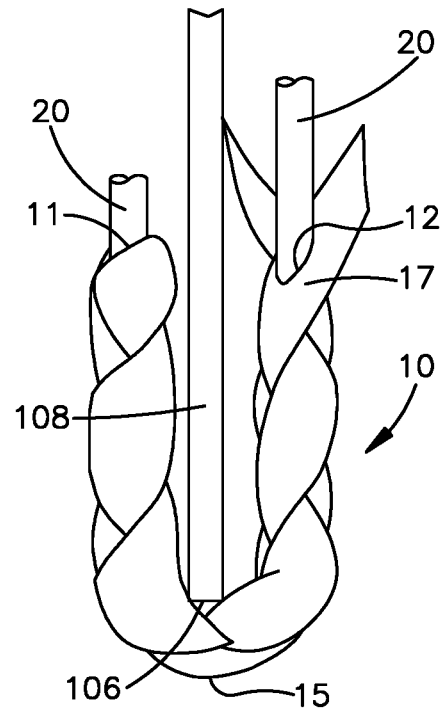
FIG. 7F is a side elevation view of the suture anchor illustrated in FIG. 7E loaded onto an insertion instrument.

Referring now to FIG. 7F, the anchor 10 can be folded or bent, such as into a U-shape or a V-shape, which can facilitate loading the anchor 10 onto and/or within an insertion instrument, such as onto the distal tip 108 of the insertion instrument 102 described above. As in the embodiments described above, the anchor 10 can be bent or folded over the distal end 106 of the instrument 102 such that the distal end 106 of the instrument 102 engages the anchor 10 at an apex of the bend, which is preferably located substantially at an axial midpoint of the anchor 10. In such embodiments, the folded or otherwise bent suture anchor 10 defines a distal end 15 at an apex of the bend or fold and a proximal end 17 substantially aligned with the first and second ends 11, 12 of the anchor 10.

It should also be appreciated that any of the braided suture anchor 10 embodiments described above can alternative employ two separate anchor bodies 50 each having a tape 65 structure. In such embodiments, the first end 31b of the braided suture anchor construct 30 can include a joint first penetration 56 through the separate anchor bodies 50, which can then be braided together with the actuation member 20 (or braided along the actuation member 20, as shown in FIGS. 7A-E) to the joint second penetration 58 at the second end 32b. In further embodiments, two or more separate anchor bodies 50, each having a tape 65 structure, can be attached to each other, such as by being bonded, pierced with a connecting strand (such as a connecting suture), fused and/or melted together, which can then be folded or wrapped around the actuation member 20 at the first location 31, and the anchor body 50 can otherwise be braided together with the actuation member 20 from the first location 31 to the second location 32 to form a braided suture anchor construct 30.

In the braided suture anchor embodiments described above, the actuation member 20 is preferably Size 2 suture (5.0 mm diameter), and preferably has a swellable core 80, such as Size 2 DYNACORD™, although other sizes and types of suture can be employed for the actuation member 20.

Figure 8A:
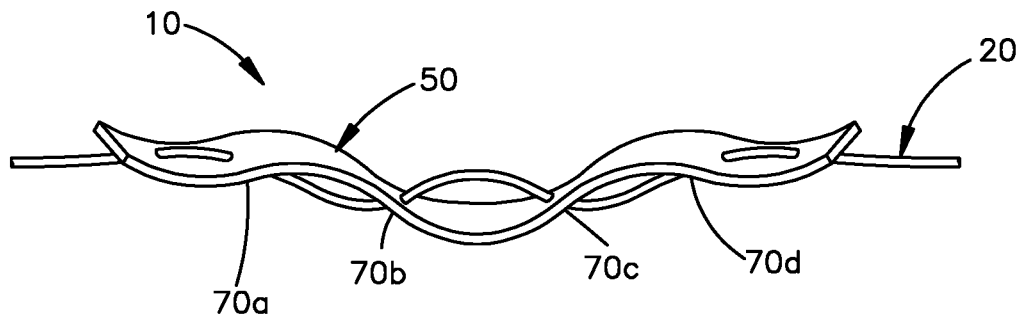
FIG. 8A-C are plan views of a suture anchor having a spliced construction, according to another embodiment of the present disclosure.
Figure 8B:
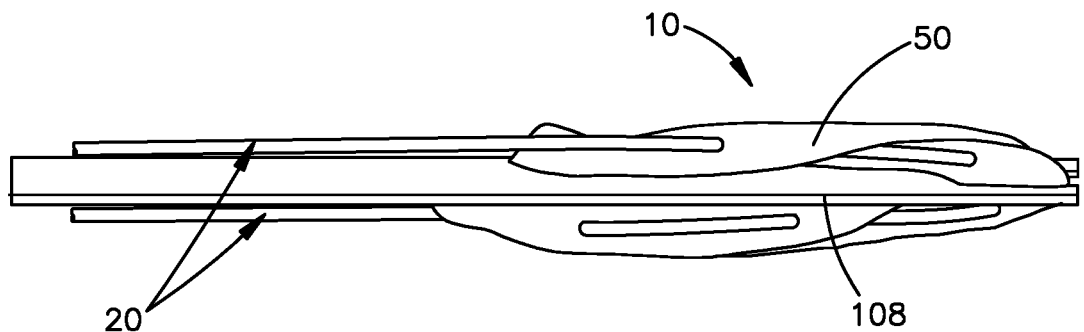
Figure 8C:
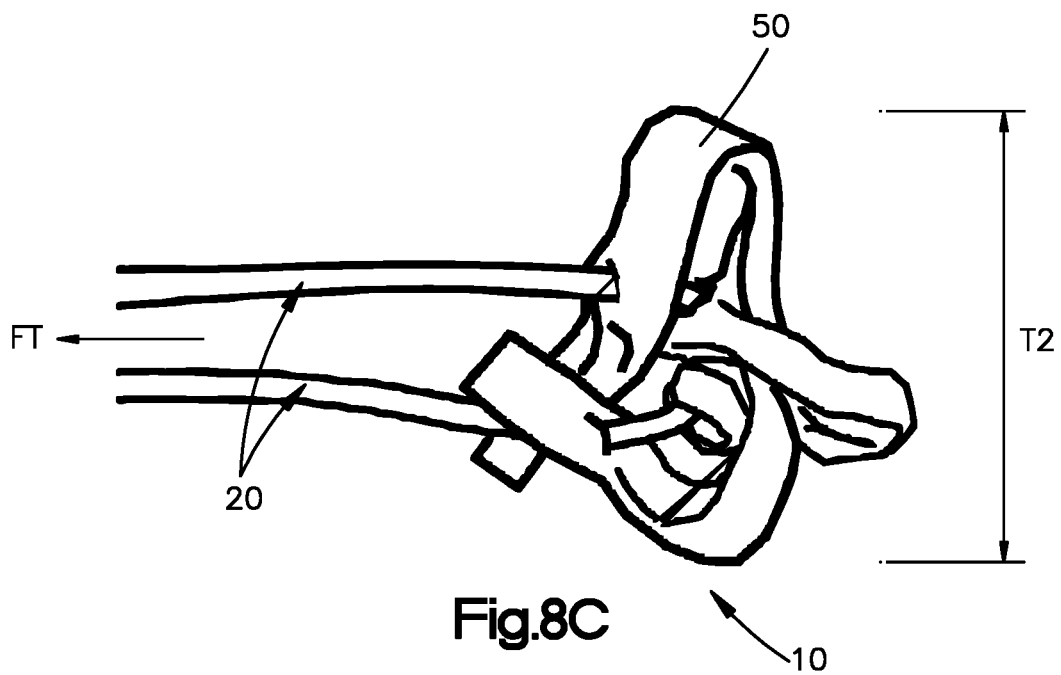

Referring now to FIGS. 8A-8C, another method of constructing a suture anchor 10 with the actuation member 20 and the anchor body 50 will be described. As shown in FIG. 8A, the anchor body 50 can be pierced, such as by a needle 60 carrying the actuation member 20, at a plurality of penetrations 70a-n along the length of the anchor body 50 in a manner forming a sinusoidal stitch pattern. Stated differently, the actuation member 20 can extend successively through: a first penetration 70a from the first side 57 to the second side 57 of the tape 65; a second penetration 70b from the second side 58 to the first side 57; a third penetration 70c from the first side 57 to the second side 58; and a fourth penetration 70d from the second side 58 to the first side 57. It is to be appreciated that the actuation member 20 can extend in like fashion through additional or fewer penetrations as needed. As mentioned above, the construction of the tape 65 renders it more readily suited for stitching or piercing the actuation member 20 therethrough. As shown in FIG. 8B, the suture anchor 10 can be loaded onto the forked end 110 of the insertion instrument 102 similarly as described above with reference to, inter alia, FIGS. 1A-B. As shown in FIG. 8C, the anchor body 50 can be actuated into the expanded configuration C2 responsive to the actuation member 20 applying a sufficient tensile force FT to the anchor body 50.

Figure 9:
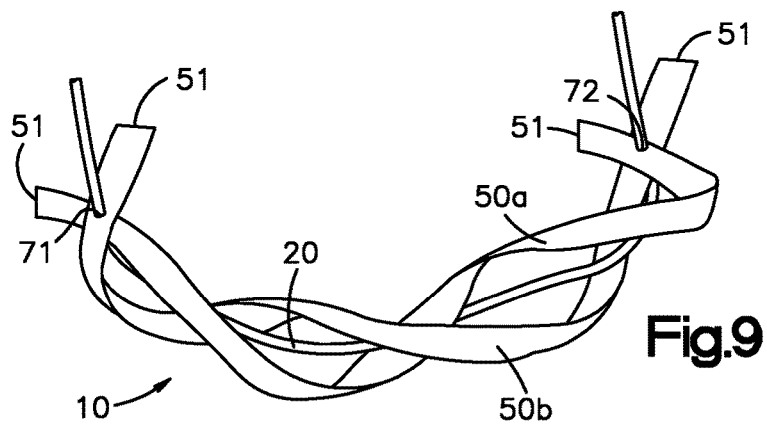
FIG. 9 is a plan view of a suture anchor that includes two anchor bodies coupled together, according to yet another embodiment of the present disclosure.

Referring now to FIG. 9, a suture anchor 10 can employ more than one of the tape anchor bodies 50 described above. In particular, the actuation member 20 can be connected to a first anchor body 50a and a second anchor body 50b, both of which have the tape structure described above. In this embodiment, the actuation member 20 penetrates jointly through the sides 57, 58 of the anchor bodies 50a-b near the first ends 51 thereof. The anchor bodies 50a-b can then be braided or woven around the actuation member 20 in a "sandal-lace" fashion (i.e., the first and second anchor bodies 50a-b are wrapped around the actuation member 20 in a double-helix configuration, or, stated more specifically, the first anchor body 50a is wrapped around the anchor member 20 in a clockwise helical direction and second anchor body 50b is concurrently wrapped around the anchor member 20 in a counter-clockwise helical direction). The actuation member 20 subsequently penetrates jointly through the sides 57, 58 of the anchor bodies 50a-b near the second ends 52 thereof. Although the present anchor embodiment has been shown to bunch together in a more elliptical shape (which tends to provide less fixation strength relative to other embodiments disclosed herein), the increased spacing between the actuation member 20 and the anchor bodies 50a-b provides this embodiment with increased slidability, which renders this embodiment well-suited for repairs where slidability is critical and/or lower fixation strengths are adequate.

Figure 10A:
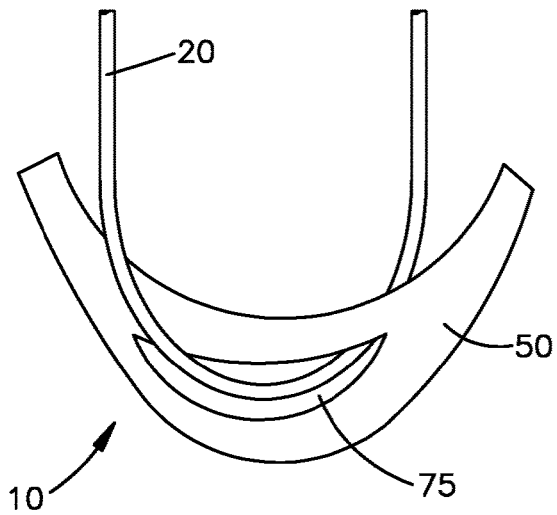
FIG. 10A is a plan view of a suture anchor that includes a bifurcated anchor body, according to a further embodiment of the present disclosure.
Figure 10B:
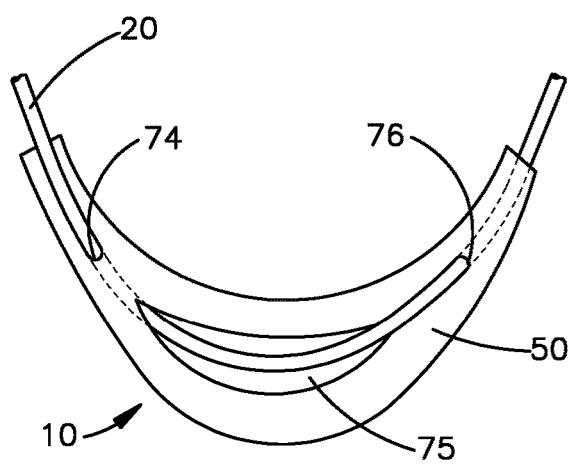
FIG. 10B is a plan view of a suture anchor that includes a bifurcated and spliced anchor body, according to yet a further embodiment of the present disclosure.

Referring now to FIGS. 10A-10B, a suture anchor 10 can employ a bifurcated tape anchor body 50. In such embodiments, the actuation member 20 can be woven through the bifurcation 75. As shown in FIG. 10B, the actuation member 20 can also be spliced with the anchor body 50, such as via penetrations 74, 76 on opposite longitudinal sides of the bifurcation 75. Advantages of this embodiment include ease of manufacturability, and also use on a narrower insertion fork, as the tines can extend through the bifurcation 75 and grip only the actuation member 20 and thus need not span the width W of the anchor body 50. Referring now to FIG. 10A, in yet another embodiment employing a bifurcated anchor body 50, the actuation member 20 can simply be advanced though the bifurcation 75 without any braiding, splicing, stitching, or piercing the anchor body 50.

Figure 11:
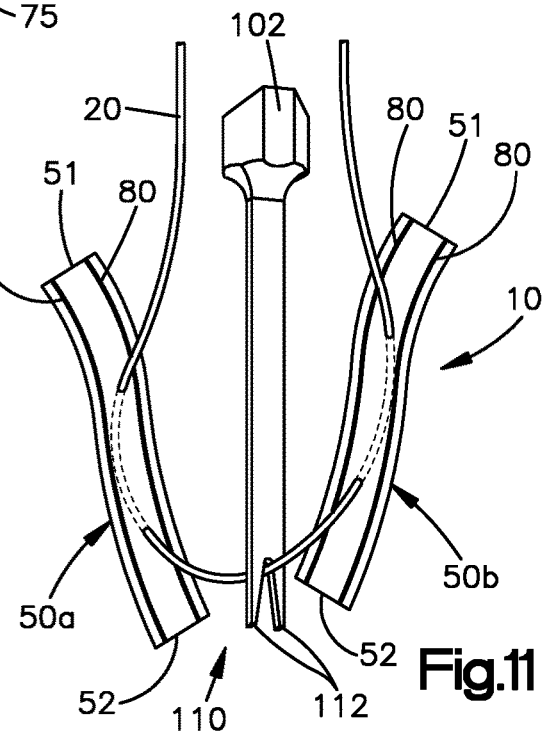
FIG. 11 is a plan view of a suture anchor that includes a pair of anchor bodies, according to an additional embodiment of the present disclosure.

Referring now to FIG. 11, a suture anchor 10 can employ a pair of anchor bodies 50a-b each having a tape construction. In this particular embodiment, the actuation member 20 can be spliced through each anchor body 50a-b separately so as to maintain a distance between the anchor bodies 50a-b when the anchor 10 is in the first configuration C1. In this embodiment, the anchor 10 can be loaded onto an insertion fork that is smaller than in previous embodiments (and about the same size as with the embodiments described above with reference to FIG. 6A-B), as the tines 112 can grip the actuation member 20 without need of spanning or gripping either of the anchor bodies 50a-b. It is to be appreciated, however, that in the present embodiment, it can be desired to couple one or both of the anchor bodies 50a-b to one or both of the fork tines 112. One way in which this can be accomplished is to employ a pre-formed hole or aperture in one or both of the anchor bodies 50a-b, such as near the second end 52 thereof so that one of the tines 112 can extend within the hole and grip the respective anchor body 50. Alternatively or additionally, one or both of the anchor bodies 50a-b can include a strand that extends from the respective anchor body 50a-b for connection to one of the tines 112.

In embodiments employing a swellable anchor body 50, one significant, unexpected advantage of providing a braided suture anchor 10 having the actuation member 20 (or other type of suture) penetrate the anchor body 50 between at least a pair of axial cores 80 is that as the cores 80 swell, the cores 80 can compress the actuation member 20 at or near the penetration more tightly, which tends to further increase the strength of the associated repair. Such a mechanism can be characterized as effectively tightening a knot (i.e., the anchor 10) after it has been tied.

Referring now to FIGS. 12A-12F, another embodiment of an insertion instrument 1202 for inserting the anchor 102 into a target location in an anatomical structure 1, such as a pre-drilled hole in bone, will be described. The insertion instrument 1202 of the present embodiment can be substantially similar to the instrument 102 described above. Accordingly, the instrument 1202 includes an elongate body portion 1214 that is elongate along the longitudinal instrument direction L, and a distal tip 1208 (also referred to herein as an "anchor carrier") that extends from the body portion 1214 in the distal direction D (i.e., the insertion direction X) and defines a distal end 1206 of the insertion instrument 1202. The elongate body portion 1214 defines an outer surface 1215, which can have a circular cross-sectional geometry. The insertion instrument 102 can include a handle 1216 that extends from the elongate body portion 1214 in the proximal direction P and defines a proximal end 1204 of the insertion instrument 1202.

As in the embodiments above, the distal tip 1208 can define a fork structure 1210 that includes a pair of tines 1212 that extend distally from the elongate body portion 1214 and are spaced from each other along the lateral instrument direction A. The tines 1212 thereby define a recess 1213 at the distal end 1206 that can be configured to receive at least a portion of the anchor 10. The distal tip 1208 can also define a one or more surfaces or "landings" 1220, 1222 located opposite each other along the transverse instrument direction T. As shown, the landings can include a first or proximal pair of landing 1220 that extend distally from the outer surface 1215 of the elongate body portion 1214 in step down fashion. The landings can also include a second or distal pair of landings 1222 that extend distally from the first pair of landings 1220 in further step down fashion. The distal tip 1208 can be configured so that the anchor 10 can be folded or otherwise bent over the distal tip 1208 as described above, which aids in the insertion of anchor 10 within a small drill hole and also helps preserve the shape of the anchor 10 during insertion. In particular, the anchor 10 can be folded or bent over the distal tip 1208 while in the initial configuration C1, such that the apex of the bent anchor 10 can extend at least partially within the recess 1213 between the tines 1212 of the fork structure 1210 and the remainder of the anchor 10 extending to the proximal end 17 thereof can interface with the distal landings 1222 and optionally with the proximal landings 1220. It should be appreciated that other tine 1212 and recess 1213 configurations can be employed on the distal tip 1208. By way of non-limiting examples, the tines 1212 can project distally to a greater or lesser extent that that shown in FIG. 12C. Additionally or alternatively, the recess 1213 can define a deeper or shallower profile, such as a shallower profile defining substantially a single radius in a plane oriented along the longitudinal and lateral directions L, A. As shown in FIG. 12D, one or both of the distal landings 1222 can be concave, thereby allowing the anchor 10 to at least partially nest within the distal landings 1222 during insertion. As shown in FIG. 12E, one or both of the proximal landings 1220 can also be concave, thereby allowing at least respective portions of the actuation member tails 21, 22 to nest therein during insertion.

The handle 1216 preferably includes a retention structure configured to retain a proximal portion of the actuation member 20 in a manner maintaining a position of the anchor 10 relative to the distal tip 1208 during insertion. As shown in FIG. 12A, the retention structure can include, for example, a channel 1224 defined by a body 1217 of the handle 1216 and configured to receive a proximal portion of the actuation member 20, such as one or both of the tails 21, 22 thereof. The channel 1224 can extend along the longitudinal instrument direction L from a distal end 1226 of the handle 1216 to the proximal end 1204. Referring now to FIG. 12F, the channel 1224 can also extend across a proximal surface 1227 of the handle 1216 at the proximal end 1204. The handle body 1217 can include a protrusion 1228 extending within the channel 1224 and interfacing with an opposite sidewall 1230 the channel 1224 in a manner defining a pinch slot 1232 therebetween. One or both of the protrusion 1228 and the opposite sidewall 1230 can define a tapered lead-in surface configured to facilitate directing one or both of the actuation member tails 21, 22 into the pinch slot 1232. It should be appreciated that other retention structure configurations are within the scope of the present disclosure. The proximal surface 1227 of the handle 1216 can be configured to receive insertion forces, such as impaction forces (e.g., from a mallet), that drive the distal tip 1208 and the anchor 10 loaded thereon into the target site of the anatomical structure 1.

Referring now to FIG. 12G, the insertion instrument 1202 can be configured for use with a guide member 1240. Accordingly, the insertion instrument 1202 and the guide member 1240 can collectively be referred to as an instrument assembly 1242. The guide member 1240 can include a handle 1244 having a proximal surface 1246 that defines a proximal end 1248 of the guide member 1240. The guide member 1240 includes an elongate guide tube 1250 extending distally from the handle 1244 and defining a distal end 1252.

As shown in to FIGS. 12H-12J, the guide tube 1250 defines a central cannulation 1254 configured to receive the elongate body portion 1214 of the insertion instrument 1202 therein and guide the elongate body portion 1214 to the target site. The guide member 1240 and the insertion instrument 1202 are cooperatively sized such that the distal tip 1208 of the insertion instrument 1202 extends distally beyond the distal end 1252 of the guide tube 1250 when the distal surface 1226 of the instrument handle 1216 abuts the proximal surface 1246 of the guide member handle 1244, which can be referred to as a "fully seated" position of the instrument 1202 relative to the guide member 1240. In particular, the entire anchor 10 loaded on the distal tip 1208 can be positioned distally of the distal end 1252 of the guide tube 1250 when the insertion instrument 1202 is fully seated with respect to the guide member 1240. It should be appreciated that a distance between the distal surface 1226 of the instrument handle 1216 and the proximal surface 1246 of the guide member handle 1244 along the longitudinal direction L can provide the surgeon with a visual indication of the depth at which the anchor 10 (loaded on the distal tip 1208 of the instrument) extends relative to the target location. The guide tube 1250 can define one or more apertures 1256 allowing external visualization within the cannulation 1254. The guide tube 1250 can also be configured to guide movement of a hole opening device, such as a drill or awl, through the cannulation 1254 and to the target site prior to inserting the elongate body portion 1214 within the cannulation 1254. As shown in FIGS. 12I and 12J, the distal end 1252 of the guide tube 1250 can have a geometry, such as a saw-tooth geometry, for purchasing with bone at the target site. It should be appreciated that other distal end geometries for purchasing with bone are within the present embodiments, including a "fish mouth" geometry, by way of a non-limiting example. As shown in FIGS. 12H and 12K, the cannulation 1254 of the guide tube 1250 can be in open communication with a central bore 1258 of the guide member handle 1244. The central bore 1258 can have a proximal portion that flares outwardly in the proximal direction P and is also aligned with the channel 1224 of the instrument handle 1216 in the proximal direction P. Accordingly, the actuation member 20 can extend proximally through the cannulation 1254 and into the central bore 1258, and in turn through the channel 1224.

With reference to FIGS. 12L-12P, use of the instrument assembly 1242 to deploy a suture anchor 10 within a target location of a bone 1, particular will now be described. As shown in FIG. 12L, the guide tube 1250 can be inserted within a patient along an insertion axis 1260 that intersects the target location of the bone 1 until the distal end 1252 of the guide tube 1250 contacts the bone 1. As shown, the distal end 1252 can "bite" into or otherwise purchase with the bone 1. As shown in FIG. 12M, with the distal end 1252 in contact with the bone 1, a hole opener 1262, such as a drill, can be advanced through the guide tube 1250 and can form a hole 3 in the bone 1 at the target location. Once the hole 3 is formed, the hole opener 1262 can be withdrawn from the guide tube 1250. As shown in FIG. 12N, the insertion instrument 1202, having an anchor 10 loaded on the distal tip 1208 thereof, can be advanced through the guide tube 1250 until the anchor 10 extends distally therefrom and into the hole 3. It should be appreciated that impactions can be applied to the proximal surface 1227 of the instrument handle 1216 as needed, such as with a mallet, until the insertion instrument 1202 fully seats against the guide member 1240 or the anchor 10 otherwise advances to a satisfactory depth within the hole 3. As shown in FIG. 12O, after the anchor 10 has reached a satisfactory depth within the hole 3, the actuation member 20, such as the tails 21, 22 thereof, can be decoupled from the retention structure of the instrument handle 1216 and the instrument 1202 and the guide member 1240 can be withdrawn from the patient, leaving the anchor 10 in the hole 3 substantially in the initial configuration C1. As shown in FIG. 12P, the surgeon can then apply the actuation force (i.e., the tensile force) to the actuation member tails 21, 22, thereby transitioning the anchor 10 into the expanded configuration C2.

Figure 13A:
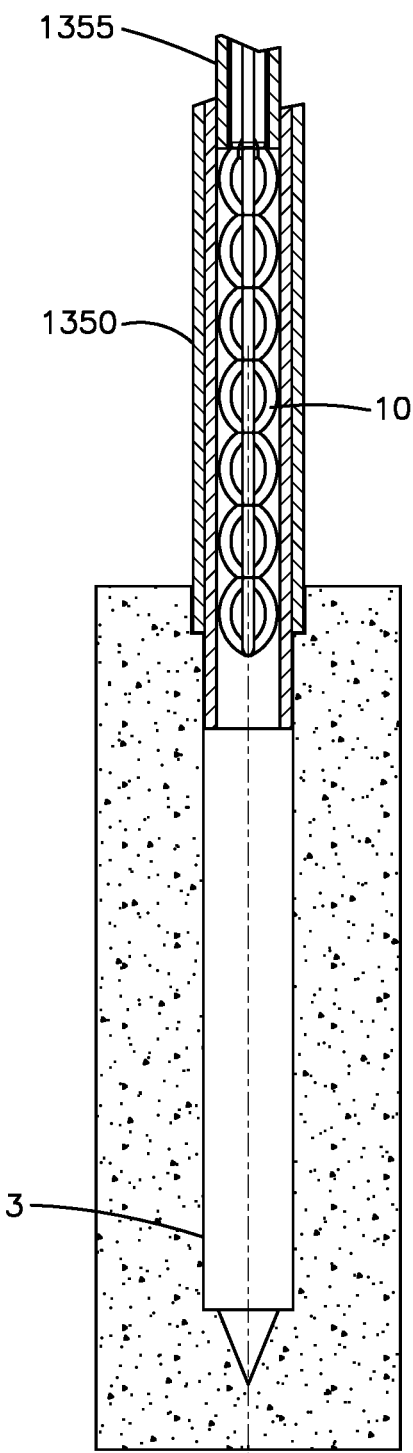
FIGS. 13A-B illustrate plan views of an insertion instrument assembly for positioning a suture anchor at a target location of an anatomical structure, according to another embodiment of the present disclosure.
Figure 13B:
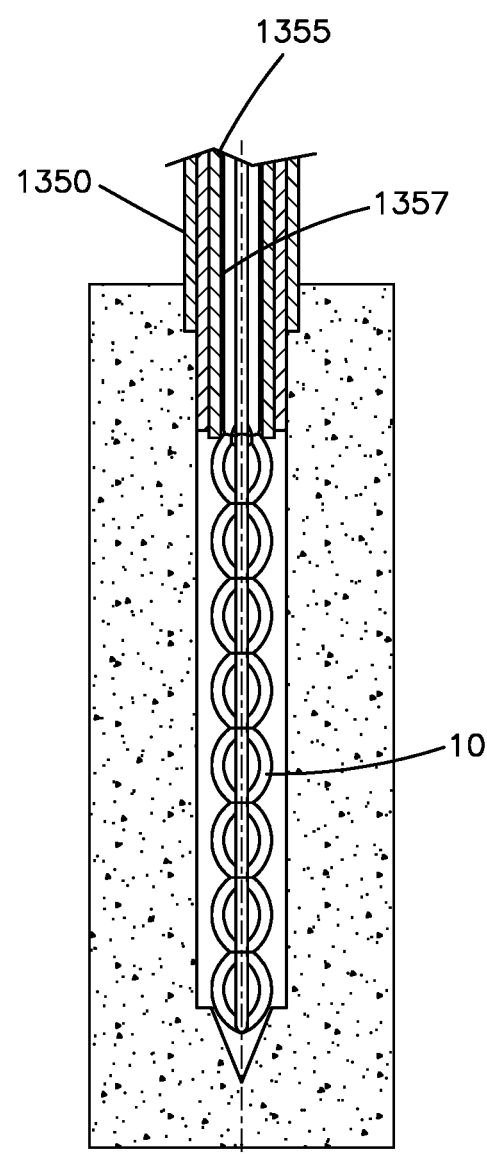

Referring now to FIGS. 13A and 13B, in other embodiments, an insertion instrument assembly can employ an outer tube 1350, which can be similar to the guide tube 1250 described above, and an insertion instrument that includes an inner push tube 1355 that is configured to push the anchor 10 into the target location, such as a hole 3 pre-formed in bone. The inner push tube 1355 defines a central bore 1357 having an inner diameter sized to receive the actuation member 20 therein but sufficiently narrow to prevent the anchor 10 from residing therein. The instrument assembly of the present embodiment can employ one or more removable retention features for selectively maintaining the longitudinal position of the inner tube 1355 relative to the guide tube 1350, such as when the assembly is advanced to the target location, and for selectively allowing the inner tube 1355 to advance along the guide tube 1350 to push the anchor 10 into the bone hole. Such pushing mechanism can also assist transition the anchor 10 into the expanded configuration C2.

It is to be appreciated that in the embodiments of the suture anchor described herein, the actuation member 20 need not pass through any longitudinal opening (e.g., a hollow core, tunnel, channel, or cannulation) that extend through the anchor body 50. Thus, any of the suture anchors 10 described herein may include an actuation member 20 that does not pass through any longitudinal opening (e.g., a hollow core, tunnel, channel, or cannulation) that extend through the anchor body 50.

Additionally, the suture anchors 10 described above with reference to FIGS. 1A-B, 1E-F, 3A-E and FIGS. 8A-C have been tested in 2.0 mm (about 0.079 inch) diameter holes in 55 Durometer sawbone media at a rate of 10 inches per minute and have demonstrated favorable fixation characteristics. The suture anchors 10 described above with reference to FIGS. 4A-7F have been tested in 1.85 mm (about 0.073 inch) diameter holes in 55 Durometer sawbone media at a rate of 10 inches per minute and have demonstrated an average fixation strength of about 157.5 N. The fixation strength of the individual anchors 10 was found to vary based on such factors as anchor design, number of picks in the braided construct, and anchor length L5, by way of non-limiting examples.

It is also to be appreciated that the sizes and dimensions of the tape anchor bodies 50, 50a-b and actuation members 20 provided above are provided for illustrated purposes, and the tape 65 is suitable for scaling up and down in size as necessary.

It is additionally to be appreciated that the suture anchors 10 described herein can be injected, inserted, or otherwise deployed with various types and configurations of insertion devices and instruments other than the instrument described above. For example, the suture tails 21, 22 are configured so as to be connectable with various types of instruments employing suture cleats, tensioners, of other mechanisms for controlling operation and/or manipulation of the suture tails for anchoring purposes, including mechanical expansion of the anchor body. For example, the actuation member 20 (such as one or both of the suture tails 21, 22 thereof) can be operatively coupled to a tensioning device having a handle and an actuator, such as, by way of non-limiting examples, a slider, a dial, a knob (e.g., a pull-style or a turn-style knob), and/or a trigger (e.g., a scissor-style handle), or other feature for manipulation by a physician. Such a tensioning device can also include a tension-limiter, such as a shear pin or other frangible member or mechanism that is configured to fail or otherwise cease transmitting the tensile force FT to the suture tails once the tensile force FT has reached a predetermined limit, which can also provide a tactile and/or auditory indication to the physician that the anchor 10 has transitioned to the expanded configuration C2.

It is further to be appreciated that the suture anchors 10 described herein are believed to be capable of being deployed within an anatomical structure and provide sufficient anchor fixation strength even if the anchor 10 expands mechanically to less than its fullest extent, utilizing the swelling mode of expansion to supplement the less-than total mechanical expansion. In such instances, it should be appreciated that the swelling can further allow the anchors 10 to maintain their fixation post-operatively over time. Moreover, the suture anchors 10 described herein are capable of being deployed within an anatomical structure and provide sufficient anchor fixation strength due to mechanical expansion alone even without the swelling mode of expansion.

It is to be appreciated that the swellable tape anchor bodies 50 described above can also be employed as connecting devices joining at least one anatomical structure with at least one of: another anatomical structure, a plurality of other anatomical structures, an anchor member, and/or a plurality of anchor members (including prior art anchor members, further including non-textile anchors). In this manner, the tape anchor bodies 50 can be employed for anatomical reduction, such as to repair or restore a gap between anatomical structures. By way of non-limiting examples, any of the anchor bodies 50 described herein can be employed in a manner connecting an anatomical structure with another type of anchor, such as the HEALIX™ or HEALIX ADVANCE™ anchors referenced above. The inventors have discovered through their own testing that the tapes 50 described herein that include swellable cores can operate effectively and advantageously when employed for suturing (i.e, tensioning and/or anatomical reduction) functions. Moreover, it is to be appreciated that the tapes 50 described above can be constructed and implanted in such a manner so as to provide anchoring and suturing functionality concurrently.

It is also to be appreciated that each of the anchor bodies 50 described above can also be employed with more than one actuation member 20, such in embodiments involving double- or triple-loaded anchors, by way of non-limiting examples.

It is further to be appreciated that the actuation members 20 disclosed above can also be employed with other types of anchors, including expanding knot anchors utilizing anchor bodies other than the tapes 65 disclosed above. In one such example, the actuation member 20 can be configured in such as way (e.g., being pre-tied, woven, and/or braided) so as to also define an anchor body that is mechanically expandable responsive to a tensile force applied to one or more "tails" of the actuation member 20. The actuation members 20 disclosed herein can also be employed with other types of knot anchors. In these embodiments, the swellability of the actuation member 20 can provide additional expansion to the anchor. It is further to be appreciated that the actuation members 20 disclosed herein can also be employed with other types of anchors, including rigid anchors, as desired. In each of these embodiments, the swellability of the actuation member 20 can provide the advantage of contracting along at least a portion of its length between connected members so as to reduce the distance between the connected members, which can maintain compression across a repair and reduce any gap (if one is present).

It is yet furthermore to be appreciated that methods of using any of the anchor members 50 and/or actuation members 20 described above in an anatomical repair are within the scope of the present disclosure.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A suture anchor for fixation within an anatomical structure, the suture anchor comprising:
    an anchor body elongated along a direction of elongation, the anchor body defining a central axis, the anchor body having a flat geometry in a neutral configuration such that, in the neutral configuration, the anchor body defines a thickness along a transverse direction and a width along a lateral direction, wherein the transverse direction is perpendicular to the central axis, the lateral direction is perpendicular to the transverse direction, and the width is greater than the thickness in the neutral configuration; and
    an actuation member contacting the anchor body at a first location of the anchor body, the anchor body having first and second anchor body tails extending away from the first location, the first and second anchor body tails being braided together along a portion of the actuation member from the first location to a second location of the anchor body spaced from the first location so as to define a braided suture anchor construct,
    wherein the actuation member is configured to apply a force to the anchor body so as to actuate the anchor body from a first configuration, in which the anchor body defines a first maximum thickness along a second direction that is angularly offset from the direction of elongation, to an expanded configuration, in which the anchor body defines a second maximum thickness along the second direction, wherein the second maximum thickness is greater than the first maximum thickness;
    wherein the first and second anchor body tails contact each other at the second location, such that the first and second locations define first and second ends of the braided suture anchor construct, and the braided suture anchor construct defines a length extending between the first and second ends along a longitudinal construct direction;
    wherein the actuation member comprises:
        a first actuation member tail that extends from the first location and away from the portion of the actuation member; and
        a second actuation member tail that extends from the second location and away from the portion of the actuation member;
    wherein the actuation member penetrates at least one of the first and second anchor body tails at the second location; and
    wherein a portion of the anchor body is folded so as to define a loop extending from the first location, the braided suture anchor construct is bent such that 1) the first and second actuation member tails each extend through the loop and 2) the loop extends around at least one of the first and second ends of the braided suture anchor construct.

2. The suture anchor of claim 1, wherein the actuation member does not penetrate the anchor body at the first location.

3. The suture anchor of claim 1, wherein the actuation member includes an axial core embedded therein and extending along the direction of elongation, wherein the axial core is configured to swell along the second direction responsive to exposure to an aqueous environment.

4. The suture anchor of claim 1, wherein the anchor body bunches as it transitions from the first configuration to the expanded configuration.

5. The suture anchor of claim 1, wherein the anchor body is configured to translate along the actuation member before and after transitioning from the first configuration to the expanded configuration.

6. The suture anchor of claim 1, wherein the first and second anchor body tails are braided together with the portion of the actuation member in a three-strand alternating braid.

* * * * *